(12) United States Patent
Kilian et al.

(10) Patent No.: US 8,426,342 B2
(45) Date of Patent: Apr. 23, 2013

(54) METHOD FOR WEED CONTROL IN LAWN

(75) Inventors: Michael Kilian, Leverkusen (DE);
Eckhard Rose, Liederbach (DE); Erwin Hacker, Hochheim (DE); Hansjoerg Dietrich, Liederbach am Taunus (DE); Klemens Minn, Hattersheim (DE); Donald Myers, Wake Forest, NC (US)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/506,456

(22) Filed: Jul. 21, 2009

(65) Prior Publication Data
US 2010/0016158 A1 Jan. 21, 2010

Related U.S. Application Data

(60) Provisional application No. 61/187,021, filed on Jun. 15, 2009, provisional application No. 61/220,307, filed on Jun. 25, 2009.

(30) Foreign Application Priority Data

Jul. 21, 2008 (EP) .................................... 08013071

(51) Int. Cl.
*C07D 251/48* (2006.01)
*A01N 43/68* (2006.01)

(52) U.S. Cl.
USPC .................. 504/116.1; 504/232; 455/208

(58) Field of Classification Search ............... 504/116.1, 504/232; 544/208
See application file for complete search history.

(56) References Cited

U.S. PATENT DOCUMENTS

| | | | | |
|---|---|---|---|---|
| 5,167,693 A | * | 12/1992 | Drewes et al. | ................ 504/196 |
| 6,069,114 A | | 5/2000 | Lorenz et al. | |
| 2004/0002424 A1 | | 1/2004 | Minn et al. | |
| 2004/0157739 A1 | | 8/2004 | Ahrens et al. | |
| 2006/0014642 A1 | * | 1/2006 | Hacker et al. | ................ 504/133 |
| 2007/0238617 A1 | | 10/2007 | Minn et al. | |
| 2007/0293399 A1 | | 12/2007 | Minn et al. | |

FOREIGN PATENT DOCUMENTS

| | | |
|---|---|---|
| EP | 0 864 567 | 9/1998 |
| EP | 1 484 324 | 12/2004 |
| JP | 08 245316 | 9/1996 |

* cited by examiner

*Primary Examiner* — Fereydoun G Sajjadi
*Assistant Examiner* — Courtney Brown
(74) *Attorney, Agent, or Firm* — Frommer Lawrence & Haug LLP

(57) ABSTRACT

The invention relates to the use of one or more compounds of the formula (I) or salts thereof,

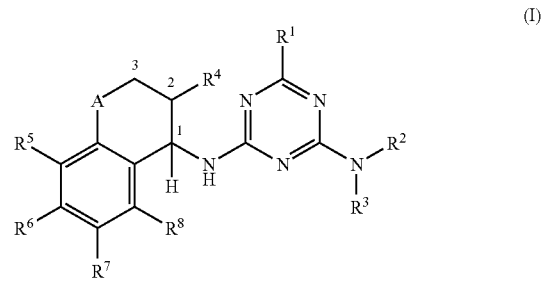

(I)

wherein
the groups $R^1$ to $R^8$ are defined as set forth herein, optionally in the presence of additional agrochemical active ingredients, for selective weed control on turf or lawn.

15 Claims, No Drawings

METHOD FOR WEED CONTROL IN LAWN

This application claims benefit under 35 U.S.C. 119(a) of European patent application 08 013 071.9, filed on 21 Jul. 2008 and under 35 U.S.C. 119(e) of U.S. Provisional Applications 61/187,021 (filed on 15 Jun. 2009) and 61/220,307 (filed on 25 Jun. 2009).

Any foregoing applications, including European patent application EP 08 013 071.9, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to the field of plant protection and environmental health, more specifically to the use of agrochemicals for selective weed control in certain useful plants, particularly in various plants used for lawn or turf, and to improve turfgrass quality.

High quality, healthy turf or lawn is essential, for example, in the golfing industry but also generally desired for lawns, turf or green areas for parks, public or private gardens, sports grounds or arenas (e.g. more specifically turf for golf courses, horse racing, football, baseball, hockey, tennis), and for greens in flower gardens, ornamental gardens, plantations and orchards. In the lawn management for instance in a garden, golf course, public green areas, roadsides, etc., control of lawn weeds is the most important task for keeping views and good maintenance of the sites. Up to now, however, there have been no satisfactory herbicides for lawn or turf.

For the purpose of weed control in lawn or turf the agrochemicals to be used have to show a selective action against the weeds, namely annual and perennial weeds and moss, without substantial injury to the turf-grass or lawn. Many herbicides used in weed control management do not show the selectivity required. Other agrochemicals have disadvantages in that the weed plants are not controlled sufficiently or that some weeds are not controlled at all (gaps). Therefore, there is a need for novel and alternative methods to enhance turfgrass quality and protect turfgrass against weeds.

Compounds from the structural class of substituted diamino-s-triazines which are N-substituted with certain bicyclic radicals are known as herbicides useful for weed-control against a broad range of weeds in pre-emergence and post-emergence application; see e.g. WO-A-97/31904 (or U.S. Pat. No. 6,069,114) or WO-2004/069814 (U.S. 2004/0157739), EPA-0864567, WO 2007/115695 (U.S. 2007/0238617), WO 2007/118589 (U.S. 2007/0293399), WO 03/070710 (U.S. 2004/0002424). The selective use of the compounds generally depends on the application rate and is practically limited to certain crop plants, preferably to various plantation crops. It is also known to combine such herbicidal active ingredients with some other herbicides for weed control, see e.g. WO 2006/007947 (U.S. 2006/014642).

Now it has been found that some compounds selected from the above group of substituted diamino-s-triazines surprisingly can be used for selective weed control in turf or lawn without substantial injury to the turf-grass or lawn. The selectivity for weed control in turfgrass is surprising because compounds (I) are otherwise known to be very active not only against dicotyledonous weeds but against many grass weeds as well.

One object of the invention is the use of one or more compounds of the formula (I) or salts thereof,

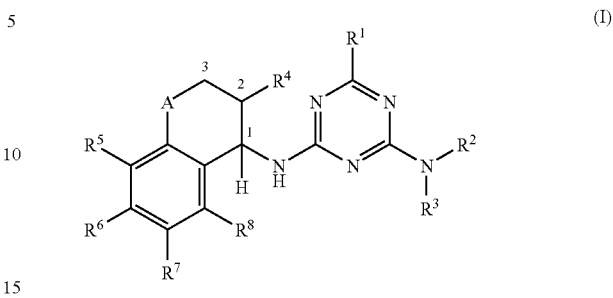

where
$R^1$ is H or a group of the formula $CZ^1Z^2Z^3$, where
$Z^1$ is H, halogen, $(C_1-C_6)$alkyl, $(C_1-C_6)$haloalkyl, $[(C_1-C_4)$alkoxy]-$(C_1-C_6)$alkyl, $(C_3-C_6)$cycloalkyl which is unsubstituted or substituted by one or more radicals selected from the group consisting of halogen, $(C_1-C_4)$alkyl and $(C_1-C_4)$haloalkyl, or is
$(C_2-C_6)$alkenyl, $(C_2-C_6)$alkinyl, $(C_2-C_6)$haloalkenyl, $(C_4-C_6)$cycloalkenyl, $(C_4-C_6)$halocycloalkenyl, $(C_1-C_6)$alkoxy or $(C_1-C_6)$haloalkoxy,
$Z^2$ is H, halogen, $(C_1-C_6)$alkyl or $(C_1-C_4)$alkoxy, or
$Z^1$ and $Z^2$ together with the carbon atom of the group $CZ^1Z^2Z^3$ represent $(C_3-C_6)$cycloalkyl or $(C_4-C_6)$cycloalkenyl, where each of the two last-mentioned radicals is unsubstituted or substituted by one or more radicals selected from the group consisting of $(C_1-C_4)$alkyl, and
$Z^3$ is H, $(C_1-C_6)$alkyl, $(C_1-C_4)$alkoxy or halogen,
$R^2$ and $R^3$ independently of one another are H, $(C_1-C_4)$alkyl, $(C_1-C_4)$haloalkyl, $(C_3-C_4)$alkenyl, $(C_3-C_4)$haloalkenyl, $(C_3-C_4)$alkinyl, $(C_3-C_4)$haloalkinyl or an acyl group,
$R^4$ is H, $(C_1-C_6)$alkyl or $(C_1-C_6)$alkoxy,
$R^5$, $R^6$, $R^7$ and $R^8$ independently of one another are H, $(C_1-C_4)$alkyl, $(C_1-C_3)$haloalkyl, halogen, $(C_1-C_3)$alkoxy, $(C_1-C_3)$haloalkoxy or cyano, and
A is a divalent group of the formula $CH_2$ or O or is a direct bond,
for selective weed control in turf or lawn.

In the following the compounds of formula (I) or their salts to be used according to the invention are also in short named as "compounds (I) according to the invention" or just "compounds (I)".

The compounds (I) or salts thereof are generally known from WO 97/31904 or WO-2004/069814 or can be prepared according to the processes described therein. Preferred are compounds (I) or salts thereof, where
$R^1$ is H or a group of the formula $CZ^1Z^2Z^3$, where
$Z^1$ is hydrogen, halogen, $(C_1-C_4)$alkyl, $(C_1-C_4)$haloalkyl, $[(C_1-C_4)$alkoxy]-$(C_1-C_6)$alkyl, $(C_3-C_6)$cycloalkyl which is unsubstituted or substituted by one or more $(C_1-C_4)$alkyl groups, or is
$(C_2-C_4)$alkenyl, $(C_2-C_4)$alkinyl, $(C_1-C_4)$alkoxy or $(C_1-C_4)$haloalkoxy;
$Z^2$ is hydrogen, halogen, $(C_1-C_4)$alkyl or
$Z^1$ and $Z^2$ together with the carbon atom of the group $CZ^1Z^2Z^3$ represent $(C_3-C_6)$cycloalkyl and
$Z^3$ is hydrogen, $(C_1-C_4)$alkyl, $(C_1-C_2)$alkoxy or halogen,
$R^2$ is hydrogen, $(C_1-C_4)$alkyl, $(C_1-C_4)$haloalkyl, $(C_3-C_4)$alkenyl, $(C_3-C_4)$haloalkenyl, $(C_3-C_4)$alkinyl, $(C_3-C_4)$haloalkinyl or an acyl group having 1 to 12 carbon atoms, wherein acyl preferably is selected from the group consisting of formyl, phenylcarbonyl, phenoxycarbonyl, where phenyl in the two last-mentioned groups is unsubstituted or substituted by one or more radicals selected from the group consisting halogen, $(C_1-C_2)$alkyl, $(C_1-C_2)$haloalkyl, $(C_1-C_2)$alkoxy, $(C_1-C_2)$haloalkoxy and nitro, or $(C_1-C_6)$alkyl-carbonyl, $(C_1-C_6)$alkoxy-carbonyl or $(C_1-C_6)$alkyl-sulfonyl),
$R^3$ is hydrogen, $(C_1-C_4)$alkyl or $(C_1-C_4)$haloalkyl,
$R^4$ is hydrogen, $(C_1-C_3)$alkyl or $(C_1-C_3)$alkoxy,
$R^5$, $R^6$, $R^7$ and $R^8$ independently of each other are hydrogen, $(C_1-C_3)$alkyl, halogen or $(C_1-C_3)$alkoxy, and
A is a divalent group of the formula $CH_2$ or O or is a direct bond, preferably is $CH_2$ or a direct bond, more preferably is a direct bond.

Preferred are optically active compound of the formula (I) or their salts, where the stereochemical configuration at the carbon atom marked with the number 1 in formula (I) is the (R)-configuration having an optical purity corresponding to 60 to 100% (R)-isomer or isomers, preferably 70 to 100% (R)-isomer(s), more preferably 80 to 100% (R)-isomer(s), in each case relative to the total amount of the stereoisomer(s) contained in the compound having (R)- and (S)-configuration at the position 1. The configuration is defined according to the system of Cahn-Ingold-Prelog, using the following ranking of substitutents at the position 1:
1st priority refers to the substituted amino group NH;
2nd priority refers to the next carbon atom of the phenyl ring;
3rd priority refers to the other ring carbon atom;
4th priority refers to the hydrogen atom.

More preferred are optically active compounds of the formula (I) or their salts, where the radical $R^1$ is a group of the formula $CZ^1Z^2Z^3$, where $CZ^1Z^2Z^3$ is as defined above, particularly such compounds, where the stereochemical configuration at the carbon atom (shown) of the group $CZ^1Z^2Z^3$ is the (R,S)-configuration or is the (R)-configuration having an optical purity corresponding to 60 to 100% (R), preferably 70 to 100% (R), more preferably 80 to 100% (R), in each case relative to the total amount of the stereoisomer or stereoisomers contained in the compound having (R)- and (S)-configuration at this position in the compound.

Examples for compounds of formula (I) are set forth in Table 1 below.

Abbreviations in Table 1: The compounds in Table 1 are defined by the chemical formula of the main isomer, wherein the isomer is present in a chemical purity of at least 95 percent by weight. The compounds of formula (I) can be used with less purity. Similar herbicidal activities are observed, especially if the other components are mainly consisting of other herbicidally active stereoisomers of the compounds (I). Therefore, also preferred are mixtures of one or more compounds (I) selected from the compounds of Table 1. For the reason of more simple preparation mixtures of compounds (I) are preferred consisting of a compound of Table 1 in mixture with another active stereoisomer or stereoisomers from Table 1, having the same chemical constitution.

If a chemical formula in Table 1 graphically indicates a stereochemical orientation of the bonds at a chiral carbon atom and/or indicates the stereochemical configuration by the symbol (R) or (S) according to the system of Cahn, Ingold and Prelog, the compound defined contains a main component having the R- or S-configuration at the marked position and thus is optically active.

If the stereochemical configuration is not mentioned in case of chiral centers the compound is present in the racemic form.

If the compound contains several chiral centers (asymmetrically substituted carbon atoms) and the configuration is not mentioned, the compounds are in the racemic form at the respective chiral center or close to the racemic mixture. For practical purposes mixtures of diastereomers in racemic form having different ratios of the diastereomeric components can also be used.

The carbon atom attached to the amino group linked to the bicyclic radical is marked as carbon atom 1. The carbon atom of the group $R^1$ (if $R^1$ is not hydrogen) linked to the triazine ring is marked as carbon atom 1*.

TABLE 1

Compounds of the formula (I):

| Compound no. | Chemical Formula |
|---|---|
| A1 | (structure with $CH_3$) |
| A2 | (structure with $CHFCH_3$) |
| A3 | (structure with $CF(CH_3)_2$) |
| A4 | (structure with $H_3C$, H, F, 1*R) |
| A5 | (structure with $H_3C$, $NH_2$) |
| A6 | (structure with $CH_3$, $H_3C$) |
| A7 | (structure with $CH(CH_3)_2$, $H_3C$) |

TABLE 1-continued
Compounds of the formula (I):
| Compound no. | Chemical Formula |
|---|---|
| A8 | 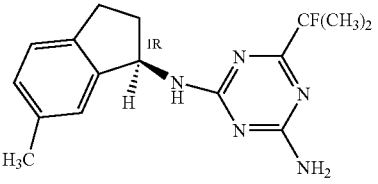 |
| A9 | 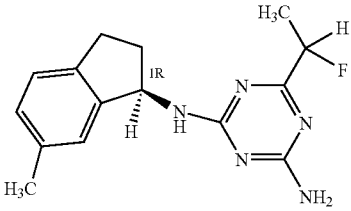 |
| A10 | 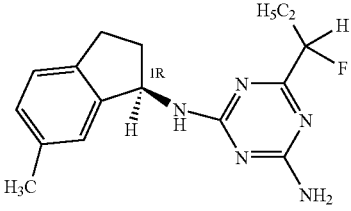 |
| A11 | 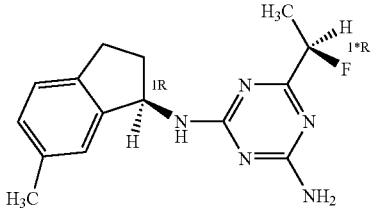 [SMILES: Cc1ccc2c(c1)[C@H](Nc1nc(N)nc([C@@H](C)F)n1)CC2] |
| A12 | 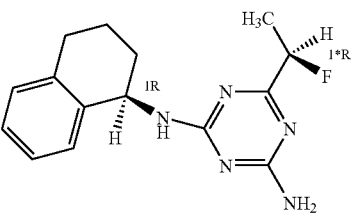 [SMILES: C[C@@H](F)c1nc(N)nc(N[C@@H]2CCCc3ccccc32)n1] |
| A13 | 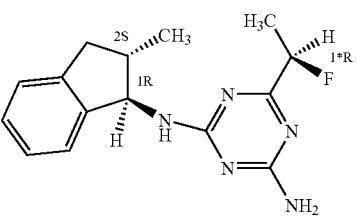 [SMILES: C[C@@H](F)c1nc(N)nc(N[C@H]2c3ccccc3C[C@@H]2C)n1] |
| A14 | 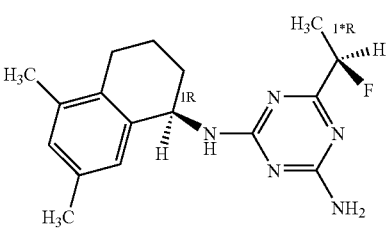 [SMILES: Cc1cc(C)c2c(c1)[C@H](Nc1nc(N)nc([C@@H](C)F)n1)CCC2] |
| A15 | 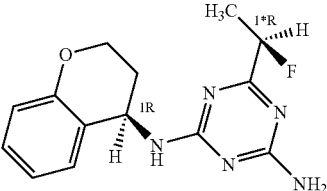 |
| A16 | 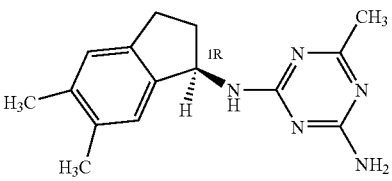 [SMILES: Cc1nc(N)nc(N[C@@H]2CCc3cc(C)c(C)cc32)n1] |
| A17 | 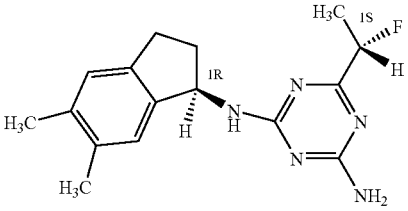 [SMILES: Cc1cc2c(cc1C)[C@H](Nc1nc(N)nc([C@H](C)F)n1)CC2] |
| A18 | 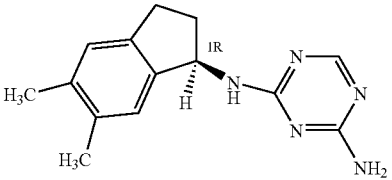 [SMILES: Cc1cc2c(cc1C)[C@H](Nc1ncnc(N)n1)CC2] |
| A19 | 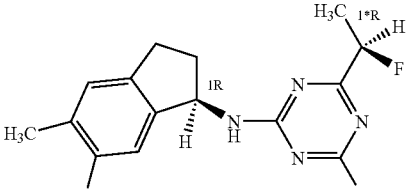 |
| A20 | 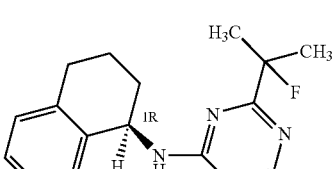 |
| A21 | 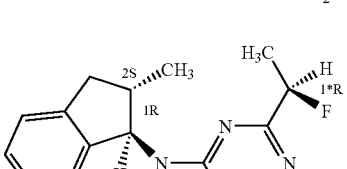 |

TABLE 1-continued

Compounds of the formula (I):

| Compound no. | Chemical Formula |
|---|---|
| A22 | (structure) |
| A23 | (structure) |
| A24 | (structure) |
| A25 | (structure) |
| A26 | (structure) |
| A27 | (structure) |
| A28 | (structure) |
| A29 | (structure) |
| A30 | (structure) |
| A31 | (structure) |
| A32 | (structure) |
| A33 | (structure) |
| A34 | (structure) |
| A35 | (structure) |

TABLE 1-continued

Compounds of the formula (I):

| Compound no. | Chemical Formula |
|---|---|
| A36 | (structure) |
| A37 | (structure) |
| A38 | (structure) |
| A39 | (structure) |
| A40 | (structure) |
| A41 | (structure) |
| A42 | (structure) |
| A43 | (structure) |
| A44 | (structure) |
| A45 | (structure) |
| A46 | (structure) |
| A47 | (structure) |
| A48 | (structure) |
| A49 | (structure) |

TABLE 1-continued

Compounds of the formula (I):

| Compound no. | Chemical Formula |
|---|---|
| A50 | (structure) |
| A51 | (structure) |
| A52 | (structure) |
| A53 | (structure) |
| A54 | (structure) |
| A55 | (structure) |
| A56 | (structure) |
| A57 | (structure) |
| A58 | (structure) |
| A59 | (structure) |
| A60 | (structure) |
| A61 | (structure) |
| A62 | (structure) |
| A63 | (structure) |

TABLE 1-continued
Compounds of the formula (I):
| Compound no. | Chemical Formula |
|---|---|
| A64 | 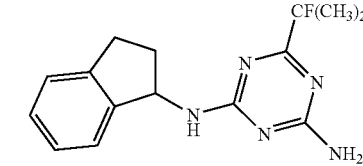 |
| A65 | 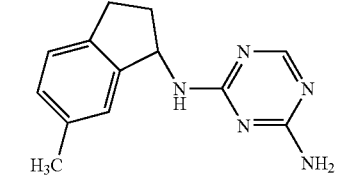 [SMILES: Cc1ccc2c(c1)C(Nc1ncnc(N)n1)CC2] |
| A66 | 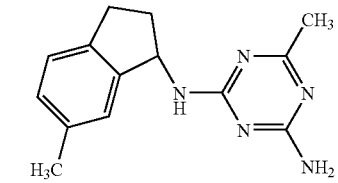 [SMILES: Cc1ccc2c(c1)C(Nc1nc(C)nc(N)n1)CC2] |
| A67 | 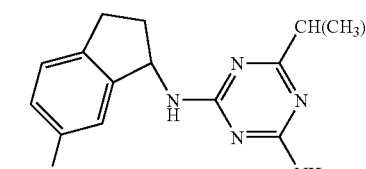 |
| A68 | 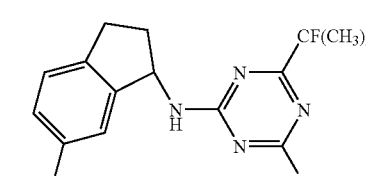 |
| A69 | 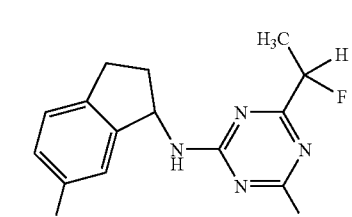 |
| A70 | 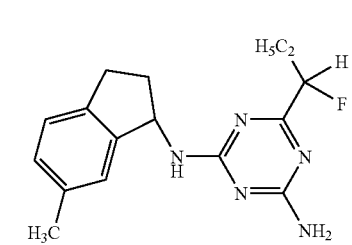 [SMILES: Cc1ccc2c(c1)C(Nc1nc(N)nc(C(C)F)n1)CC2] |
| A71 | |
| A72 | |
| A73 | |
| A74 | |
| A75 | |
| A76 | |
| A77 | |

TABLE 1-continued

Compounds of the formula (I):

| Compound no. | Chemical Formula |
|---|---|
| A78 | 1,2,3,4-tetrahydronaphthalen-1-yl-NH-triazine(CHFCH₃)(NH₂) |
| A79 | 2-methyl-indan-1-yl-NH-triazine(CHFCH₃)(NH₂) |
| A80 | 5,7-dimethyl-1,2,3,4-tetrahydronaphthalen-1-yl-NH-triazine(CHFCH₃)(NH₂) |
| A81 | chroman-4-yl-NH-triazine(CHFCH₃)(NH₂) |
| A82 | 5,6-dimethyl-indan-1-yl-NH-triazine(CH₃)(NH₂) |
| A83 | 5,6-dimethyl-indan-1-yl-NH-triazine(H)(NH₂) |
| A84 | 5,6-dimethyl-indan-1-yl-NH-triazine(CHFCH₃)(NH₂) |
| A85 | 2,6-dimethyl-indan-1-yl-NH-triazine(CHFCH₃)(NH₂) |
| A86 | 6-methyl-indan-1-yl-NH-triazine(CH₂CH₃)(NH₂) |
| A87 | 6-methyl-indan-1-yl-NH-triazine(CH₂CH₂CH₃)(NH₂) |
| A88 | 1,2,3,4-tetrahydronaphthalen-1-yl-NH-triazine(CHF-C₂H₅)(NH₂) |
| A89 | 5-fluoro-6-methyl-indan-1-yl-NH-triazine(CHFCH₃)(NH₂) |
| A90 | 5-fluoro-6-methyl-indan-1-yl-NH-triazine(CH₂CH₃)(NH₂) |
| A91 | 5-fluoro-6-methyl-indan-1-yl-NH-triazine(CH₃)(NH₂) |

TABLE 1-continued
Compounds of the formula (I):
| Compound no. | Chemical Formula |
|---|---|
| A92 | 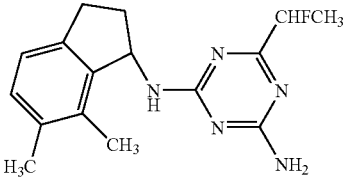 |
| A93 | 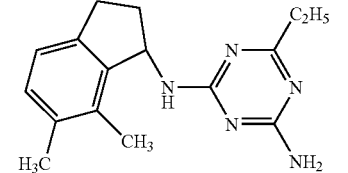 |
| A94 | 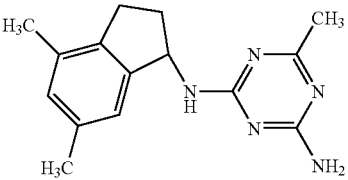 |
| A95 | 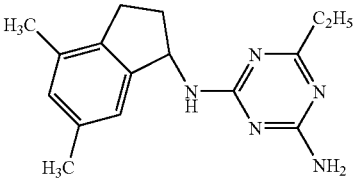 [SMILES: CCc1nc(N)nc(NC2CCc3c(C)cc(C)cc32)n1] |
| A96 | 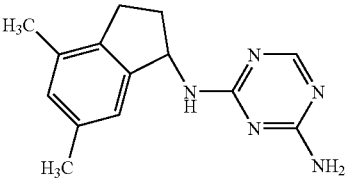 [SMILES: Cc1cc(C)c2c(c1)C(Nc1ncnc(N)n1)CC2] |
| A97 | 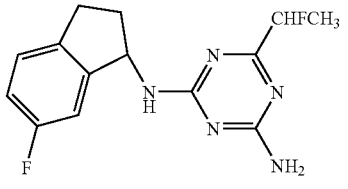 |
| A98 | 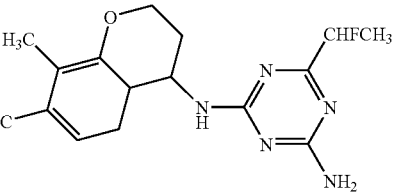 |
| A99 | 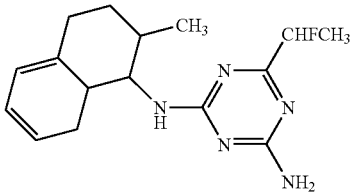 |
| A100 | 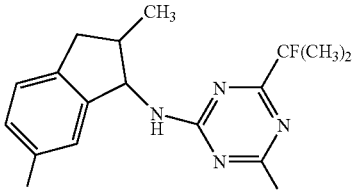 |
| A101 | 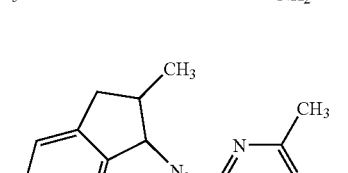 |
| A102 | 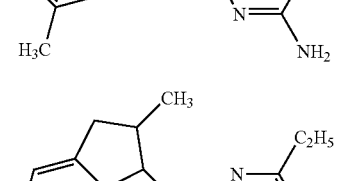 |
| A103 | 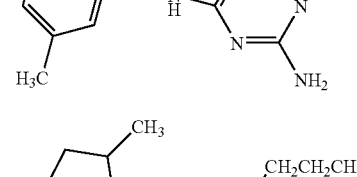 |
| A104 | 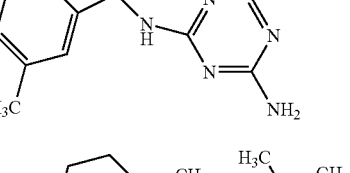 |
| A105 | 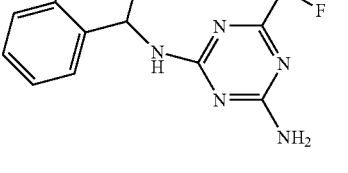 |
| A106 | 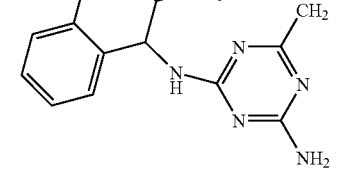 |

TABLE 1-continued
Compounds of the formula (I):
| Compound no. | Chemical Formula |
|---|---|
| A107 | 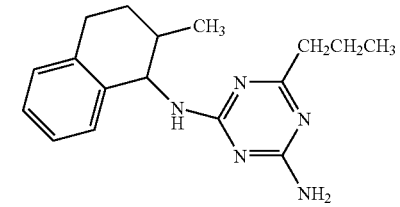 |
| A108 | 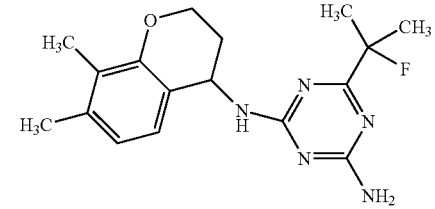 [SMILES: Cc1ccc2c(c1C)OCCC2Nc1nc(N)nc(C(C)(C)F)n1] |
| A109 | 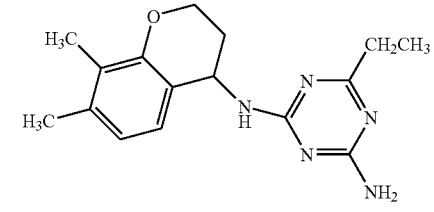 [SMILES: CCc1nc(N)nc(NC2CCOc3c2ccc(C)c3C)n1] |
| A110 | 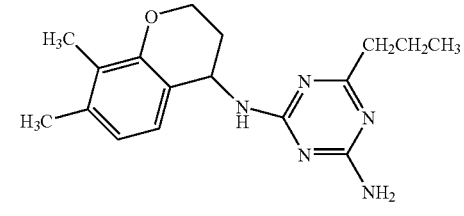 |
| A111 | 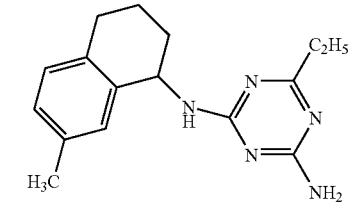 [SMILES: CCc1nc(N)nc(NC2CCCc3ccc(C)cc32)n1] |
| A112 | 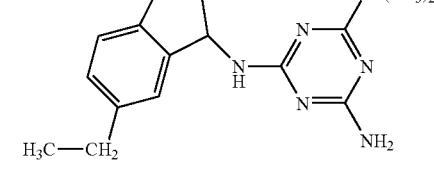 |
| A113 | 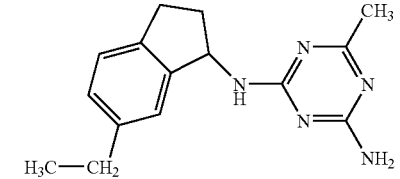 [SMILES: CCc1ccc2c(c1)C(Nc1nc(C)nc(N)n1)CC2] |
| A114 | 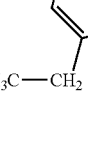 |
| A115 | 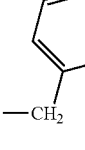 |
| A116 | 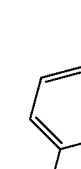 |
| A117 | 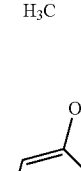 |
| A118 | 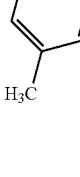 |
| A119 | 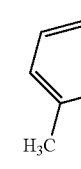 |
| A120 |  |

TABLE 1-continued

Compounds of the formula (I):

| Compound no. | Chemical Formula |
|---|---|
| A121 | (structure) |
| A122 | (structure) |
| A123 | (structure) |
| A124 | (structure) |
| A125 | (structure) |
| A126 | (structure) |
| A127 | (structure) |

Preferred compounds are compounds of formula (I) in which the 2,4-diamino-s-triazin moiety is N-substituted with an optionally substituted indanyl group, optionally substituted tetrahydronaphthyl group or optionally substituted 4-chromanyl group.

More preferred are compounds of this type from table 1, specifically the compounds from table 1 having the number (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (A41), (A42), (A43), (A44), (A53), (A54), (A55), (A56), (A63), (A65), (A66), (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) and mixtures and/or salts thereof.

Preferred compounds are also compounds of formula (I) in which the 2,4-diamino-s-triazin moiety is N-substituted with an optionally substituted indanyl group, optionally substituted tetrahydronaphthyl group or optionally substituted 4-chromanyl group. More preferred are compounds of this type from table 1, specifically the compounds from (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (A41), (A42), (A43), (A44), (A53), (A54), (A55), (A56), (A63), (A65), (A66), (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) and mixtures thereof.

Preferred compounds among said group of compounds are optically active, e.g. compound no. (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (41), (A42), (A43), (A44), (A53), (A54), (A55), (A56), (A63), (A65), (A66) or (A69) having an optical purity corresponding to 60 to 100% (R)-isomer or isomers, preferably of from 70 to 100% (R)-isomer(s), more preferably of from 80 to 100% (R)-isomer(s), in each case relative to the total amount the stereoisomer(s) having (R)- and (S)-configuration at the position marked 1 in formula (I).

Preferred are also mixtures of said optically active compounds, for instance the mixtures of compounds (A9)+(A11), (A21)+(A22), (A23)+(A24), (A28)+(A29), (A32)+(A33), wherein the ratios can be varied in a broad range.

Preferred are also racemic mixtures of the said optically active compounds, for instance the racemic compound no. (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) or mixtures thereof.

Preferred is also compound no. (A12), (A14), (A20), (A27), (A40), (A45), (A46), (A47), (A48), (A52), (A62), (A67), (A68), (A78), (A80), (A88), (A99), (A104), (A105), (A106), (A107), (A111), (A116), (A121), (A126), (A127) or a mixture of two or more of said compounds. Concerning racemic mixtures of optical purities the conditions set forth above also are valid for this group of compounds accordingly.

Preferred is also compound no. (A15), (A39), (A49), (A50), (A51), (A57), (A58), (A59), (A60), (A61), (A64), (A81), (A98), (A108), (A109), (A110), (A116), (A117), (A118), (A119), (A120), (A123) or a mixture of two or more of said compounds. Concerning racemic mixtures of optical purities the conditions set forth above also are valid for this group of compounds accordingly.

Optically active compounds (I) and their preparation are described in WO 2004/069814. It is generally possible to use customary methods for optical resolutions (cf. Textbooks of Stereochemistry), for example following processes for separating mixtures into diastereomers, for example physical processes, such as crystallization, chromatographic processes, in particular column chromatography and high pressure liquid chromatography, distillation, if appropriate under reduced pressure, extraction and other processes, it is possible to separate the remaining mixtures of enantiomers, generally by chromatographic separation on chiral solid phases. Suitable for preparative amounts or use on an industrial scale are processes such as the crystallization of diastereomeric salts which can be obtained from the compounds (I) using optically active acids and, if appropriate, provided that acidic groups are present, using optically active bases.

The compounds of the formula (I) and their salts, all termed herein below as compounds of formula (I), have an excellent herbicidal activity against a broad range of economically important monocotyledonous and dicotyledonous harmful plants. The compounds of formula (I) also act efficiently on perennial weeds which produce shoots from rhizomes, root stocks or other perennial organs and which are difficult to control. In this context, the substances can be applied pre-planting, pre-emergence or post-emergence.

The herbicidal compounds (I) mentioned above show an excellent and desirable effect in terms of weed controlling on the lawn or turf without or substantial without injury to the lawn or turf.

The terms "lawn" or "turf" are used in the following for describing more or less the same types of plant species which can be used for generating a high quality lawn or turf. Therefore, when using the term "lawn" only, it defines plant species which can be used for turf as well and vice versa. The term "lawn" or "turf" describes all uses of well maintained grass in golf courses, sports turf like football or soccer places, landscape situations, parks, home and gardens or all other situations were grasses are grown for achieving a well maintained ground cover that is functional for all types of sport activities or for aesthetic purposes.

The herbicidal compounds (I) of the present invention show excellent controlling effect against a wide range of weeds on the lawn and gives no or reduced phytotoxicity to "lawn species" such as *Cynodon* spp, *Pasapalum notatum*, *Zoysia* spp., *Stenotaphrum americanum*, *Axonopus* spp., *Eremochloa optiuroides*, *Pennisetum clandestinum*, *Festuca rubra*, *Festuca arundinacea*, *Agrostis stolonifera*, *Agrostis tenuis*, *Poa pratense*, *Lolium perenne*. Consequently, the compounds (I) can be applied as an excellent, selective herbicide for the lawn.

According to the invention, by "turfgrass" there is understood an annual or perennial Gramineae, said gramineae preferably belongs to one or more of the genera *Agropyron*, *Agrostis*, *Axonopus*, *Bromus*, *Buchloe*, *Cynodon*, *Eremochloa*, *Festuca*, *Lolium*, *Paspulum*, *Pennisetum*, *Phleum*, *Poa*, *Stenotaphrum* or *Zoysia*. More preferably, said gramineae belongs to one or more of the genera *Agrostis*, *Buchloe*, *Cynodon*, *Eremochloa*, *Festuca*, *Lolium*, *Paspulum*, *Pennisetum*, *Poa*, *Stenotaphrum* or *Zoysia*.

According to the invention by "turf" is understood as a group of turfgrass, which covers a surface area of ground and is subject to regular maintenance.

The present invention can be practiced with all turfgrasses including there varieties and hybrids, including cool season turfgrass and warm season turfgrass.

Examples of cool season turfgrasses are: Bluegrasses (*Poa* L.), such as Kentucky Bluegrass (*Poa pratensis* L.), Rough Bluegrass (*Poa trivialis* L.), Canada Bluegrass (*Poa compressa* L.), *Poa supina* and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.), Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia*), Tal [Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); \A/heatgrasses (*Agropyron* Gaertn.), such as Fairway Wheatgrass (*Agropyron cristatum* (L.) Gaertn.), Western Wheatgrass (*Agropyron smithii* Rydb.). Other cool season turfgrasses include Smooth Brome (*Bromus inermis* Leyss.) and Timothy (*Phleum* L.).

Examples of warm season turfgrasses are Bermudagrasses (*Cynodon* L. C. Rich), Zoysiagrasses (*Zoysia* Willd.), St. Augustinegrass (*Stenotaphrum secundatum* (Watt.) Kuntze), Centipedegrass (*Eremochloa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.) and Seashore *paspalum* (*Paspalum vaginatum* swartz).

The herbicidal compounds (I) of the present invention can be used for controlling various kinds of weeds developing on the lawn or turf.

As examples of the weeds to be controlled there can be mentioned the following: Monocotyledonous weeds such as: *Digitaria ciliayis* (Retz.) Koeler, *Eleusine indica* (L.) Gaertn., *Digitaria sanguinalis* (L.) Scop. *Setaria viridis* (L.) Beauv. var. *viridis*, *Poa annua* L., *Alopecurus aequalis* Sobol. var. *amurensis*, *Imperata cylindrica* (L.) Beau., *Luzula capitata* (Mig.) Mig, *Cyperus rotundus* L., *Cyperus brevifolius* (Rottb.) Hassk. var. *leiolepis*, *Digitaria radicosa* (Presl) Mig., *Digitaria violascens* Link), *Setaria faberii* Herrm, *Holcus lanatus*, etc.

Dicotyledonous weeds such as: *Rumex japonicus* Houtt., *Portulaca oleracea* L. var. *oleracea*, *Stellaria neglecta* Weihe, *Kummerowia striata* (Thunb. ex Murray) Schindl., *Euphorbia supina* Rafin, *Galinsoga ciliata* (Rafin.) Blake, *Cerastium glomeratum* Thuill., *Stellaria alsine* Grimm. var. *undulata* (Thunb. ex Murray) Ohwi, *Cardamine flexuosa* With., *Capsella bursa-pastoris* Medicus, *Lamium amplexicaule* L., *Veronica persica* Poir., *Veronica filiformis*, *Aster maaekii* Regel, *Oxalis corniculata* L., *Hydrocotyle sibthorpioides* Lam., *Plantago asiatica* L., *Plantago lanceolata* L., *Plantago media*, *Plantago major*, *Artemisia indica* Willd. var. *maximowiczii* (Nakai) Hara, *Erigeron philadelphicus* L., *Rumex acetosa* L., *Taraxacum officinale* Weber, *Bellis perennis*, *Achilea millefolia*, *Crepis capillaris*, *Prunella vulgaris*, *Ranunculus repens*, *Ranunculus acris*, *Trifolium repens*, *Trifolium dubium*, *Potentilla* spp. etc.

The use of the herbicidal compounds (I), however, should not be restricted to these weeds in any way, but can be applied against other weeds in the same manner.

If the compounds according to the invention are applied to the soil surface before germination (pre-emergence of the weeds), then the weed seedlings are either prevented completely from emerging or the weeds grow until they have reached the cotyledon stage, but then their growth stops and they finally die completely after three to four weeks have elapsed.

When the active substances are applied post-emergence to the green parts of the plants, growth stops over time after treatment and the weed plants remain at the stage of growth at the time of application, or they die completely after a certain time, so that in this manner competition by the weeds, which is harmful to the lawn or turfgrass, is eliminated at a very early stage and in a sustained manner.

Although the compounds according to the invention have an excellent herbicidal activity against mono- and dicotyledonous weeds, important plant varieties for lawn and turf are not damaged at appropriate dosages when applied before or, preferably, after emergence of the turfgrasses or when applied on established turf or lawn. "Established turf or lawn" means dormant turf or actively growing turf grass. "Dormant turf" means a turf already grown and emerged but not actively growing due to cold weather conditions, e.g. turf between the vegetation periods.

For these reasons, the present compounds are suitable for the selective control of undesired vegetation on lawn or turf or the soil where the lawn or turf is grown.

The activity allows to apply the compounds as effective herbicidal active ingredients pre- and post-emergence, related to the emergence of the weeds, for controlling broadleaved weeds and grass weeds as a selective herbicide. Preferably the compounds (I) are applied to the locus of the weed plants and lawn or turf plants pre-plant or pre-emergence of the lawn or turf. More preferred is the application of compounds (I) for weed control on established turf. Preferably the compounds (I) are applied pre-emergence for the growth the weeds.

The term "locus" of a plant or plants comprises the plant or plants, part of the plants, seed of the plants or the area where the plants are growing. Such plants can be weed plants or the plants of lawn or turf or both types of plants. Particularly, the "locus of turfgrass" as used herein is intended to embrace the place on which the turfgrass are growing, the place where the seeds of the turfgrass are sown or the place where the seeds of the turfgrass will be placed for subsequent plant growth. According to the invention, the "locus of a turf" can relate to soil or to a substrate. An example for such a locus is a golf course, on which turfgrass is managed.

According to the invention the term "soil" means natural soil, which is typically present on a land area, such as soil being present on a golf course, or means soil, that has been modified, such as soil being granulated and/or treated with agrochemicals, such as for example fertilizers.

According to the invention the term "substrate" means a medium for the growth of turfgrass and the like, suited for application to a variety of existing ground structures. Typically, such mediums are soil-free mixtures that include sufficient proportions of ingredients of elastomeric granules, suitable binding emulsion, mineral aggregate, filier and controlled release plant nutrient particles, so that when laid and cured, said mixture produces a water permeable, resilent substrate having air pockets through which a root system of turfgrass can penetrate. Turfgrass growing on said substrate can form a turf, which can be applied to non-porous surfaces, such as for example roofs of buildings, terraces and other hard surface areas, or to porous surfaces, such as for example football fields or golf courses. Elastomeric granules can be, for example, granules of rubber, granules of recycled vehicle tyre rubber or mixtures thereof.

The compounds (I) according to the invention are generally applied to the weed and turfgrass plants or seed thereof by treating the locus thereof with an agricultural composition comprising one or more compounds (I) or salts thereof.

The amount of compounds (I) to be applied will depend on various factors, such as the subject of the treatment, such as, plants or soil, the type of treatment, such as, for example spraying or spreading, the purpose of the treatment, such as, for example preventive or curative, the application time, environmental conditions or turfgrass species.

The compounds (I) according to the invention can be applied to the locus of the lawn or turf with a composition ("composition according to the invention") comprising one or more compounds (I) or salts thereof. Within said embodiment of the invention, the compounds (I) or compositions according to the invention are preferably applied to the locus of the lawn or turf by spraying or drenching liquid (sprayable) formulations or dissolvable or dispersing formulations. Spray and drench application with water volumes from 50 to 10000 liter per hectare can be applied with all common application equipment like large motor driven professional spray equipment, knapsack sprayer, hose end applicators, RTU pump sprayers, aerosol cans, ULV applicators or watering cans.

Furthermore the herbicidal compounds (I) can be applied by spreading or granular (active ingredient on inert or active ingredient on fertilizer) formulations It is also possible to water in the product after applications with additional irrigations for all application methods.

In one embodiment, the compositions are applied to the (locus of the) weed plants and turfgrass as a sprayable liquid formulation. In another embodiment, the compositions are applied to the (locus of the) weed plants and turfgrass as a granular formulation. Suitable granules include inert and fertilizer granules. The active ingredient may be dispersed throughout, impregnated into, or coated on the surface of the granules.

Treatment of turfgrass may be performed by lawn care operators, greenkeepers or home owners.

To maintain high quality, healthy turfgrass on the intended surface area of ground, such as for example, a golf course, a sports field, a park area or a home lawn, and to protect said turfgrass against weed plants, the compositions according to the invention are applied to the turf once or more than once during maintenance of the turfgrass.

Preferably, the compositions according to the invention are applied to the turfgrass once or more than once during a growing season of the turfgrass.

The composition according to the invention may be applied to the locus of the turfgrass before ("preventive treatment") or after emergence of the weeds ("curative treatment").

For example, the compositions according to the invention can be applied to the soil before or after the seeds of the turfgrass are sown or placed into the soil; or the compositions according to the invention can be applied to a substrate for the growth of turfgrass before or after the seeds of the turfgrass are placed into the substrate; or the compostions according to the invention can be applied to the soil before turfgrass grown on a substrate are placed on top of the soil together with the substrate.

With the composition according to the invention it is possible to inhibit or destroy the weed plants which occur on turfgrass, while the parts of turfgrass existing or which grow later are not substantially damaged.

The application rates for the herbicidal compounds of formula (I) or salts thereof can vary within a broad range and generally depend on the weed spectrum to be controlled, the soil type and weather conditions or whether the compounds are combined with other herbicidal active ingredients. Suitable applications rates generally are within the range of from 0.01 to 2000 g active ingredient (=compounds (I)) per hectare (a.i./ha), preferably of from 0.5 to 500 g a.i./ha, more preferably 1 bis 250 g a.i./ha It is also possible to use the compounds (I) in combination with other pesticidally active substances or nutrients, such as, for example, insecticides, acaricides, herbicides, fungicides, safeners, fertilizers and/or growth regulators.

The invention thus also relates to a method of controlling weeds in lawn or turf which comprises applying one or more type (A) herbicides, optionally together, before or after the treatment with one or more other active ingredients selected from the group consisting of type (B) herbicides and other type (C) active ingredients useful in the treatment of lawn or turf, to the weeds, parts of the weed plants, seeds of the weed plants or the area under cultivation where the plants of lawn or turf are growing or to be sown.

Type (A) herbicides are the compounds of formula (I) or their salts.

Type (B) herbicides are other herbicides useful to be combined with compounds (I) for the purpose of broadening weed spectrum to be controlled, or increasing herbicidal effect (some possible type B herbicides are mentioned further below).

Type (C) active ingredients useful in the treatment of lawn or turf can be, for instance, insecticides, acaricides, fungicides, safeners, fertilizers and/or growth regulators or nutrients useful for treating lawn or turf against phytopathogenic diseases or for growth regulation or growth promotion of lawn or turf.

Type (B) herbicides are other herbicides useful to be combined with compounds (I) for the purpose of broadening weed spectrum to be controlled, or increasing herbicidal effect (some possible type B herbicides are mentioned further below).

Possible combination partners for the inventive active ingredients, in mixed formulations or in a tankmix, are, for example, known active ingredients which are based on inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other usable compounds, with a mechanism of action that is, in some cases, unknown or different, are described, for example, in Weed Research 26, 441-445 (1986), or "The Pesticide Manual", 14th edition 2006/2007, published by the British Crop Protection Council (hereinafter also abbreviated to "PM"), "The e-Pesticide Manual", version 4.0 2006/2007, published by the British Crop Protection Council and literature cited there, "Compendium of Pesticide Common Names" available from the internet (http://www.alanwood.net/pesticides/).

Herbicides, plant growth regulators and herbicide safeners, which are known from the literature and which can be combined with the compounds of the formula (I), include, for example, the following active ingredients (note: the compounds are either referred to by the common name in accordance with the International Organization for Standardization (ISO) or by the chemical name, if appropriate together with a customary code number):

acetochlor; acibenzolar; acibenzolar-S-methyl; acifluorfen; acifluorfen-sodium; aclonifen; alachlor; allidochlor; alloxydim; alloxydim-sodium; ametryn; amicarbazone; amidochlor, amidosulfuron; aminocyclopyrachlor, aminopyralid; amitrole; ammoniumsulfamate; ancymidol; anilofos; asulam; atrazine; azafenidin, azimsulfuron; aziprotryn; BAH-043; BAS-140H, BAS-693H; BAS-714H; BAS-762H; BAS-776H; beflubutamid, benazolin; benazolin-ethyl; bencarbazone; benfluralin; benfuresate; benoxacor; bensulfuron; bensulfuron-methyl; bensulide; bentazone; benzfendizone, benzobicyclon, benzofenap; benzofluor; benzoylprop; benzoylprop-ethyl; bialaphos; bifenox; bilanafos (bialaphos); bilanafos-sodium; bispyribac; bispyribac-sodium, bromacil; bromobutide; bromofenoxim; bromoxynil; bromuron; buminafos; busoxinone; butachlor; butafenacil, butamifos; butenachlor; butralin; butroxydim, butylate; cafenstrole; carbetamide; carfentrazone; carfentrazone-ethyl; chlomethoxyfen; chloramben; chlorazifop; chlorazifop-butyl; chlorbromuron; chlorbufam; chlorfenac; chlorfenac-sodium; chlorfenprop; chlorflurenol; chlorflurenol-methyl; chloridazon; chlorimuron; chlorimuron-ethyl; chlormequat-chloride; chlornitrofen; chlorphthalim; chlorthal-dimethyl; chlorotoluron; chlorpropham; chlorsulfuron; chlorthal-dimethyl; chlorthiamid; chlortoluron, cinidon; cinidon-ethyl, cinmethylin; cinosulfuron; clethodim; clodinafop; clodinafop-propargyl; clofencet; clomazone; clomeprop; cloprop; clopyralid; clopyrasulfuron; clopyrasulfuron-methyl; cloquintocet; cloquintocet-mexyl; cloransulam; cloransulam-methyl, CMA, cumyluron; cyanamide, cyanazine; cyclanilide; cycloate; cyclosulfamuron; cycloxydim; cycluron; cyhalofop; cyhalofop-butyl; cyperquat; cyprazine; cyprazole; cyprosulfamide; 2,4-D; 2,4-DB; daimuron (dymron); dalapon; daminozide; dazomet; n-decanol; desmedipham; desmetryn; detosylpyrazolate (DTP); di-allate; dicamba; dichlobenil; dichlormid; dichlorprop; dichlorprop-P; diclofop; diclofop-methyl; diclofop-P; diclofop-P-methyl; diclosulam, diethatyl; diethatyl-ethyl; difenoxuron; difenzoquat; diflufenican; diflufenzopyr; diflufenzopyr-sodium; dikegulac-sodium; dimefuron; dimepiperate, dimethachlor; dimethametryn; dimethazone; dimethenamid; dimethenamid-P; dimethipin; dimetrasulfuron; dimexyflam; dinitramine; dinoseb; dinoterb; diphenamid; dipropetryn; diquat; diquat-dibromide; dithiopyr; diuron; DNOC; DSMA, eglinazine-ethyl; endothal; epoprodan, EPTC; esprocarb; ethalfluralin; ethametsulfuron-methyl; ethephon, ethidimuron; ethiozin; ethofumesate; ethoxyfen; ethoxyfen-ethyl; ethoxysulfuron, etobenzanid; F5231, i.e. N-[2-chloro-4-fluoro-5-[4-(3-fluoropropyl)-4,5-dihydro-5-oxo-1H-tetrazol-1-yl]phenyl] ethanesulfonamide; fenchlorazole(-ethyl), fenclorim; fenoprop; fenoxan; fenoxaprop; fenoxaprop-ethyl; fenoxaprop-P; fenoxaprop-P-ethyl; fenoxydim; fentrazamide, fenuron; flamprop; flamprop-methyl; flamprop-M-isopropyl; flamprop-M-methyl; flazasulfuron; floazulate, florasulam, fluazifop; fluazifop-butyl; fluazifop-P; fluazifop-P-butyl; fluazolate; flucarbazone; flucarbazone-sodium, flucetosulfuron, fluchloralin; flufenacet (thiafluamide, fluthiamide); flufenpyr; flufenpyr-ethyl; flumetralin, flumetsulam; flumiclorac; flumiclorac-pentyl, flumioxazin; flumipropyn; fluometuron, fluorochloridone, fluorodifen; fluoroglycofen; fluoroglycofen-ethyl; flupoxam; flupropacil; flupropanate; flupyrsulfuron; flupyrsulfuron-methyl-sodium; flurazole; flurenol; flurenol-butyl; fluridone; fluorochloridone; fluoroxypyr; fluoroxypyr-meptyl; flurprimidol, flurtamone; fluthiacet; fluthiacet-methyl; fluthiamide; fluxofenim; fomesafen; foramsulfuron; forchlorfenuron, fosamine; furilazole, furyloxyfen; gibberillic acid; glufosinate; glufosinate-ammonium; glufosinate-P; glufosinate-P-ammonium; glufosinate-sodium; glufosinate-P-sodium; glyphosate; glyphosate-isopropylammonium; H-9201; halosafen; halosulfuron; halosulfuron-methyl; haloxyfop; haloxyfop-P; haloxyfop-ethoxyethyl; haloxyfop-P-ethoxyethyl; haloxyfop-methyl; haloxyfop-P-methyl; HC-252, hexazinone; HNPC-9908; HW-02; imazamethabenz; imazamethabenz-methyl; imazamox, imazapic, imazapyr; imazaquin; imazamethapyr, imazethapyr; imazosulfuron; inabenfide, indanofan, indole- 3-ylacetic acid (IAA), 4-indol-3-ylbutyric acid (IBA); iodosulfuron; iodosulfuron-methyl-sodium; ioxynil; ipfencarbazone; isocarbamid; isopropalin; isoproturon; isouron; isoxaben; isoxachlortole; isoxadifen; isoxadifen-ethyl; isoxaflutole, isoxapyrifop; KUH-043; KUH-071; karbutilate; ketospiradox; lactofen; lenacil; linuron; maleic hydrazide, MCPA; MCPB; MCPB-methyl, -ethyl, and -sodium; mecoprop; mecoprop-sodium; mecoprop-butotyl; mecoprop-P; mecoprop-P-butotyl; mecoprop-P-dimethylammonium; mecoprop-P-2-ethylhexyl; mecoprop-P-potassium; mefenacet; mefenpyr; mefenpyr-diethyl; mefluidide; mepiquat-chloride; mesosulfuron; mesosulfuron-methyl; mesotrione; metam, metamifop, metamitron; metazachlor; methabenzthiazuron; methazole; methoxyphenone; 1-methylcyclopropene; methyldymron; methyl isothiocyanate; metobenzuron, metobromuron; metolachlor; S-metolachlor; metosulam; metoxuron; metribuzin; metsulfuron; metsulfuron-methyl; molinate; monalide; monocarbamide; monocarbamide dihydrogensulfate; monolinuron; monuron; MT 128, i.e. 6-chloro-N-(3-chloro-2-propenyl)-5-methyl-N-phenyl-3-pyridazinamine; MSMA, MT 5950, i.e. N-[3-chloro-4-(1-methylethyl)phenyl]-2-methylpentanamide; 2-(1-naphthyl)acetamide, 1-naphthylacetic acid; 2-naphthyloxyacetic acid; NGGC-011; naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrophenolate-sodium (isomer mixture); nitrofluorfen; nonanoic acid; norflurazon; orbencarb; orthasulfamuron; oryzalin; oxabetrinil; oxadiargyl; oxadiazon; oxasulfuron; oxaziclomefone; oxyfluorfen; paclobutrazol; paraquat; paraquat-dichloride; pebulate; pelargonic acid; pendimethalin; pendralin; penoxsulam; pentachlorophenol; pentanochlor; pentoxazone; perfluidone; pethoxamid, phenisopham; phenmedipham; phenmedipham-ethyl; picloram; picolinafen, pinoxaden, piperophos; piributicarb; pirifenop; pirifenop-butyl; pretilachlor; primisulfuron; primisulfuron-methyl; probenazole; procyazine; prodiamine; profluralin; profoxydim; prohexadione; prohexadione-calcium, prohydrojasmon; prometon; prometryn; propachlor; propanil; propaquizafop; propazine; propham; propisochlor; propoxycarbazone; propoxycarbazone-sodium; n-propyl dihydrojasmonate; propyzamide; prosulfalin; prosulfocarb; prosulfuron; prynachlor; pyraclonil; pyraflufen; pyraflufen-ethyl; pyrasulfotole; pyrazolynate (pyrazolate); pyrazosulfuron; pyrazosulfuron-ethyl; pyrazoxyfen; pyribambenz; pyribambenz-isopropyl; pyribenzoxim; pyributicarb; pyridafol; pyridate; pyriftalid; pyriminobac; pyriminobac-methyl; pyrimisulfan, pyrithiobac; pyrithiobac-methyl; pyrithiobac-sodium (KIH-2031); pyroxasulfone; pyroxsulam; quinclorac; quinmerac; quinoclamine; quinofop and its ester derivatives; quizalofop; quizalofop-ethyl; quizalofop-P; quizalofop-P-ethyl; quizalofop-P-tefuryl; renriduron; rimsulfuron; saflufenacil; secbumeton; sethoxydim; siduron; simazine; simetryn; sintofen; SN 106279, i.e. 2-[[7-[2-chloro-4-(trifluoromethyl)phenoxy]-2-naphthalenyl]oxy]propanoic acid and its methyl ester; sulcotrione; sulfallate (CDEC); sulfentrazone; sulfazuron; sulfometuron; sulfometuron-methyl; sulfosate (glyphosate-trimesium); sulfosulfuron; SYN-449; SYN-523; SYP-249; SYP-298; SYP-300; 2,3,6-TBA; TCA; tebutam; tebuthiuron; tecnazene; tefuryltrione; tembotrione; tepraloxydim; terbacil; terbucarb; terbuchlor; terbumeton; terbuthylazine; terbutryn; TH 547; thenylchlor; thiafluamide; thiazafluoron; thiazopyr; thidiazimin; thidiazuron; thiencarbazone; thiencarbazone-methyl; thifensulfuron; thifensulfuron-methyl; thiobencarb; TI-35; tiocarbazil; topramezone; tralkoxydim; tri-allate; triasulfuron; triaziflam; triazofenamide; tribenuron; tribenuron-methyl; trichloroacetic acid (TCA); triclopyr; tridiphane; trietazine; trifloxysulfuron; trifloxysulfuron-sodium; trifluralin; triflusulfuron; triflusulfuron-methyl; trimeturon; trinexapac; trinexapac-ethyl; tritosulfuron; tsitodef; uniconazole; uniconazole-P; vernolate; ZJ-0166; ZJ-0270; ZJ-0862; and the following compounds (see chemical formulae below):

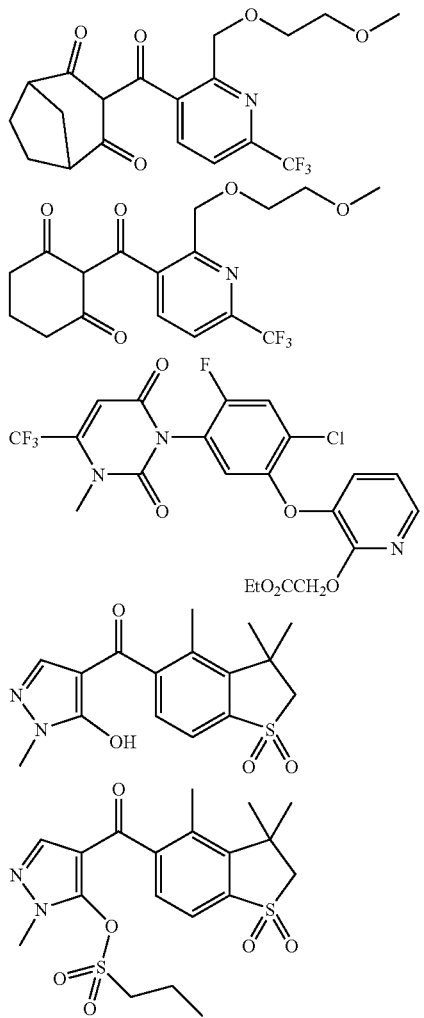

Preferred are the herbicide combinations (A)+(B) comprising one or more of the compounds of formula (I) or salt thereof (=herbicides (A)) with herbicides (B) selected from the group consisting of, for example, the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives, such as quinolyloxy-, quinoxalyloxy-, pyridyloxy-, benzoxazolyloxy- and benzothiazolyloxyphenoxyalkanecarboxylic acid esters, cyclohexanedione oximes, benzoylcyclohexanediones, benzoylisoxazoles, benzoylpyrazoles, imidazolinones, pyrimidinyloxypyridinecarboxylic acid derivatives, pyrimidyloxybenzoic acid derivatives, sulfonylureas, sulfonylaminocarbonyltriazolinones, triazolopyrimidinesulfonamide derivatives, phosphinic acid derivatives and salts thereof, glycine derivatives, triazolinones, triazinones and also S—(N-aryl-N-alkylcarbamoylmethyl)dithiophosphoric esters, pyridinecarboxylic acids, pyridines, pyridinecarboxamides, 1,3,5-triazines and others.

Preference is given here to phenoxyphenoxy- and heteroaryloxyphenoxycarboxylic acid esters and salts, cyclohexanedione oximes, benzoylcyclohexanediones, benzoylisoxazoles, benzoylpyrazoles, sulfonylureas, sulfonylaminocarbonyltriazolinones, imidazolinones and mixtures of the active compounds mentioned with one another and/or with active compounds used for broadening the activity spectrum of the herbicides, for example bentazone, cyanazine, atrazine, bromoxynil, dicamba and other leaf-acting herbicides.

Preferred are the herbicide combinations (A)+(B) comprising a compound of the formula (I) or a salt thereof, or one or more of the compounds of formula (I) or salt thereof, with a herbicide (B) or herbicides (B) each selected from the group consisting of:

(B1) 2,4-D and esters and salts thereof,
(B2) Amidosulfuron or salts thereof, such as (B2.1) Amidosulfuron,
(B3) Aminocyclopyrachloror salts or esters thereof, such as (B3.1) Aminocyclopyrachlor, (B3.2) Aminocyclopyrachlor-methyl,
(B4) Aminopyralid or salts thereof, such as (B4.1) Aminopyralid,
(B5) Bromoxynil or esters thereof, such as (B5.1) Bromoxynil, (B5.2) Bromoxynil-heptanoate, (B5.3) Bromoxynil-octanoate,
(B6) Diflufenican,
(B7) Ethofumesate,
(B8) Ethoxysulfuron or salts thereof, such as (B8.1) Ethoxysulfuron, (B8.2) Ethoxysulfuron-sodium,
(B9) Fluoroxypyr or esters thereof, such as (B9.1) Fluoroxypyr, (B9.2) Fluoroxypyr-meptyl, (B9.3) Fluoroxypyr-2-butoxy-1-methylethyl,
(B10) Fatty acids, such as fatty acids having 1 to 16 carbon atom, such as (B10.1) acetic acid, (B10.1) acetic acid, (B10.2) propionic acid, (B10.3) butanoic acid, (B10.4) pentanoic acid, (B10.5) hexanoic acid, (B10.6) heptanoic acid, (B10.7) octanoic acid, (B10.8) nonanoic acid, (B10.9) decanoic acid, (B10.10) undecanoic acid, (B10.11) dodecanoic acid, preferably $C_8$-$C_{12}$-fatty acids, more preferably (B10.8) nonanoic acid and (B10.9) decanoic acid,
(B11) Glufosinate or salts thereof, such as (B11.1) Glufosinate, (B11.2) Glufosinate-ammonium, (B11.3) Glufosinate-sodium,
(B12) Glufosinate-P (=L-Glufosinate or phosphinothricin) or salts thereof, such as (B12.1) Glufosinate-P, (B12.2) Glufosinate-P-sodium, (B12.3) Glufosinate-P-ammonium,
(B13) Glyphosate or salts thereof, such as (B13.1) Glyphosate, (B13.2) Glyphosate-sodium, (B13.3) Glyphosate-potassium, (B13.4) Glyphosate-ammonium, (B13.5) Glyphosate-diammonium, (B13.6) Glyphosate-isopropylammonium,
(B14) Iodosulfuron and esters and salts thereof, such as (B14.1) Iodosulfuron, (B14.2) Iodosulfuron-methyl, (B14.3) Iodosulfuron-methyl-sodium,
(B15) Mesosulfuron and esters or salts thereof, such as (B15.1) Mesosulfuron, (B15.2) Mesosulfuron-methyl,
(B16) Metosulam,
(B17) Paraquat and salts thereof, such as (B17.1) Paraquat-dichloride,
(B18) Penoxsulam and salts thereof, such as (B18.1) Penoxsulam,
(B19) Picloram and esters and salts thereof, such as (B19.1) Picloram, (B19.2) Picloram-potassium, (B19.3) Picloram-dimethylammonium, (B19.4) Picloram-triisopropylammonium, (B19.5) Picloram-triethanolammonium, (B19.6) Picloram-triisopropanolammonium, (B19.7) Picloram-isooctyl,
(B20) Pyrasulfotole and salts thereof, such as (B20.1) Pyrasulfotole,
(B21) Pyroxasulfone (KIH-485) and salts thereof, such as (B21.1) Pyroxasulfone,
(B22) Pyroxsulam and salts thereof, such as (B22.1) Pyroxulam,
(B23) Rimsulfuron and salts thereof, such as (B23.1) Rimsulfuron,
(B24) Saflufenacil and salts thereof, such as (B24.1) Saflufenacil,
(B25) *Sclerotinia* (biological herbicides),
(B26) SYN-449 and salts thereof, such as (B26.1) SYN-449, i.e. 4-Hydroxy-3-[[2-[(2-methoxy-ethoxy)-methyl]-6-trifluoromethyl-3-pyridinyl]-carbonyl]-bicyclo[3.2.1]oct-3-en-2-on,
(B27) SYN-523 and salts thereof, such as (B27.1) SYN-523, i.e. [[3-[2-Chlor-5-[3,6-dihydro-3-methyl-2,6-dioxo-4-(trifluormethyl)-1(2H)-pyrimidinyl]-4-fluorphenoxy]-2-pyridinyl]oxy]-essigsaureethylester,
(B28) Tembotrione and salts thereof, such as (B28.1) Tembotrione,
(B29) Thiencarbazone and esters and salts thereof, such as (B29.1) Thiencarbazone, (B29.2) Thiencarbazone-methyl, (B29.3) Thiencarbazone-methyl-sodium,
(B30) Thifensulfuron and esters and salts thereof, such as (B30.1) Thifensulfuron, (B30.2) Thifensulfuron-methyl, (B30.3) Thifensulfuron-methyl-sodium,
(B31) Tribenuron and esters and salts thereof, such as (B31.1) Tribenuron, (B31.2) Tribenuron-methyl, (B31.3) Tribenuron-methyl-sodium,
(B32) Trifloxysulfuron and salts thereof, such as (B32.1) Trifloxysulfuron, (B32.2) Trifloxysulfuron-sodium,
(B33) Dicamba and esters and salts thereof, such as (33.1) Dicamba, (33.2) Dicamba-sodium, (33.3) Dicamba-potassium, (33.4) Dicamba-dimethylammonium, (33.5) Dicamba-isopropylammonium, (33.5) Dicamba-diglycolamin salt, (33.4) Dicamba-butotyl,
(B34) Mecoprop and Mecoprop-P, and esters and salts thereof, such as (34.1) Mecoprop and esters and salts thereof, (34.2) Mecoprop-P and esters and salts thereof. (34.3) Mecoprop, (34.4) Mecoprop-P, (34.5) Mecoprop-sodium, (34.6) Mecoprop-butotyl, (34.7) Mecoprop-P, (34.8) Mecoprop-P-sodium, (34.9) Mecoprop-P-potassium, (34.10) Mecoprop-P-butotyl, (34.11) Mecoprop-P-2-ethyl-hexyl,
(B35) MCPA and esters and salts thereof, such as (35.1) MCPA, (35.2) MCPA-sodium, (35.3) MCPA-potassium, (35.4) MCPA-dimethylammonium, (35.5) Mecoprop-P-2-ethyl-hexyl,
(B36) Fenoxapropand esters and salts thereof, such as (36.1) Fenoxaprop, (36.2) Fenoxaprop-ethyl,
(B37) Fenoxaprop-P, and esters and salts thereof, such as (36.1) Fenoxaprop-P, (37.2) Fenoxaprop-P-ethyl,
(B38) Carfentrazone, and esters and salts thereof, such as (38.1) Carfentrazone, (38.2) Carfentrazone-ethyl,
(B39) Sulfentrazone and salts thereof, such as (39.1) Sulfentrazone,
(B40) Oxadiazon and salts thereof, such as (40.1) Oxadiazon,
(B41) Metsulfuron and esters and salts thereof, such as (41.1) Metsulfuron, (41.2) Metsulfuron-methyl,
(B42) Triclopyr and esters and salts thereof, such as (42.1) Triclopyr, (43.2) Triclopyr-triethylammonium, (42.3) Triclopyr-butotyl, (B43) Foramsulfuron or salts thereof, such as (43.1) Foramsulfuron, and
(B44) Metribuzin or salts thereof, preferably Metribuzin (B44.1).

Some of said compounds belong to the same structural type or same type of mode of action or both. In such cases herbicidal properties of combinations (A) with other herbicides (B) are similar if these herbicides belong to the same structural type and/or mode of action compared with the herbicidal combinations (A)+(B) specifically mentioned above and below.

Salts are generally agriculturally applicable salts, preferably metal salts such as alkaline metal salts, or optionally substituted ammonium salts, such as ammonium salts, mono-, di- or tri-alkyl or -hydroxyalkylammonium salts.

The combination herbicides are described in the references mentioned above (Pesticide Manual etc.); other references are provided in the following:
(B3) Aminocyclopyrachlor and salts thereof, preferably (B3.1) Aminocyclopyrachlor, i.e. 6-amino-5-chlor-2-cyclopropyl-pyrimidin-4-carboxylic acid [CAS-Reg. 858958-08-8];
(B18) Penoxsulam and salts thereof, preferably (B18.1) Penoxsulam, i.e. 2-(2,2-difluoroethoxy)-N-(5,8-dimethoxy[1,2,4]triazolo[1,5-c]pyrimidin-2-yl)-6-(trifluormethyl)benzolsulfonamid [CAS-Reg. 219714-96-2];
(B20) Pyrasulfotole and salts thereof, preferably (B20.1) (5-hydroxy-1,3-dimethyl-1H-pyrazol-4-yl)-[2-(methylsulfonyl)-4-(trifluoromethyl)-phenyl]-methanone [CAS-Reg. 365400-11-9];
(B21) Pyroxasulfone (KIH-485) and salts thereof, preferably (B21.1) Pyroxasulfone, i.e. 3-[5-(difluoromethoxy)-1-methyl-3-(trifluoromethyl)pyrazol-4-ylmethylsulfonyl]-4,5-dihydro-5,5-dimethyl-1,2-oxazol [CAS-Reg. 447399-55-5];
(B22) Pyroxsulam and salts thereof, preferably (22.1) Pyroxsulam, i.e. N-(5,7-dimethoxy[1,2,4]triazolo[1,5-a]pyrimidin-2-yl)-2-methoxy-4-(trifluormethyl)pyridin-3-sulfonamide [CAS-Reg. 422556-08-9];
(B24) Saflufenacil and salts thereof, preferably (B24.1) Saflufenacil (BAS-H800), i.e. 2-chloro-5-[3,6-dihydro-3-methyl-2,6-dioxo-4-(trifluoromethyl)-1(2H)-pyrimidinyl]-4-fluoro-N-[[methyl(1-methylethyl)amino]-sulfonyl]-benzamide [CAS-Reg. 372137-35-4] (WO 2001/083459);
(B26), preferably (B26.1) SYN-449, i.e. 4-hydroxy-3-[[2-[(2-methoxy-ethoxy)-methyl]-6-trifluoromethyl-3-pyridinyl]-carbonyl]-bicyclo[3.2.1]oct-3-en-2-one (CAS RN 352010-68-5, is known from WO-A-2006/097322, WO-A-01/94339;
(B27), preferably (B27.1), SYN-523 is known from WO 2006/061562, EP 1122244;
(B28) Tembotrione and salt thereof are known from WO-A-00/21924, preferably (B28.1) Tembotrione, i.e. 2-{2-chloro-4-mesyl-3-[(2,2,2-trifluorethoxy)methyl]-benzoyl}-cyclohexan-1,3-dion [CAS-Reg. 335104-84-2];
(B29) Thiencarbazone and salts thereof are known from WO 01/05788, preferably (B29.1) Thiencarbazone, i.e. 4-[(4,5-dihydro-3-methoxy-4-methyl-5-oxo-1H-1,2,4-triazol-1-yl)-carbonyl-sulfamoyl]-5-methylthiophen-3-carbonic acid, more preferably (B29.2) Thiencarbazone-methyl, i.e. the methyl ester thereof [CAS-Reg. 317815-83-1] or (B29.3) Thiencarbazone-methyl-sodium, i.e. the sodium salt of (B29.2).

Preferred are combinations of a compound (A) selected from the list of compounds of table 1 (compounds A1 to A127) and a herbicide (B) as follows:
(A)+(B1), (A)+(B2), (A)+(B2.1), (A)+(B3), (A)+(B3.1), (A)+(B3.2), (A)+(B4), (A)+(B4.1), (A)+(B5), (A)+(B5.1), (A)+(B5.2), (A)+(B5.3), (A)+(B6), (A)+(B7), (A)+(B8), (A)+(B8.1), (A)+(B8.2), (A)+(B9), (A)+(B9.1), (A)+(B9.2), (A)+(B9.3), (A)+(B10), (A)+(B10.1), (A)+(B10.7), (A)+(B10.8), (A)+(B10.9), (A)+(B10.10), (A)+(B1011), (A)+(B11), (A)+(B11.1), (A)+(B11.2), (A)+(B11.3), (A)+(B12), (A)+(B12.1), (A)+(B12.2), (A)+(B12.3), (A)+(B13), (A)+(B13.1), (A)+(B13.2), (A)+(B13.3), (A)+(B13.4), (A)+(B13.5), (A)+(B13.6), (A)+(B14), (A)+(B14.1), (A)+(B14.2), (A)+(B14.3), (A)+(B15), (A)+(B15.1), (A)+(B15.2), (A)+(B16), (A)+(B17), (A)+(B17.1), (A)+(B18), (A)+(B18.1), (A)+(B19), (A)+(B19), (A)+(B19.1), (A)+(B19.2), (A)+(B19.3), (A)+(B19.4), (A)+(B19.5), (A)+(B19.6), (A)+(B19.7), (A)+(B20), (A)+(B20.1), (A)+(B21), (A)+(B21.1), (A)+(B22), (A)+(B22.1), (A)+(B23), (A)+(B23.1), (A)+(B24), (A)+(B24.1); (A)+(B25), (A)+(B26), (A)+(B26.1), (A)+(B27), (A)+(B27.1), (A)+(B28), (A)+(B28.1), (A)+(B29), (A)+(B29.1), (A)+(B29.2), (A)+(B29.3), (A)+(B30), (A)+(B30.1), (A)+(B30.2), (A)+(B30.3), (A)+(B31), (A)+(B31.1), (A)+(B31.2), (A)+(B31.3), (A)+(B32), (A)+(B32.1), (A)+(B32.2), (A)+(B33), (A)+(B34), (A)+(B34.1), (A)+(B34.2), (A)+(B35), (A)+(B36), (A)+(B36.1), (A)+(B36.2), (A)+(B37), (A)+(B37.1), (A)+(B37.2), (A)+(B38), (A)+(B38.1), (A)+(B38.2), (A)+(B39), (A)+(B39.1), (A)+(B40), (A)+(B40.1), (A)+(B41), (A)+(B41.1), (A)+(B41.2), (A)+(B42), (A)+(B42.1), (A)+(B42.2), (A)+(B42.3), (A)+(B43), (A)+(B43.1), (A)+(B44) or (A)+(B44.1).

Preferred combinations (A)+(B) are selected from the above combinations wherein (A) is a compound from table 1 having the number (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (A41), (A42), (A43), (A44), (A53), (A54), (A55), (A56), (A63), (A65), (A66), (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A115), (A122), (A124), (A125) and mixtures and/or salts thereof.

Preferred combinations (A)+(B) are selected from the above combinations wherein (A) is a compound from table 1 having the number (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (A41), (A42), (A43), (A44), (A53), (A54), (A55), (A56), (A63), (A65), (A66), (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A15), (A122), (A124), (A125) and mixtures thereof.

Preferred combinations (A)+(B) are selected from the above combinations wherein (A) is a compound from table 1 having the number (A1), (A2), (A3), (A4), (A5), (A6), (A7), (A8), (A9), (A10), (A11), (A13), (A16), (A17), (A18), (A19), (A21), (A22), (A23), (A24), (A25), (A26), (A28), (A29), (A30), (A31), (A32), (A33), (A34), (A35), (A36), (A37), (A38), (41), (A42), (A43), (A44), (A53), (A54), (A55), (A56), (A63), (A65), (A66) or (A69) having an optical purity corresponding to 60 to 100% (R)-isomer or isomers, preferably of from 70 to 100% (R)-isomer(s), more preferably of from 80 to 100% (R)-isomer(s), in each case relative to the total amount the stereoisomer(s) having (R)- and (S)-configuration at the position marked 1 in formula (I).

Preferred combinations (A)+(B) are selected from the above combinations wherein (A) is a compound mixture of compounds from table 1 having the numbers (A9)+(A11), (A21)+(A22), (A23)+(A24), (A28)+(A29), (A32)+(A33), wherein the ratios can be varied in a broad range.

Preferred combinations (A)+(B) are selected from the above combinations wherein (A) is a racemic compound from table 1 having the number (A69), (A70), (A71), (A72), (A73), (A74), (A75), (A76), (A77), (A79), (A82), (A83), (A84), (A85), (A86), (A87), (A89), (A90), (A91), (A92), (A93), (A94), (A95), (A96), (A97), (A100), (A101), (A102), (A103), (A112), (A113), (A114), (A15), (A122), (A124), (A125) or mixtures thereof.

Preferred combinations (A)+(B) are selected from the above combinations wherein (A) is a racemic compound from table 1 having the number (A12), (A14), (A20), (A27), (A40), (A45), (A46), (A47), (A48), (A52), (A62), (A67), (A68), (A78), (A80), (A88), (A99), (A104), (A05), (A106), (A107), (A1), (A116), (A121), (A126), (A127) or a mixture of two or more of said compounds.

Preferred combinations (A)+(B) are selected from the above combinations wherein (A) is a racemic compound from table 1 having the number (A15), (A39), (A49), (A50), (A51), (A57), (A58), (A59), (A60), (A61), (A64), (A81), (A98), (A108), (A109), (A110), (A116), (A117), (A118), (A119), (A120), (A123) or a mixture of two or more of said compounds.

The weight ratio of Compounds (A) to pesticide can be varied within wide limits, and its optimum weight ratio depends both on the Compounds (A) and pesticide employed and on the kind of useful plants to be treated. The ratio by weight of compound(s) (A) to compound(s) (B) is, for example, 1000:1 to 1:1000, preferably 200:1 to 1:200, in particular 100:1 to 1:100.

If the compounds are combined with other herbicidal active ingredients (B) the practical application rates of herbicides (A) may generally be reduced, preferably in the range of 0.01 to 1500 g a.i./ha, more particularly of from 0.02 to 1000 g a.i./ha.

The combined application rates of compounds (A)+(B) are preferably within the range of from 0.01 to 3000 g a.i./ha, more particularly of from 0.02 to 1000 g a.i./ha.

Preferred combinations of three active ingredients are:
(A)+(B1)+(B2.1), (A)+(B1)+(B3), (A)+(B1)+(B4.1), (A)+(B1)+(B5), (A)+(B1)+(B6), (A)+(B1)+(B7), (A)+(B1)+(B8.1), (A)+(B1)+(B9.1), (A)+(B1)+(B9.2), (A)+(B1)+(B9.3), (A)+(B1)+(B10), (A)+(B1)+(B10.1), (A)+(B1)+(B10.8), (A)+(B1)+(B10.9), (A)+(B1)+(B11), (A)+(B1)+(B11.1), (A)+(B1)+(B11.2), (A)+(B1)+(B11.3), (A)+(B1)+(B12), (A)+(B1)+(B12.1), (A)+(B1)+(B12.2), (A)+(B1)+(B12.3), (A)+(B1)+(B13), (A)+(B1)+(B13.1), (A)+(B1)+(B13.2), (A)+(B1)+(B13.3), (A)+(B1)+(B13.4), (A)+(B1)+(B13.5), (A)+(B1)+(B13.6), (A)+(B1)+(B14.2), (A)+(B1)+(B14.3), (A)+(B1)+(B15.2), (A)+(B1)+(B16), (A)+(B1)+(B17.1), (A)+(B1)+(B18.1), (A)+(B1)+(B19), (A)+(B1)+(B20.1), (A)+(B1)+(B21.1), (A)+(B1)+(B22.1), (A)+(B1)+(B23.1), (A)+(B1)+(B24.1); (A)+(B1)+(B25), (A)+(B1)+(B26.1), (A)+(B1)+(B27.1), (A)+(B1)+(B28.1), (A)+(B1)+(B29), (A)+(B1)+(B29.1), (A)+(B1)+(B29.2), (A)+(B1)+(B29.3), (A)+(B1)+(B30.1), (A)+(B1)+(B31.1), (A)+(B1)+(B32.1), (A)+(B1)+(B32.2), (A)+(B1)+(B33), (A)+(B1)+(B34), (A)+(B1)+(B34.1), (A)+(B1)+(B34.2), (A)+(B1)+(B35), (A)+(B1)+(B36), (A)+(B1)+(B36.1), (A)+(B1)+(B36.2), (A)+(B1)+(B37), (A)+(B1)+(B37.1), (A)+(B1)+(B37.2), (A)+(B1)+(B38), (A)+(B1)+(B38.1), (A)+(B1)+(B38.2), (A)+(B1)+(B39), (A)+(B1)+(B39.1), (A)+(B1)+(B40), (A)+(B1)+(B40.1), (A)+(B1)+(B41), (A)+(B1)+(B41.1), (A)+(B1)+(B41.2), (A)+(B1)+(B42), (A)+(B1)+(B42.1), (A)+(B1)+(B42.2), (A)+(B1)+(B42.3), (A)+(B1)+(B43), (A)+(B1)+(B43.1), (A)+(B1)+(B44), (A)+(B1)+(B44.1),
(A)+(B2.1)+(B3), (A)+(B2.1)+(B4.1), (A)+(B2.1)+(B5), (A)+(B2.1)+(B6), (A)+(B2.1)+(B7), (A)+(B2.1)+(B8.1), (A)+(B2.1)+(B9.1), (A)+(B2.1)+(B9.2), (A)+(B2.1)+(B9.3), (A)+(B2.1)+(B10), (A)+(B2.1)+(B10.1), (A)+(B2.1)+(B108), (A)+(B2.1)+(B10.9), (A)+(B2.1)+(B11), (A)+(B2.1)+(B11.1), (A)+(B2.1)+(B11.2), (A)+(B2.1)+(B11.3), (A)+(B2.1)+(B12), (A)+(B2.1)+(B12.1), (A)+(B2.1)+(B12.2), (A)+(B2.1)+(B12.3), (A)+(B2.1)+(B13), (A)+(B2.1)+(B13.1), (A)+(B2.1)+(B13.2), (A)+(B2.1)+(B13.3), (A)+(B2.1)+(B13.4), (A)+(B2.1)+(B13.5), (A)+(B2.1)+(B13.6), (A)+(B2.1)+(B14.2), (A)+(B2.1)+(B14.3), (A)+(B2.1)+(B15.2), (A)+(B2.1)+(B16), (A)+(B2.1)+(B17.1), (A)+(B2.1)+(B18.1), (A)+(B2.1)+(B19), (A)+(B2.1)+(B20.1), (A)+(B2.1)+(B21.1), (A)+(B2.1)+(B22.1), (A)+(B2.1)+(B23.1), (A)+(B2.1)+(B24.1); (A)+(B2.1)+(B25), (A)+(B2.1)+(B26.1), (A)+(B2.1)+(B27.1), (A)+(B21)+(B28.1), (A)+(B2.1)+(B29), (A)+(B2.1)+(B29.1), (A)+(B2.1)+(B29.2), (A)+(B2.1)+(B29.3), (A)+(B2.1)+(B30.1), (A)+(B2.1)+(B31.1), (A)+(B2.1)+(B32.1), (A)+(B2.1)+(B32.2), (A)+(B2.1)+(B33), (A)+(B2.1)+(B34), (A)+(B2.1)+(B34.1), (A)+(B2.1)+(B34.2), (A)+(B2.1)+(B35), (A)+(B2.1)+(B36), (A)+(B2.1)+(B36.1), (A)+(B2.1)+(B36.2), (A)+(B2.1)+(B37), (A)+(B2.1)+(B37.1), (A)+(B2.1)+(B37.2), (A)+(B2.1)+(B38), (A)+(B2.1)+(B38.1), (A)+(B2.1)+(B38.2), (A)+(B2.1)+(B39), (A)+(B2.1)+(B39.1), (A)+(B2.1)+(B40), (A)+(B2.1)+(B40.1), (A)+(B2.1)+(B41), (A)+(B2.1)+(B41.1), (A)+(B2.1)+(B41.2), (A)+(B2.1)+(B42), (A)+(B2.1)+(B42.1), (A)+(B2.1)+(B42.2), (A)+(B2.1)+(B42.3), (A)+(B2.1)+(B43), (A)+(B2.1)+(B43.1), (A)+(B2.1)+(B44), (A)+(B2.1)+(B44.1),
(A)+(B3)+(B4.1), (A)+(B3)+(B5), (A)+(B3)+(B6), (A)+(B3)+(B7), (A)+(B3)+(B8.1), (A)+(B3)+(B9.1), (A)+(B3)+(B9.2), (A)+(B3)+(B9.3), (A)+(B3)+(B10), (A)+(B3)+(B10.1), (A)+(B3)+(B10.8), (A)+(B3)+(B10.9), (A)+(B3)+(B11), (A)+(B3)+(B11.1), (A)+(B3)+(B11.2), (A)+(B3)+(B11.3), (A)+(B3)+(B12), (A)+(B3)+(B12.1), (A)+(B3)+(B12.2), (A)+(B3)+(B12.3), (A)+(B3)+(B13), (A)+(B3)+(B13.1), (A)+(B3)+(B13.2), (A)+(B3)+(B13.3), (A)+(B3)+(B13.4), (A)+(B3)+(B13.5), (A)+(B3)+(B13.6), (A)+(B3)+(B14.2), (A)+(B3)+(B14.3), (A)+(B3)+(B15.2), (A)+(B3)+(B16), (A)+(B3)+(B17.1), (A)+(B3)+(B18.1), (A)+(B3)+(B19), (A)+(B3)+(B20.1), (A)+(B3)+(B21.1), (A)+(B3)+(B22.1), (A)+(B3)+(B23.1), (A)+(B3)+(B24.1); (A)+(B3)+(B25), (A)+(B3)+(B26.1), (A)+(B3)+(B27.1), (A)+(B3)+(B28.1), (A)+(B3)+(B29), (A)+(B3)+(B29.1), (A)+(B3)+(B29.2), (A)+(B3)+(B29.3), (A)+(B3)+(B30.1), (A)+(B3)+(B31.1), (A)+(B3)+(B32.1), (A)+(B3)+(B32.2), (A)+(B3)+(B33), (A)+(B3)+(B34), (A)+(B3)+(B34.1), (A)+(B3)+(B34.2), (A)+(B3)+(B35), (A)+(B3)+(B36), (A)+(B3)+(B36.1), (A)+(B3)+(B36.2), (A)+(B3)+(B37), (A)+(B3)+(B37.1), (A)+(B3)+(B37.2), (A)+(B3)+(B38), (A)+(B3)+(B38.1), (A)+(B3)+(B38.2), (A)+(B3)+(B39), (A)+(B3)+(B39.1), (A)+(B3)+(B40), (A)+(B3)+(B40.1), (A)+(B3)+(B41), (A)+(B3)+(B41.1), (A)+(B3)+(B41.2), (A)+(B3)+(B42), (A)+(B3)+(B42.1), (A)+(B3)+(B42.2), (A)+(B3)+(B42.3), (A)+(B3)+(B43), (A)+(B3)+(B43.1), (A)+(B3)+(B44), (A)+(B3)+(B44.1),
(A)+(B4.1)+(B5), (A)+(B4.1)+(B6), (A)+(B4.1)+(B7), (A)+(B4.1)+(B8.1), (A)+(B4.1)+(B9.1), (A)+(B4.1)+(B9.2), (A)+(B4.1)+(B9.3), (A)+(B4.1)+(B10), (A)+(B4.1)+(B10.1), (A)+(B4.1)+(B10.8), (A)+(B4.1)+(B10.9), (A)+(B4.1)+(B11), (A)+(B4.1)+(B11.1), (A)+(B4.1)+(B11.2), (A)+(B4.1)+(B11.3), (A)+(B4.1)+(B12), (A)+(B4.1)+

(B12.1), (A)+(B4.1)+(B12.2), (A)+(B4.1)+(B12.3), (A)+(B4.1)+(B13), (A)+(B4.1)+(B13.1), (A)+(B4.1)+(B13.2), (A)+(B4.1)+(B13.3), (A)+(B4.1)+(B13.4), (A)+(B4.1)+(B13.5), (A)+(B4.1)+(B13.6), (A)+(B4.1)+(B14.2), (A)+(B4.1)+(B14.3), (A)+(B4.1)+(B15.2), (A)+(B4.1)+(B16), (A)+(B4.1)+(B17.1), (A)+(B4.1)+(B18.1), (A)+(B4.1)+(B19), (A)+(B4.1)+(B20.1), (A)+(B4.1)+(B21.1), (A)+(B4.1)+(B22.1), (A)+(B4.1)+(B23.1), (A)+(B4.1)+(B24.1); (A)+(B4.1)+(B25), (A)+(B4.1)+(B26.1), (A)+(B4.1)+(B27.1), (A)+(B4.1)+(B28.1), (A)+(B4.1)+(B29), (A)+(B4.1)+(B29.1), (A)+(B4.1)+(B29.2), (A)+(B4.1)+(B29.3), (A)+(B4.1)+(B30.1), (A)+(B4.1)+(B31.1), (A)+(B4.1)+(B32.1), (A)+(B4.1)+(B32.2), (A)+(B4.1)+(B33), (A)+(B4.1)+(B34), (A)+(B4.1)+(B341), (A)+(B4.1)+(B34.2), (A)+(B4.1)+(B35), (A)+(B4.1)+(B36), (A)+(B4.1)+(B36.1), (A)+(B4.1)+(B36.2), (A)+(B4.1)+(B37), (A)+(B4.1)+(B37.1), (A)+(B4.1)+(B37.2), (A)+(B4.1)+(B38), (A)+(B4.1)+(B38.1), (A)+(B4.1)+(B38.2), (A)+(B4.1)+(B39), (A)+(B4.1)+(B39.1), (A)+(B4.1)+(B40), (A)+(B4.1)+(B40.1), (A)+(B4.1)+(B41), (A)+(B4.1)+(B41.1), (A)+(B4.1)+(B41.2), (A)+(B4.1)+(B42), (A)+(B4.1)+(B42.1), (A)+(B4.1)+(B42.2), (A)+(B4.1)+(B42.3), (A)+(B4.1)+(B43), (A)+(B4.1)+(B43.1), (A)+(B4.1)+(B44), (A)+(B4.1)+(B44.1), (A)+(B5)+(B6), (A)+(B5)+(B7), (A)+(B5)+(B8.1), (A)+(B5)+(B9.1), (A)+(B5)+(B9.2), (A)+(B5)+(B9.3), (A)+(B5)+(B10), (A)+(B5)+(B10.1), (A)+(B5)+(B10.8), (A)+(B5)+(B10.9), (A)+(B5)+(B1), (A)+(B5)+(B11.1), (A)+(B5)+(B11.2), (A)+(B5)+(B11.3), (A)+(B5)+(B12), (A)+(B5)+(B121), (A)+(B5)+(B122), (A)+(B5)+(B12.3), (A)+(B5)+(B13), (A)+(B5)+(B13.1), (A)+(B5)+(B13.2), (A)+(B5)+(B13.3), (A)+(B5)+(B13.4), (A)+(B5)+(B13.5), (A)+(B5)+(B13.6), (A)+(B5)+(B14.2), (A)+(B5)+(B14.3), (A)+(B5)+(B15.2), (A)+(B5)+(B16), (A)+(B5)+(B17.1), (A)+(B5)+(B18.1), (A)+(B5)+(B19), (A)+(B5)+(B20.1), (A)+(B5)+(B21.1), (A)+(B5)+(B22.1), (A)+(B5)+(B23.1), (A)+(B5)+(B24.1); (A)+(B5)+(B25), (A)+(B5)+(B26.1), (A)+(B5)+(B27.1), (A)+(B5)+(B28.1), (A)+(B5)+(B29), (A)+(B5)+(B29.1), (A)+(B5)+(B29.2), (A)+(B5)+(B29.3), (A)+(B5)+(B30.1), (A)+(B5)+(B31.1), (A)+(B5)+(B32.1), (A)+(B5)+(B32.2), (A)+(B5)+(B33), (A)+(B5)+(B34), (A)+(B5)+(B34.1), (A)+(B5)+(B34.2), (A)+(B5)+(B35), (A)+(B5)+(B36), (A)+(B5)+(B36.1), (A)+(B5)+(B36.2), (A)+(B5)+(B37), (A)+(B5)+(B37.1), (A)+(B5)+(B37.2), (A)+(B5)+(B38), (A)+(B5)+(B38.1), (A)+(B5)+(B38.2), (A)+(B5)+(B39), (A)+(B5)+(B39.1), (A)+(B5)+(B40), (A)+(B5)+(B40.1), (A)+(B5)+(B41), (A)+(B5)+(B41.1), (A)+(B5)+(B41.2), (A)+(B5)+(B42), (A)+(B5)+(B42.1), (A)+(B5)+(B42.2), (A)+(B5)+(B42.3), (A)+(B5)+(B43), (A)+(B5)+(B43.1), (A)+(B5)+(B44), (A)+(B5)+(B44.1), (A)+(B6)+(B7), (A)+(B6)+(B8.1), (A)+(B6)+(B9.1), (A)+(B6)+(B9.2), (A)+(B6)+(B9.3), (A)+(B6)+(B10), (A)+(B6)+(B10.1), (A)+(B6)+(B10.8), (A)+(B6)+(B10.9), (A)+(B6)+(B11), (A)+(B6)+(B11.1), (A)+(B6)+(B11.2), (A)+(B6)+(B11.3), (A)+(B6)+(B12), (A)+(B6)+(B12.1), (A)+(B6)+(B12.2), (A)+(B6)+(B12.3), (A)+(B6)+(B13), (A)+(B6)+(B13.1), (A)+(B6)+(B13.2), (A)+(B6)+(B13.3), (A)+(B6)+(B13.4), (A)+(B6)+(B13.5), (A)+(B6)+(B13.6), (A)+(B6)+(B14.2), (A)+(B6)+(B14.3), (A)+(B6)+(B15.2), (A)+(B6)+(B16), (A)+(B6)+(B17.1), (A)+(B6)+(B18.1), (A)+(B6)+(B19), (A)+(B6)+(B20.1), (A)+(B6)+(B21.1), (A)+(B6)+(B22.1), (A)+(B6)+(B23.1), (A)+(B6)+(B24.1); (A)+(B6)+(B25), (A)+(B6)+(B26.1), (A)+(B6)+(B27.1), (A)+(B6)+(B28.1), (A)+(B6)+(B29), (A)+(B6)+(B29.1), (A)+(B6)+(B29.2), (A)+(B6)+(B29.3), (A)+(B6)+(B30.1), (A)+(B6)+(B31.1), (A)+(B6)+(B32.1), (A)+(B6)+(B32.2), (A)+(B6)+(B33), (A)+(B6)+(B34), (A)+(B6)+(B34.1), (A)+(B6)+(B34.2), (A)+(B6)+(B35), (A)+(B6)+(B36), (A)+(B6)+(B36.1), (A)+(B6)+(B36.2), (A)+(B6)+(B37), (A)+(B6)+(B37.1), (A)+(B6)+(B37.2), (A)+(B6)+(B38), (A)+(B6)+(B38.1), (A)+(B6)+(B38.2), (A)+(B6)+(B39), (A)+(B6)+(B39.1), (A)+(B6)+(B40), (A)+(B6)+(B40.1), (A)+(B6)+(B41), (A)+(B6)+(B41.1), (A)+(B6)+(B41.2), (A)+(B6)+(B42), (A)+(B6)+(B42.1), (A)+(B6)+(B42.2), (A)+(B6)+(B42.3), (A)+(B6)+(B43), (A)+(B6)+(B43.1), (A)+(B6)+(B44), (A)+(B6)+(B44.1), (A)+(B7)+(B8.1), (A)+(B7)+(B9.1), (A)+(B7)+(B9.2), (A)+(B7)+(B9.3), (A)+(B7)+(B10), (A)+(B7)+(B10.1), (A)+(B7)+(B10.8), (A)+(B7)+(B10.9), (A)+(B7)+(B11), (A)+(B7)+(B11.1), (A)+(B7)+(B11.2), (A)+(B7)+(B11.3), (A)+(B7)+(B12), (A)+(B7)+(B12.1), (A)+(B7)+(B12.2), (A)+(B7)+(B12.3), (A)+(B7)+(B13), (A)+(B7)+(B13.1), (A)+(B7)+(B13.2), (A)+(B7)+(B13.3), (A)+(B7)+(B13.4), (A)+(B7)+(B13.5), (A)+(B7)+(B13.6), (A)+(B7)+(B14.2), (A)+(B7)+(B14.3), (A)+(B7)+(B15.2), (A)+(B7)+(B16), (A)+(B7)+(B17.1), (A)+(B7)+(B18.1), (A)+(B7)+(B19), (A)+(B7)+(B20.1), (A)+(B7)+(B21.1), (A)+(B7)+(B22.1), (A)+(B7)+(B23.1), (A)+(B7)+(B24.1); (A)+(B7)+(B25), (A)+(B7)+(B26.1), (A)+(B7)+(B27.1), (A)+(B7)+(B28.1), (A)+(B7)+(B29), (A)+(B7)+(B29.1), (A)+(B7)+(B29.2), (A)+(B7)+(B29.3), (A)+(B7)+(B30.1), (A)+(B7)+(B31.1), (A)+(B7)+(B32.1), (A)+(B7)+(B32.2), (A)+(B7)+(B33), (A)+(B7)+(B34), (A)+(B7)+(B34.1), (A)+(B7)+(B34.2), (A)+(B7)+(B35), (A)+(B7)+(B36), (A)+(B7)+(B36.1), (A)+(B7)+(B36.2), (A)+(B7)+(B37), (A)+(B7)+(B37.1), (A)+(B7)+(B37.2), (A)+(B7)+(B38), (A)+(B7)+(B38.1), (A)+(B7)+(B38.2), (A)+(B7)+(B39), (A)+(B7)+(B39.1), (A)+(B7)+(B40), (A)+(B7)+(B40.1), (A)+(B7)+(B41), (A)+(B7)+(B41.1), (A)+(B7)+(B41.2), (A)+(B7)+(B42), (A)+(B7)+(B42.1), (A)+(B7)+(B42.2), (A)+(B7)+(B42.3), (A)+(B7)+(B43), (A)+(B7)+(B43.1), (A)+(B7)+(B44), (A)+(B7)+(B44.1), (A)+(B8.1)+(B9.1), (A)+(B8.1)+(B9.2), (A)+(B8.1)+(B9.3), (A)+(B8.1)+(B10), (A)+(B8.1)+(B10.1), (A)+(B8.1)+(B10.8), (A)+(B8.1)+(B10.9), (A)+(B8.1)+(B11), (A)+(B8.1)+(B11.1), (A)+(B8.1)+(B11.2), (A)+(B8.1)+(B11.3), (A)+(B8.1)+(B12), (A)+(B8.1)+(B12.1), (A)+(B8.1)+(B12.2), (A)+(B8.1)+(B12.3), (A)+(B8.1)+(B13), (A)+(B8.1)+(B13.1), (A)+(B8.1)+(B13.2), (A)+(B8.1)+(B13.3), (A)+(B8.1)+(B13.4), (A)+(B8.1)+(B13.5), (A)+(B8.1)+(B13.6), (A)+(B8.1)+(B14.2), (A)+(B8.1)+(B14.3), (A)+(B8.1)+(B15.2), (A)+(B8.1)+(B16), (A)+(B8.1)+(B17.1), (A)+(B8.1)+(B18.1), (A)+(B8.1)+(B19), (A)+(B8.1)+(B20.1), (A)+(B8.1)+(B21.1), (A)+(B8.1)+(B22.1), (A)+(B8.1)+(B23.1), (A)+(B8.1)+(B24.1); (A)+(B8.1)+(B25), (A)+(B8.1)+(B26.1), (A)+(B8.1)+(B27.1), (A)+(B8.1)+(B28.1), (A)+(B8.1)+(B29), (A)+(B8.1)+(B29.1), (A)+(B8.1)+(B29.2), (A)+(B8.1)+(B29.3), (A)+(B8.1)+(B30.1), (A)+(B8.1)+(B31.1), (A)+(B8.1)+(B32.1), (A)+(B8.1)+(B32.2), (A)+(B8.1)+(B33), (A)+(B8.1)+(B34), (A)+(B8.1)+(B34.1), (A)+(B8.1)+(B34.2), (A)+(B8.1)+(B35), (A)+(B8.1)+(B36), (A)+(B8.1)+(B36.1), (A)+(B8.1)+(B36.2), (A)+(B8.1)+(B37), (A)+(B8.1)+(B37.1), (A)+(B8.1)+(B37.2), (A)+(B8.1)+(B38), (A)+(B8.1)+(B38.1), (A)+(B8.1)+(B38.2), (A)+(B8.1)+(B39), (A)+(B8.1)+(B39.1), (A)+(B8.1)+(B40), (A)+(B8.1)+(B40.1), (A)+(B8.1)+(B41), (A)+(B8.1)+(B41.1), (A)+(B8.1)+(B41.2), (A)+(B8.1)+(B42), (A)+(B8.1)+(B42.1), (A)+(B8.1)+(B42.2), (A)+(B8.1)+(B42.3), (A)+(B8.1)+(B43), (A)+(B8.1)+(B43.1), (A)+(B8.1)+(B44), (A)+(B8.1)+(B44.1), (A)+(B9.1)+(B10), (A)+(B9.1)+(B10.1), (A)+(B9.1)+(B10.8), (A)+(B9.1)+(B10.9), (A)+(B9.1)+(B11), (A)+(B9.1)+(B11.1), (A)+(B9.1)+(B11.2), (A)+(B9.1)+(B11.3), (A)+(B9.1)+(B12), (A)+(B9.1)+(B12.1), (A)+(B9.1)+

(B12.2), (A)+(B9.1)+(B12.3), (A)+(B9.1)+(B13), (A)+(B9.1)+(B13.1), (A)+(B9.1)+(B13.2), (A)+(B9.1)+(B13.3), (A)+(B9.1)+(B13.4), (A)+(B9.1)+(B13.5), (A)+(B9.1)+(B13.6), (A)+(B9.1)+(B14.2), (A)+(B9.1)+(B14.3), (A)+(B9.1)+(B15.2), (A)+(B9.1)+(B16), (A)+(B9.1)+(B17.1), (A)+(B9.1)+(B18.1), (A)+(B9.1)+(B19), (A)+(B9.1)+(B20.1), (A)+(B9.1)+(B21.1), (A)+(B9.1)+(B22.1), (A)+(B9.1)+(B23.1), (A)+(B9.1)+(B24.1); (A)+(B9.1)+(B25), (A)+(B9.1)+(B26.1), (A)+(B9.1)+(B27.1), (A)+(B9.1)+(B28.1), (A)+(B9.1)+(B29), (A)+(B9.1)+(B29.1), (A)+(B9.1)+(B29.2), (A)+(B9.1)+(B29.3), (A)+(B9.1)+(B30.1), (A)+(B9.1)+(B31.1), (A)+(B9.1)+(B32.1), (A)+(B9.1)+(B32.2), (A)+(B9.1)+(B33), (A)+(B9.1)+(B34), (A)+(B9.1)+(B34.1), (A)+(B9.1)+(B34.2), (A)+(B9.1)+(B35), (A)+(B9.1)+(B36), (A)+(B9.1)+(B36.1), (A)+(B9.1)+(B36.2), (A)+(B9.1)+(B37), (A)+(B9.1)+(B37.1), (A)+(B9.1)+(B37.2), (A)+(B9.1)+(B38), (A)+(B9.1)+(B38.1), (A)+(B9.1)+(B38.2) (A)+(B9.1)+(B39), (A)+(B9.1)+(B39.1), (A)+(B9.1)+(B40), (A)+(B9.1)+(B40.1), (A)+(B9.1)+(B41), (A)+(B9.1)+(B41.1), (A)+(B9.1)+(B41.2), (A)+(B9.1)+(B42), (A)+(B9.1)+(B42.1), (A)+(B9.1)+(B42.2), (A)+(B9.1)+(B42.3), (A)+(B9.1)+(B43), (A)+(B9.1)+(B43.1), (A)+(B9.1)+(B44), (A)+(B9.1)+(B44.1), (A)+(B9.2)+(B10), (A)+(B9.2)+(B10.1), (A)+(B9.2)+(B10.8), (A)+(B9.2)+(B10.9), (A)+(B9.2)+(B11), (A)+(B9.2)+(B11.1), (A)+(B9.2)+(B11.2), (A)+(B9.2)+(B11.3), (A)+(B9.2)+(B12), (A)+(B9.2)+(B12.1), (A)+(B9.2)+(B12.2), (A)+(B9.2)+(B12.3), (A)+(B9.2)+(B13), (A)+(B9.2)+(B13.1), (A)+(B9.2)+(B13.2), (A)+(B9.2)+(B13.3), (A)+(B9.2)+(B13.4), (A)+(B9.2)+(B13.5), (A)+(B9.2)+(B13.6), (A)+(B9.2)+(B14.2), (A)+(B9.2)+(B14.3), (A)+(B9.2)+(B15.2), (A)+(B9.2)+(B16), (A)+(B9.2)+(B17.1), (A)+(B9.2)+(B18.1), (A)+(B9.2)+(B19), (A)+(B9.2)+(B20.1), (A)+(B9.2)+(B21.1), (A)+(B9.2)+(B22.1), (A)+(B9.2)+(B23.1), (A)+(B9.2)+(B24.1); (A)+(B9.2)+(B25), (A)+(B9.2)+(B26.1), (A)+(B9.2)+(B27.1), (A)+(B9.2)+(B28.1), (A)+(B9.2)+(B29), (A)+(B9.2)+(B29.1), (A)+(B9.2)+(B29.2), (A)+(B9.2)+(B29.3), (A)+(B9.2)+(B30.1), (A)+(B9.2)+(B31.1), (A)+(B9.2)+(B32.1), (A)+(B9.2)+(B32.2), (A)+(B9.2)+(B33), (A)+(B9.2)+(B34), (A)+(B9.2)+(B34.1), (A)+(B9.2)+(B34.2), (A)+(B9.2)+(B35), (A)+(B9.2)+(B36), (A)+(B9.2)+(B36.1), (A)+(B9.2)+(B36.2), (A)+(B9.2)+(B37), (A)+(B9.2)+(B37.1), (A)+(B9.2)+(B37.2), (A)+(B9.2)+(B38), (A)+(B9.2)+(B38.1), (A)+(B9.2)+(B38.2), (A)+(B9.2)+(B39), (A)+(B9.2)+(B39.1), (A)+(B9.2)+(B40), (A)+(B9.2)+(B40.1), (A)+(B9.2)+(B41), (A)+(B9.2)+(B41.1), (A)+(B9.2)+(B41.2), (A)+(B9.2)+(B42), (A)+(B9.2)+(B42.1), (A)+(B9.2)+(B42.2), (A)+(B9.2)+(B42.3), (A)+(B9.2)+(B43), (A)+(B9.2)+(B43.1), (A)+(B9.2)+(B44), (A)+(B9.2)+(B44.1), (A)+(B9.3)+(B10), (A)+(B9.3)+(B10.1), (A)+(B9.3)+(B10.8), (A)+(B9.3)+(B10.9), (A)+(B9.3)+(B11), (A)+(B9.3)+(B11.1), (A)+(B9.3)+(B11.2), (A)+(B9.3)+(B11.3), (A)+(B9.3)+(B12), (A)+(B9.3)+(B12.1), (A)+(B9.3)+(B12.2), (A)+(B9.3)+(B12.3), (A)+(B9.3)+(B13), (A)+(B9.3)+(B13.1), (A)+(B9.3)+(B13.2), (A)+(B9.3)+(B13.3), (A)+(B9.3)+(B13.4), (A)+(B9.3)+(B13.5), (A)+(B9.3)+(B13.6), (A)+(B9.3)+(B14.2), (A)+(B9.3)+(B14.3), (A)+(B9.3)+(B15.2), (A)+(B9.3)+(B16), (A)+(B9.3)+(B17.1), (A)+(B9.3)+(B18.1), (A)+(B9.3)+(B19), (A)+(B9.3)+(B20.1), (A)+(B9.3)+(B21.1), (A)+(B9.3)+(B22.1), (A)+(B9.3)+(B23.1), (A)+(B9.3)+(B24.1); (A)+(B9.3)+(B25), (A)+(B9.3)+(B26.1), (A)+(B9.3)+(B27.1), (A)+(B9.3)+(B28.1), (A)+(B9.3)+(B29), (A)+(B9.3)+(B29.1) (A)+(B9.3)+(B29.2), (A)+(B9.3)+(B29.3), (A)+(B9.3)+(B30.1), (A)+(B9.3)+(B31.1), (A)+(B9.3)+(B32.1), (A)+(B9.3)+(B32.2), (A)+(B9.3)+(B33), (A)+(B9.3)+(B34), (A)+(B9.3)+(B34.1), (A)+(B9.3)+(B34.2), (A)+(B9.3)+(B35), (A)+(B9.3)+(B36), (A)+(B9.3)+(B36.1), (A)+(B9.3)+(B36.2), (A)+(B9.3)+(B37), (A)+(B9.3)+(B37.1), (A)+(B9.3)+(B37.2), (A)+(B9.3)+(B38), (A)+(B9.3)+(B38.1), (A)+(B9.3)+(B38.2), (A)+(B9.3)+(B39), (A)+(B9.3)+(B39.1), (A)+(B9.3)+(B40), (A)+(B9.3)+(B40.1), (A)+(B9.3)+(B41), (A)+(B9.3)+(B41.1), (A)+(B9.3)+(B41.2), (A)+(B9.3)+(B42), (A)+(B9.3)+(B42.1), (A)+(B9.3)+(B42.2), (A)+(B9.3)+(B42.3), (A)+(B9.3)+(B43), (A)+(B9.3)+(B43.1), (A)+(B9.3)+(B44), (A)+(B9.3)+(B44.1),
(A)+(B 10)+(B11), (A)+(B10)+(B11.1), (A)+(B10)+(B1.2), (A)+(B10)+(B11.3), (A)+(B 10)+(B12), (A)+(B10)+(B12.1), (A)+(B 10)+(B12.2), (A)+(B 10)+(B12.3), (A)+(B10)+(B13), (A)+(B10)+(B13.1), (A)+(B10)+(B13.2), (A)+(B10)+(B13.3), (A)+(B10)+(B13.4), (A)+(B10)+(B13.5), (A)+(B10)+(B13.6), (A)+(B10)+(B14.2), (A)+(B10)+(B14.3), (A)+(B10)+(B15.2), (A)+(B10)+(B16), (A)+(B10)+(B17.1), (A)+(B10)+(B18.1), (A)+(B10)+(B19), (A)+(B10)+(B20.1), (A)+(B 10)+(B21.1), (A)+(B 10)+(B22.1), (A)+(B 10)+(B23.1), (A)+(B10)+(B24.1); (A)+(B10)+(B25), (A)+(B10)+(B26.1), (A)+(B10)+(B27.1), (A)+(B10)+(B28.1), (A)+(B10)+(B29), (A)+(B10)+(B29.1), (A)+(B10)+(B29.2), (A)+(B10)+(B29.3), (A)+(B10)+(B30.1), (A)+(B10)+(B31.1), (A)+(B10)+(B32.1), (A)+(B10)+(B32.2), (A)+(B10)+(B33), (A)+(B10)+(B34), (A)+(B10)+(B34.1), (A)+(B10)+(B34.2), (A)+(B10)+(B35), (A)+(B10)+(B36), (A)+(B 10)+(B36.1), (A)+(B10)+(B36.2), (A)+(B10)+(B37), (A)+(B10)+(B37.1), (A)+(B10)+(B37.2), (A)+(B10)+(B38), (A)+(B10)+(B38.1), (A)+(B 10)+(B38.2), (A)+(B10)+(B39), (A)+(B10)+(B39.1), (A)+(B10)+(B40), (A)+(B10)+(B40.1), (A)+(B10)+(B41), (A)+(B10)+(B41.1), (A)+(B 10)+(B41.2), (A)+(B 10)+(B42), (A)+(B10)+(B42.1), (A)+(B10)+(B42.2), (A)+(B10)+(B42.3), (A)+(B10)+(B43), (A)+(B10)+(B43.1), (A)+(B10)+(B44), (A)+(B10)+(B44.1),
(A)+(B10.8)+(B11), (A)+(B10.8)+(B11.1), (A)+(B10.8)+(B11.2), (A)+(B10.8)+(B11.3), (A)+(B10.8)+(B12), (A)+(B10.8)+(B12.1), (A)+(B10.8)+(B12.2), (A)+(B10.8)+(B12.3), (A)+(B10.8)+(B13), (A)+(B10.8)+(B13.1), (A)+(B10.8)+(B13.2), (A)+(B10.8)+(B13.3), (A)+(B10.8)+(B13.4), (A)+(B10.8)+(B13.5), (A)+(B10.8)+(B13.6), (A)+(B10.8)+(B14.2), (A)+(B10.8)+(B14.3), (A)+(B10.8)+(B15.2), (A)+(B10.8)+(B16), (A)+(B10.8)+(B17.1), (A)+(B10.8)+(B18.1), (A)+(B10.8)+(B19), (A)+(B10.8)+(B20.1), (A)+(B10.8)+(B21.1), (A)+(B10.8)+(B22.1), (A)+(B10.8)+(B23.1), (A)+(B10.8)+(B24.1); (A)+(B10.8)+(B25), (A)+(B10.8)+(B26.1), (A)+(B10.8)+(B27.1), (A)+(B10.8)+(B28.1), (A)+(B10.8)+(B29), (A)+(B10.8)+(B29.1), (A)+(B10.8)+(B29.2), (A)+(B10.8)+(B29.3), (A)+(B10.8)+(B30.1), (A)+(B10.8)+(B31.1), (A)+(B10.8)+(B32.1), (A)+(B10.8)+(B32.2), (A)+(B10.8)+(B33), (A)+(B10.8)+(B34), (A)+(B10.8)+(B34.1), (A)+(B10.8)+(B34.2), (A)+(B10.8)+(B35), (A)+(B10.8)+(B36), (A)+(B10.8)+(B36.1), (A)+(B10.8)+(B36.2), (A)+(B10.8)+(B37), (A)+(B10.8)+(B37.1), (A)+(B10.8)+(B37.2), (A)+(B10.8)+(B38), (A)+(B10.8)+(B38.1), (A)+(B10.8)+(B38.2), (A)+(B10.8)+(B39), (A)+(B10.8)+(B39.1), (A)+(B10.8)+(B40), (A)+(B10.8)+(B40.1), (A)+(B10.8)+(B41), (A)+(B10.8)+(B41.1), (A)+(B10.8)+(B41.2), (A)+(B10.8)+(B42), (A)+(B10.8)+(B42.1), (A)+(B10.8)+(B42.2), (A)+(B10.8)+(B42.3), (A)+(B10.8)+(B43), (A)+(B10.8)+(B43.1), (A)+(B10.8)+(B44), (A)+(B10.8)+(B44.1),
(A)+(B10.9)+(B11), (A)+(B10.9)+(B11.1), (A)+(B10.9)+(B11.2), (A)+(B10.9)+(B11.3), (A)+(B10.9)+(B12), (A)+(B10.9)+(B12.1), (A)+(B10.9)+(B12.2), (A)+(B10.9)+(B12.3), (A)+(B10.9)+(B13), (A)+(B10.9)+(B13.1), (A)+(B10.9)+(B13.2), (A)+(B10.9)+(B13.3), (A)+(B10.9)+

(B13.4), (A)+(B10.9)+(B13.5), (A)+(B10.9)+(B13.6), (A)+(B10.9)+(B14.2), (A)+(B10.9)+(B14.3), (A)+(B10.9)+(B15.2), (A)+(B10.9)+(B16), (A)+(B10.9)+(B17.1), (A)+(B10.9)+(B18.1), (A)+(B10.9)+(B19), (A)+(B10.9)+(B20.1), (A)+(B10.9)+(B21.1), (A)+(B10.9)+(B22.1), (A)+(B10.9)+(B23.1), (A)+(B10.9)+(B24.1); (A)+(B10.9)+(B25), (A)+(B10.9)+(B26.1), (A)+(B10.9)+(B27.1), (A)+(B10.9)+(B28.1), (A)+(B10.9)+(B29), (A)+(B10.9)+(B29.1), (A)+(B10.9)+(B29.2), (A)+(B10.9)+(B29.3), (A)+(B10.9)+(B30.1), (A)+(B10.9)+(B31.1), (A)+(B10.9)+(B32.1), (A)+(B10.9)+(B32.2), (A)+(B10.9)+(B33), (A)+(B10.9)+(B34), (A)+(B10.9)+(B34.1), (A)+(B10.9)+(B342), (A)+(B10.9)+(B35), (A)+(B10.9)+(B36), (A)+(B10.9)+(B36.1), (A)+(B10.9)+(B36.2), (A)+(B10.9)+(B37), (A)+(B10.9)+(B37.1), (A)+(B10.9)+(B37.2), (A)+(B10.9)+(B38), (A)+(B10.9)+(B38.1), (A)+(B10.9)+(B38.2), (A)+(B10.9)+(B39), (A)+(B10.9)+(B39.1), (A)+(B10.9)+(B40), (A)+(B10.9)+(B40.1), (A)+(B10.9)+(B41), (A)+(B10.9)+(B41.1), (A)+(B10.9)+(B41.2), (A)+(B10.9)+(B42), (A)+(B10.9)+(B42.1), (A)+(B10.9)+(B42.2), (A)+(B10.9)+(B42.3), (A)+(B10.9)+(B43), (A)+(B10.9)+(B43.1), (A)+(B10.9)+(B44), (A)+(B10.9)+(B44.1), (A)+(B11)+(B12), (A)+(B11)+(B13), (A)+(B11)+(B13.6), (A)+(B11)+(B14.2), (A)+(B11)+(B14.3), (A)+(B11)+(B15.2), (A)+(B1)+(B16), (A)+(B11)+(B17.1), (A)+(B11)+(B18.1), (A)+(B11)+(B19), (A)+(B11)+(B20.1), (A)+(B11)+(B21.1), (A)+(B11)+(B22.1), (A)+(B11)+(B23.1), (A)+(B11)+(B24.1); (A)+(B11)+(B25), (A)+(B11)+(B26.1), (A)+(B11)+(B27.1), (A)+(B11)+(B28.1), (A)+(B11)+(B29), (A)+(B11)+(B29.1), (A)+(B11)+(B29.2), (A)+(B11)+(B29.3), (A)+(B11)+(B30.1), (A)+(B11)+(B31.1), (A)+(B11)+(B32.1), (A)+(B11)+(B32.2), (A)+(B11)+(B33), (A)+(B11)+(B34), (A)+(B11)+(B34.1), (A)+(B11)+(B34.2), (A)+(B11)+(B35), (A)+(B11)+(B36), (B1)+(B36.1), (A)+(B11)+(B36.2), (A)+(B11)+(B37), (A)+(B11)+(B37.1), (A)+(B11)+(B37.2), (A)+(B11)+(B38), (A)+(B11)+(B38.1), (A)+(B11)+(B38.2), (A)+(B11)+(B39), (A)+(B11)+(B39.1), (A)+(B11)+(B40), (A)+(B11)+(B40.1), (A)+(B11)+(B41), (A)+(B11)+(B41.1), (A)+(B11)+(B41.2), (A)+(B11)+(B42), (A)+(B11)+(B42.1), (A)+(B11)+(B42.2), (A)+(B11)+(B42.3), (A)+(B11)+(B43), (A)+(B11)+(B43.1), (A)+(B11)+(B44), (A)+(B11)+(B44.1), (A)+(B11.2)+(B12), (A)+(B11.2)+(B13), (A)+(B11.2)+(B136), (A)+(B11.2)+(B14.2), (A)+(B11.2)+(B14.3), (A)+(B11.2)+(B15.2), (A)+(B11.2)+(B16), (A)+(B1.2)+(B17.1), (A)+(B11.2)+(B18.1), (A)+(B11.2)+(B19), (A)+(B11.2)+(B20.1), (A)+(B11.2)+(B21.1), (A)+(B11.2)+(B22.1), (A)+(B11.2)+(B23.1), (A)+(B11.2)+(B24.1); (A)+(B11.2)+(B25), (A)+(B11.2)+(B26.1), (A)+(B11.2)+(B27.1), (A)+(B1.2)+(B28.1), (A)+(B11.2)+(B29), (A)+(B11.2)+(B29.1), (A)+(B11.2)+(B29.2), (A)+(B11.2)+(B29.3), (A)+(B11.2)+(B30.1), (A)+(B11.2)+(B31.1), (A)+(B11.2)+(B32.1), (A)+(B11.2)+(B32.2), (A)+(B11.2)+(B33), (A)+(B11.2)+(B34), (A)+(B11.2)+(B34.1), (A)+(B11.2)+(B34.2), (A)+(B11.2)+(B35), (A)+(B11.2)+(B36), (A)+(B11.2)+(B36.1), (A)+(B11.2)+(B36.2), (A)+(B11.2)+(B37), (A)+(B11.2)+(B37.1), (A)+(B11.2)+(B37.2), (A)+(B11.2)+(B38), (A)+(B11.2)+(B38.1), (A)+(B11.2)+(B38.2), (A)+(B11.2)+(B39), (A)+(B11.2)+(B39.1), (A)+(B11.2)+(B40), (A)+(B11.2)+(B40.1), (A)+(B11.2)+(B41), (A)+(B11.2)+(B41.1), (A)+(B11.2)+(B41.2), (A)+(B11.2)+(B42), (A)+(B11.2)+(B42.1), (A)+(B11.2)+(B42.2), (A)+(B11.2)+(B42.3), (A)+(B11.2)+(B43), (A)+(B11.2)+(B43.1), (A)+(B11.2)+(B44), (A)+(B11.2)+(B44.1), (A)+(B12)+(B13), (A)+(B12)+(B13.6), (A)+(B12)+(B14.2), (A)+(B12)+(B14.3), (A)+(B12)+(B15.2), (A)+(B12)+(B16), (A)+(B12)+(B17.1), (A)+(B12)+(B18.1), (A)+(B12)+(B19), (A)+(B12)+(B20.1), (A)+(B12)+(B21.1), (A)+(B12)+(B22.1), (A)+(B12)+(B23.1), (A)+(B12)+(B24.1); (A)+(B12)+(B25), (A)+(B12)+(B26.1), (A)+(B12)+(B27.1), (A)+(B12)+(B28.1), (A)+(B12)+(B29), (A)+(B12)+(B29.1), (A)+(B12)+(B29.2), (A)+(B12)+(B29.3), (A)+(B12)+(B30.1), (A)+(B12)+(B31.1), (A)+(B12)+(B32.1), (A)+(B12)+(B32.2), (A)+(B12)+(B33), (A)+(B12)+(B34), (A)+(B12)+(B34.1), (A)+(B12)+(B34.2), (A)+(B12)+(B35), (A)+(B12)+(B36), (A)+(B12)+(B36.1), (A)+(B12)+(B36.2), (A)+(B12)+(B37), (A)+(B12)+(B37.1), (A)+(B12)+(B37.2), (A)+(B12)+(B38), (A)+(B12)+(B38.1), (A)+(B12)+(B38.2), (A)+(B12)+(B39), (A)+(B12)+(B39.1), (A)+(B12)+(B40), (A)+(B12)+(B40.1), (A)+(B12)+(B41), (A)+(B12)+(B41.1), (A)+(B12)+(B41.2), (A)+(B12)+(B42), (A)+(B12)+(B42.1), (A)+(B12)+(B42.2), (A)+(B12)+(B42.3), (A)+(B12)+(B43), (A)+(B12)+(B43.1), (A)+(B12)+(B44), (A)+(B12)+(B44.1), (A)+(B12.2)+(B13), (A)+(B12.2)+(B13.6), (A)+(B12.2)+(B14.2), (A)+(B12.2)+(B14.3), (A)+(B12.2)+(B15.2), (A)+(B12.2)+(B16), (A)+(B12.2)+(B17.1), (A)+(B12.2)+(B18.1), (A)+(B12.2)+(B19), (A)+(B12.2)+(B20.1), (A)+(B12.2)+(B21.1), (A)+(B12.2)+(B22.1), (A)+(B12.2)+(B23.1), (A)+(B12.2)+(B24.1); (A)+(B12.2)+(B25), (A)+(B12.2)+(B26.1), (A)+(B12.2)+(B27.1), (A)+(B12.2)+(B28.1), (A)+(B12.2)+(B29), (A)+(B12.2)+(B29.1), (A)+(B12.2)+(B29.2), (A)+(B12.2)+(B29.3), (A)+(B12.2)+(B30.1), (A)+(B12.2)+(B31.1), (A)+(B12.2)+(B32.1), (A)+(B12.2)+(B32.2), (A)+(B12.2)+(B33), (A)+(B12.2)+(B34), (A)+(B12.2)+(B34.1), (A)+(B12.2)+(B34.2), (A)+(B12.2)+(B35), (A)+(B12.2)+(B36), (A)+(B12.2)+(B36.1), (A)+(B12.2)+(B36.2), (A)+(B12.2)+(B37), (A)+(B12.2)+(B37.1), (A)+(B12.2)+(B37.2), (A)+(B12.2)+(B38), (A)+(B12.2)+(B38.1), (A)+(B12.2)+(B38.2), (A)+(B12.2)+(B39), (A)+(B12.2)+(B39.1), (A)+(B12.2)+(B40), (A)+(B12.2)+(B40.1), (A)+(B12.2)+(B41), (A)+(B12.2)+(B41.1), (A)+(B12.2)+(B41.2), (A)+(B12.2)+(B42), (A)+(B12.2)+(B42.1), (A)+(B12.2)+(B42.2), (A)+(B12.2)+(B42.3), (A)+(B12.2)+(B43), (A)+(B12.2)+(B43.1), (A)+(B12.2)+(B44), (A)+(B12.2)+(B44.1), (A)+(B12.3)+(B13), (A)+(B12.3)+(B13.6), (A)+(B12.3)+(B14.2), (A)+(B12.3)+(B14.3), (A)+(B12.3)+(B15.2), (A)+(B12.3)+(B16), (A)+(B12.3)+(B17.1), (A)+(B12.3)+(B18.1), (A)+(B12.3)+(B19), (A)+(B12.3)+(B20.1), (A)+(B12.3)+(B21.1), (A)+(B12.3)+(B22.1), (A)+(B12.3)+(B23.1), (A)+(B12.3)+(B24.1); (A)+(B12.3)+(B25), (A)+(B12.3)+(B26.1), (A)+(B12.3)+(B27.1), (A)+(B12.3)+(B28.1), (A)+(B12.3)+(B29), (A)+(B12.3)+(B29.1), (A)+(B12.3)+(B29.2), (A)+(B12.3)+(B29.3), (A)+(B12.3)+(B30.1), (A)+(B12.3)+(B31.1), (A)+(B12.3)+(B32.1), (A)+(B12.3)+(B32.2), (A)+(B12.3)+(B33), (A)+(B12.3)+(B34), (A)+(B12.3)+(B34.1), (A)+(B12.3)+(B34.2), (A)+(B12.3)+(B35), (A)+(B12.3)+(B36), (A)+(B12.3)+(B36.1), (A)+(B12.3)+(B36.2), (A)+(B12.3)+(B37), (A)+(B12.3)+(B37.1), (A)+(B12.3)+(B37.2), (A)+(B12.3)+(B38), (A)+(B12.3)+(B38.1), (A)+(B12.3)+(B38.2), (A)+(B12.3)+(B39), (A)+(B12.3)+(B39.1), (A)+(B12.3)+(B40), (A)+(B12.3)+(B40.1), (A)+(B12.3)+(B41), (A)+(B12.3)+(B41.1), (A)+(B12.3)+(B41.2), (A)+(B12.3)+(B42), (A)+(B12.3)+(B42.1), (A)+(B12.3)+(B42.2), (A)+(B12.3)+(B42.3), (A)+(B12.3)+(B43), (A)+(B12.3)+(B43.1), (A)+(B12.3)+(B44), (A)+(B12.3)+(B44.1), (A)+(B13)+(B14.2), (A)+(B13)+(B14.3), (A)+(B13)+(B15.2), (A)+(B13)+(B16), (A)+(B13)+(B17.1), (A)+(B13)+(B18.1), (A)+(B13)+(B19), (A)+(B13)+(B20.1), (A)+(B13)+(B21.1), (A)+(B13)+(B22.1), (A)+(B13)+(B23.1), (A)+(B13)+(B24.1); (A)+(B13)+(B25), (A)+(B13)+(B26.1), (A)+(B13)+(B27.1), (A)+(B13)+(B28.1), (A)+(B13)+(B29), (A)+(B13)+(B29.1), (A)+(B13)+(B29.2), (A)+(B13)+(B29.3), (A)+(B13)+(B30.1), (A)+(B13)+(B31.1), (A)+(B13)+(B32.1), (A)+(B13)+(B32.2), (A)+(B13)+(B33), (A)+(B13)+(B34), (A)+(B13)+(B34.1), (A)+(B13)+(B34.2), (A)+(B13)+(B35), (A)+(B13)+(B36), (A)+(B13)+(B36.1), (A)+(B13)+(B36.2), (A)+(B13)+(B37), (A)+(B13)+(B37.1), (A)+(B13)+(B37.2), (A)+(B13)+(B38), (A)+(B13)+(B38.1), (A)+(B13)+(B38.2), (A)+(B13)+(B39), (A)+(B13)+(B39.1), (A)+(B13)+(B40), (A)+(B13)+(B40.1), (A)+(B13)+(B41), (A)+(B13)+(B41.1), (A)+(B13)+(B41.2), (A)+(B13)+(B42), (A)+(B13)+(B42.1), (A)+(B13)+(B42.2), (A)+(B13)+(B42.3), (A)+(B13)+(B43), (A)+(B13)+(B43.1), (A)+(B13)+(B44), (A)+(B13)+(B44.1), (A)+(B13.6)+(B14.2), (A)+(B13.6)+(B14.3), (A)+(B13.6)+(B15.2), (A)+(B13.6)+(B16), (A)+(B13.6)+(B17.1), (A)+(B13.6)+(B18.1), (A)+(B13.6)+(B19), (A)+(B13.6)+(B20.1), (A)+(B13.6)+(B21.1), (A)+(B13.6)+(B22.1), (A)+(B13.6)+(B23.1), (A)+(B13.6)+(B24.1); (A)+(B13.6)+(B25), (A)+(B13.6)+(B26.1), (A)+(B13.6)+(B27.1), (A)+(B13.6)+(B28.1), (A)+(B13.6)+(B29), (A)+(B13.6)+(B29.1), (A)+(B13.6)+(B29.2), (A)+(B13.6)+(B29.3), (A)+(B13.6)+(B30.1), (A)+(B13.6)+(B31.1), (A)+(B13.6)+(B32.1), (A)+(B13.6)+(B32.2), (A)+(B13.6)+(B33), (A)+(B13.6)+(B34), (A)+(B13.6)+(B34.1), (A)+(B13.6)+(B34.2), (A)+(B13.6)+(B35), (A)+(B13.6)+(B36), (A)+(B13.6)+(B36.1), (A)+(B13.6)+(B36.2), (A)+(B13.6)+(B37), (A)+(B13.6)+(B37.1), (A)+(B13.6)+(B37.2), (A)+(B13.6)+(B38), (A)+(B13.6)+(B38.1), (A)+(B13.6)+(B38.2), (A)+(B13.6)+(B39), (A)+(B13.6)+(B39.1), (A)+(B13.6)+(B40), (A)+(B13.6)+(B40.1), (A)+(B13.6)+(B41), (A)+(B13.6)+(B41.1), (A)+(B13.6)+(B41.2), (A)+(B13.6)+(B42), (A)+(B13.6)+(B42.1), (A)+(B13.6)+(B42.2), (A)+(B13.6)+(B42.3), (A)+(B13.6)+(B43), (A)+(B13.6)+(B43.1), (A)+(B13.6)+(B44), (A)+(B13.6)+(B44.1), (A)+(B14.3)+(B15.2), (A)+(B14.3)+(B16), (A)+(B14.3)+(B17.1), (A)+(B14.3)+(B18.1), (A)+(B14.3)+(B19), (A)+(B14.3)+(B20.1), (A)+(B14.3)+(B21.1), (A)+(B14.3)+(B22.1), (A)+(B14.3)+(B23.1), (A)+(B14.3)+(B24.1); (A)+(B14.3)+(B25), (A)+(B14.3)+(B26.1), (A)+(B14.3)+(B27.1), (A)+(B14.3)+(B28.1), (A)+(B14.3)+(B29), (A)+(B14.3)+(B29.1), (A)+(B14.3)+(B29.2), (A)+(B14.3)+(B29.3), (A)+(B14.3)+(B30.1), (A)+(B14.3)+(B31.1), (A)+(B14.3)+(B32.1), (A)+(B14.3)+(B32.2), (A)+(B14.3)+(B33), (A)+(B14.3)+(B34), (A)+(B14.3)+(B34.1), (A)+(B14.3)+(B34.2), (A)+(B14.3)+(B35), (A)+(B14.3)+(B36), (A)+(B14.3)+(B36.1), (A)+(B14.3)+(B36.2), (A)+(B14.3)+(B37), (A)+(B14.3)+(B37.1), (A)+(B14.3)+(B37.2), (A)+(B14.3)+(B38), (A)+(B14.3)+(B38.1), (A)+(B14.3)+(B38.2), (A)+(B14.3)+(B39), (A)+(B14.3)+(B39.1), (A)+(B14.3)+(B40), (A)+(B14.3)+(B40.1), (A)+(B14.3)+(B41), (A)+(B14.3)+(B41.1), (A)+(B14.3)+(B41.2), (A)+(B14.3)+(B42), (A)+(B14.3)+(B42.1), (A)+(B14.3)+(B42.2), (A)+(B14.3)+(B42.3), (A)+(B14.3)+(B43), (A)+(B14.3)+(B43.1), (A)+(B14.3)+(B44), (A)+(B14.3)+(B44.1), (A)+(B15.2)+(B16), (A)+(B15.2)+(B17.1), (A)+(B15.2)+(B18.1), (A)+(B15.2)+(B19), (A)+(B15.2)+(B20.1), (A)+(B15.2)+(B21.1), (A)+(B15.2)+(B22.1), (A)+(B15.2)+(B23.1), (A)+(B15.2)+(B24.1); (A)+(B15.2)+(B25), (A)+(B15.2)+(B26.1), (A)+(B15.2)+(B27.1), (A)+(B15.2)+(B28.1), (A)+(B15.2)+(B29), (A)+(B15.2)+(B29.1), (A)+(B15.2)+(B29.2), (A)+(B15.2)+(B29.3), (A)+(B15.2)+(B30.1), (A)+(B15.2)+(B31.1), (A)+(B15.2)+(B32.1), (A)+(B15.2)+(B32.2), (A)+(B15.2)+(B33), (A)+(B15.2)+(B34), (A)+(B15.2)+(B34.1), (A)+(B15.2)+(B34.2), (A)+(B15.2)+(B35), (A)+(B15.2)+(B36), (A)+(B15.2)+(B36.1), (A)+(B15.2)+(B36.2), (A)+(B15.2)+(B37), (A)+(B15.2)+(B37.1), (A)+(B15.2)+(B37.2), (A)+(B15.2)+(B38), (A)+(B15.2)+(B38.1), (A)+(B15.2)+(B38.2), (A)+(B15.2)+(B39), (A)+(B15.2)+(B39.1), (A)+(B15.2)+(B40), (A)+(B15.2)+(B40.1), (A)+(B15.2)+(B41), (A)+(B15.2)+(B41.1), (A)+(B15.2)+(B41.2), (A)+(B15.2)+(B42), (A)+(B15.2)+(B42.1), (A)+(B15.2)+(B42.2), (A)+(B15.2)+(B42.3), (A)+(B15.2)+(B43), (A)+(B15.2)+(B43.1), (A)+(B15.2)+(B44), (A)+(B15.2)+(B44.1), (A)+(B16)+(B17.1), (A)+(B16)+(B18.1), (A)+(B16)+(B19), (A)+(B16)+(B20.1), (A)+(B16)+(B21.1), (A)+(B16)+(B22.1), (A)+(B16)+(B23.1), (A)+(B16)+(B24.1); (A)+(B16)+(B25), (A)+(B16)+(B26.1), (A)+(B16)+(B27.1), (A)+(B16)+(B28.1), (A)+(B16)+(B29), (A)+(B16)+(B29.1), (A)+(B16)+(B29.2), (A)+(B16)+(B29.3), (A)+(B16)+(B30.1), (A)+(B16)+(B31.1), (A)+(B16)+(B32.1), (A)+(B16)+(B32.2), (A)+(B16)+(B33), (A)+(B16)+(B34), (A)+(B16)+(B34.1), (A)+(B16)+(B34.2), (A)+(B16)+(B35), (A)+(B16)+(B36), (A)+(B16)+(B36.1), (A)+(B16)+(B36.2), (A)+(B16)+(B37), (A)+(B16)+(B37.1), (A)+(B16)+(B37.2), (A)+(B16)+(B38), (A)+(B16)+(B381), (A)+(B16)+(B38.2), (A)+(B16)+(B39), (A)+(B16)+(B39.1), (A)+(B16)+(B40), (A)+(B16)+(B40.1), (A)+(B16)+(B41), (A)+(B16)+(B41.1), (A)+(B16)+(B41.2), (A)+(B16)+(B42), (A)+(B16)+(B42.1), (A)+(B16)+(B42.2), (A)+(B16)+(B42.3), (A)+(B16)+(B43), (A)+(B16)+(B43.1), (A)+(B16)+(B44), (A)+(B16)+(B44.1), (A)+(B17.1)+(B18.1), (A)+(B17.1)+(B19), (A)+(B17.1)+(B20.1), (A)+(B17.1)+(B21.1), (A)+(B17.1)+(B22.1), (A)+(B17.1)+(B23.1), (A)+(B17.1)+(B24.1); (A)+(B17.1)+(B25), (A)+(B17.1)+(B26.1), (A)+(B17.1)+(B27.1), (A)+(B17.1)+(B28.1), (A)+(B17.1)+(B29), (A)+(B17.1)+(B29.1), (A)+(B17.1)+(B29.2), (A)+(B17.1)+(B29.3), (A)+(B17.1)+(B30.1), (A)+(B17.1)+(B31.1), (A)+(B17.1)+(B32.1), (A)+(B17.1)+(B32.2), (A)+(B17.1)+(B33), (A)+(B17.1)+(B34), (A)+(B17.1)+(B34.1), (A)+(B17.1)+(B34.2), (A)+(B17.1)+(B35), (A)+(B17.1)+(B36), (A)+(B17.1)+(B36.1), (A)+(B17.1)+(B36.2), (A)+(B17.1)+(B37), (A)+(B17.1)+(B37.1), (A)+(B17.1)+(B37.2), (A)+(B17.1)+(B38), (A)+(B17.1)+(B38.1), (A)+(B17.1)+(B38.2), (A)+(B17.1)+(B39), (A)+(B17.1)+(B39.1), (A)+(B17.1)+(B40), (A)+(B17.1)+(B40.1), (A)+(B17.1)+(B41), (A)+(B17.1)+(B41.1), (A)+(B17.1)+(B41.2), (A)+(B17.1)+(B42), (A)+(B17.1)+(B42.1), (A)+(B17.1)+(B42.2), (A)+(B17.1)+(B42.3), (A)+(B17.1)+(B43), (A)+(B17.1)+(B43.1), (A)+(B17.1)+(B44), (A)+(B17.1)+(B44.1), (A)+(B18.1)+(B19), (A)+(B18.1)+(B20.1), (A)+(B18.1)+(B21.1), (A)+(B18.1)+(B22.1), (A)+(B18.1)+(B23.1), (A)+(B18.1)+(B24.1); (A)+(B18.1)+(B25), (A)+(B18.1)+(B26.1), (A)+(B18.1)+(B27.1), (A)+(B18.1)+(B28.1), (A)+(B18.1)+(B29), (A)+(B18.1)+(B29.1), (A)+(B18.1)+(B29.2), (A)+(B18.1)+(B29.3), (A)+(B18.1)+(B30.1), (A)+(B18.1)+(B31.1), (A)+(B18.1)+(B32.1), (A)+(B18.1)+(B32.2), (A)+(B18.1)+(B33), (A)+(B18.1)+(B34), (A)+(B18.1)+(B34.1), (A)+(B18.1)+(B34.2), (A)+(B18.1)+(B35), (A)+(B18.1)+(B36), (A)+(B18.1)+(B36.1), (A)+(B18.1)+(B36.2), (A)+(B18.1)+(B37), (A)+(B18.1)+(B37.1), (A)+(B18.1)+(B37.2), (A)+(B18.1)+(B38), (A)+(B18.1)+(B38.1), (A)+(B18.1)+(B38.2), (A)+(B18.1)+(B39), (A)+(B18.1)+(B39.1), (A)+(B18.1)+(B40), (A)+(B18.1)+(B40.1), (A)+(B18.1)+(B41), (A)+(B18.1)+(B41.1), (A)+(B18.1)+(B41.2), (A)+(B18.1)+(B42), (A)+(B18.1)+(B42.1), (A)+(B18.1)+(B42.2), (A)+(B18.1)+(B42.3), (A)+(B18.1)+(B43), (A)+(B18.1)+(B43.1), (A)+(B18.1)+(B44), (A)+(B18.1)+(B44.1), (A)+(B19)+(B20.1), (A)+(B19)+(B21.1), (A)+(B19)+(B22.1), (A)+(B19)+(B23.1), (A)+(B19)+(B24.1); (A)+(B19)+(B25), (A)+(B19)+(B26.1), (A)+(B19)+(B27.1), (A)+(B19)+(B28.1), (A)+(B19)+(B29), (A)+(B19)+(B29.1), (A)+(B19)+(B29.2), (A)+(B19)+(B29.3), (A)+(B19)+(B30.1), (A)+(B19)+(B31.1), (A)+(B19)+(B32.1), (A)+

(B19)+(B32.2), (A)+(B19)+(B33), (A)+(B19)+(B34), (A)+(B19)+(B34.1), (A)+(B19)+(B34.2), (A)+(B19)+(B35), (A)+(B19)+(B36), (A)+(B19)+(B36.1), (A)+(B19)+(B36.2), (A)+(B19)+(B37), (A)+(B19)+(B37.1), (A)+(B19)+(B37.2), (A)+(B19)+(B38), (A)+(B19)+(B38.1), (A)+(B19)+(B38.2), (A)+(B19)+(B39), (A)+(B19)+(B39.1), (A)+(B19)+(B40), (A)+(B19)+(B40.1), (A)+(B19)+(B41), (A)+(B19)+(B41.1), (A)+(B19)+(B41.2), (A)+(B19)+(B42), (A)+(B19)+(B42.1), (A)+(B19)+(B42.2), (A)+(B19)+(B42.3), (A)+(B19)+(B43), (A)+(B19)+(B43.1), (A)+(B19)+(B44), (A)+(B19)+(B44.1), (A)+(B20.1)+(B21.1), (A)+(B20.1)+(B22.1), (A)+(B20.1)+(B23.1), (A)+(B20.1)+(B24.1); (A)+(B20.1)+(B25), (A)+(B20.1)+(B26.1), (A)+(B20.1)+(B27.1), (A)+(B20.1)+(B28.1), (A)+(B20.1)+(B29), (A)+(B20.1)+(B29.1), (A)+(B20.1)+(B29.2), (A)+(B20.1)+(B29.3), (A)+(B20.1)+(B30.1), (A)+(B20.1)+(B31.1), (A)+(B20.1)+(B32.1), (A)+(B20.1)+(B32.2), (A)+(B20)+(B33), (A)+(B20)+(B34), (A)+(B20)+(B34.1), (A)+(B20)+(B34.2), (A)+(B20)+(B35), (A)+(B20)+(B36), (A)+(B20)+(B36.1), (A)+(B20)+(B36.2), (A)+(B20)+(B37), (A)+(B20)+(B37.1), (A)+(B20)+(B37.2), (A)+(B20)+(B38), (A)+(B20)+(B38.1), (A)+(B20)+(B38.2), (A)+(B20)+(B39), (A)+(B20)+(B39.1), (A)+(B20)+(B40), (A)+(B20)+(B40.1), (A)+(B20)+(B41), (A)+(B20)+(B41.1), (A)+(B20)+(B41.2), (A)+(B20)+(B42), (A)+(B20)+(B42.1), (A)+(B20)+(B42.2), (A)+(B20)+(B42.3), (A)+(B20)+(B43), (A)+(B20)+(B43.1), (A)+(B20)+(B44), (A)+(B20)+(B44.1), (A)+(B21.1)+(B22.1), (A)+(B21.1)+(B23.1), (A)+(B21.1)+(B24.1); (A)+(B21.1)+(B25), (A)+(B21.1)+(B26.1), (A)+(B21.1)+(B27.1), (A)+(B21.1)+(B28.1), (A)+(B21.1)+(B29), (A)+(B21.1)+(B29.1), (A)+(B21.1)+(B29.2), (A)+(B21.1)+(B29.3), (A)+(B21.1)+(B30.1), (A)+(B21.1)+(B31.1), (A)+(B21.1)+(B32.1), (A)+(B21.1)+(B32.2), (A)+(B21.1)+(B33), (A)+(B21.1)+(B34), (A)+(B21.1)+(B34.1), (A)+(B21.1)+(B34.2), (A)+(B21.1)+(B35), (A)+(B21.1)+(B36), (A)+(B21.1)+(B36.1), (A)+(B21.1)+(B36.2), (A)+(B21.1)+(B37), (A)+(B21.1)+(B37.1), (A)+(B21.1)+(B37.2), (A)+(B21.1)+(B38), (A)+(B21.1)+(B38.1), (A)+(B21.1)+(B38.2), (A)+(B21.1)+(B39), (A)+(B21.1)+(B39.1), (A)+(B21.1)+(B40), (A)+(B21.1)+(B40.1), (A)+(B21.1)+(B41), (A)+(B21.1)+(B41.1), (A)+(B21.1)+(B41.2), (A)+(B21.1)+(B42), (A)+(B21.1)+(B42.1), (A)+(B21.1)+(B42.2), (A)+(B21.1)+(B42.3), (A)+(B21.1)+(B43), (A)+(B21.1)+(B43.1), (A)+(B21.1)+(B44), (A)+(B21.1)+(B44.1), (A)+(B22.1)+(B23.1), (A)+(B22.1)+(B24.1); (A)+(B22.1)+(B25), (A)+(B22.1)+(B26.1), (A)+(B22.1)+(B27.1), (A)+(B22.1)+(B28.1), (A)+(B22.1)+(B29), (A)+(B22.1)+(B29.1), (A)+(B22.1)+(B29.2), (A)+(B22.1)+(B29.3), (A)+(B22.1)+(B30.1), (A)+(B22.1)+(B31.1), (A)+(B22.1)+(B32.1), (A)+(B22.1)+(B32.2), (A)+(B22.1)+(B33), (A)+(B22.1)+(B34), (A)+(B22.1)+(B34.1), (A)+(B22.1)+(B34.2), (A)+(B22.1)+(B35), (A)+(B22.1)+(B36), (A)+(B22.1)+(B36.1), (A)+(B22.1)+(B36.2), (A)+(B22.1)+(B37), (A)+(B22.1)+(B37.1), (A)+(B22.1)+(B37.2), (A)+(B22.1)+(B38), (A)+(B22.1)+(B38.1), (A)+(B22.1)+(B38.2), (A)+(B22.1)+(B39), (A)+(B22.1)+(B39.1), (A)+(B22.1)+(B40), (A)+(B22.1)+(B40.1), (A)+(B22.1)+(B41), (A)+(B22.1)+(B41.1), (A)+(B22.1)+(B41.2), (A)+(B22.1)+(B42), (A)+(B22.1)+(B42.1), (A)+(B22.1)+(B42.2), (A)+(B22.1)+(B42.3), (A)+(B22.1)+(B43), (A)+(B22.1)+(B43.1), (A)+(B22.1)+(B44), (A)+(B22.1)+(B44.1), (A)+(B23.1)+(B24.1); (A)+(B23.1)+(B25), (A)+(B23.1)+(B26.1), (A)+(B23.1)+(B27.1), (A)+(B23.1)+(B28.1), (A)+(B23.1)+(B29), (A)+(B23.1)+(B29.1), (A)+(B23.1)+(B29.2), (A)+(B23.1)+(B29.3), (A)+(B23.1)+(B30.1), (A)+(B23.1)+(B31.1), (A)+(B23.1)+(B32.1), (A)+(B23.1)+(B32.2), (A)+(B23.1)+(B33), (A)+(B23.1)+(B34), (A)+(B23.1)+(B34.1), (A)+(B23.1)+(B34.2), (B35), (A)+(B23.1)+(B36), (A)+(B23.1)+(B36.1), (A)+(B23.1)+(B36.2), (A)+(B23.1)+(B37), (A)+(B23.1)+(B37.1), (A)+(B23.1)+(B37.2), (A)+(B23.1)+(B38), (A)+(B23.1)+(B38.1), (A)+(B23.1)+(B38.2), (A)+(B23.1)+(B39), (A)+(B23.1)+(B39.1), (A)+(B23.1)+(B40), (A)+(B23.1)+(B40.1), (A)+(B23.1)+(B41), (A)+(B23.1)+(B41.1), (A)+(B23.1)+(B41.2), (A)+(B23.1)+(B42), (A)+(B23.1)+(B42.1), (A)+(B23.1)+(B42.2), (A)+(B23.1)+(B42.3), (A)+(B23.1)+(B43), (A)+(B23.1)+(B43.1), (A)+(B23.1)+(B44), (A)+(B23.1)+(B44.1), (A)+(B24.1)+(B25), (A)+(B24.1)+(B26.1), (A)+(B24.1)+(B27.1), (A)+(B24.1)+(B28.1), (A)+(B24.1)+(B29), (A)+(B24.1)+(B29.1), (A)+(B24.1)+(B29.2), (A)+(B24.1)+(B29.3), (A)+(B24.1)+(B30.1), (A)+(B24.1)+(B31.1), (A)+(B24.1)+(B32.1), (A)+(B24.1)+(B32.2), (A)+(B24.1)+(B33), (A)+(B24.1)+(B34), (A)+(B24.1)+(B341), (A)+(B241)+(B34.2), (A)+(B24.1)+(B35), (A)+(B24.1)+(B36), (A)+(B24.1)+(B36.1), (A)+(B24.1)+(B36.2), (A)+(B24.1)+(B37), (A)+(B24.1)+(B37.1), (A)+(B24.1)+(B37.2), (A)+(B24.1)+(B38), (A)+(B24.1)+(B38.1), (A)+(B24.1)+(B38.2), (A)+(B24.1)+(B39), (A)+(B24.1)+(B39.1), (A)+(B24.1)+(B40), (A)+(B24.1)+(B40.1), (A)+(B24.1)+(B41), (A)+(B24.1)+(B41.1), (A)+(B24.1)+(B41.2), (A)+(B24.1)+(B42), (A)+(B24.1)+(B42.1), (A)+(B24.1)+(B42.2), (A)+(B24.1)+(B42.3), (A)+(B24.1)+(B43), (A)+(B24.1)+(B43.1), (A)+(B24.1)+(B44), (A)+(B24.1)+(B44.1), (A)+(B25)+(B26.1), (A)+(B25)+(B27.1), (A)+(B25)+(B28.1), (A)+(B25)+(B29), (A)+(B25)+(B29.1), (A)+(B25)+(B29.2), (A)+(B25)+(B29.3), (A)+(B25)+(B30.1), (A)+(B25)+(B31.1), (A)+(B25)+(B32.1), (A)+(B25)+(B32.2), (A)+(B25)+(B33), (A)+(B25)+(B34), (A)+(B25)+(B34.1), (A)+(B25)+(B34.2), (A)+(B25)+(B35), (A)+(B25)+(B36), (A)+(B25)+(B36.1), (A)+(B25)+(B36.2), (A)+(B25)+(B37), (A)+(B25)+(B37.1), (A)+(B25)+(B37.2), (A)+(B25)+(B38), (A)+(B25)+(B38.1), (A)+(B25)+(B38.2), (A)+(B25)+(B39), (A)+(B25)+(B39.1), (A)+(B25)+(B40), (A)+(B25)+(B40.1), (A)+(B25)+(B41), (A)+(B25)+(B41.1), (A)+(B25)+(B41.2), (A)+(B25)+(B42), (A)+(B25)+(B42.1), (A)+(B25)+(B42.2), (A)+(B25)+(B42.3), (A)+(B25)+(B43), (A)+(B25)+(B43.1), (A)+(B25)+(B44), (A)+(B25)+(B44.1), (A)+(B26.1)+(B27.1), (A)+(B26.1)+(B28.1), (A)+(B26.1)+(B29), (A)+(B26.1)+(B29.1), (A)+(B26.1)+(B29.2), (A)+(B26.1)+(B29.3), (A)+(B26.1)+(B30.1), (A)+(B26.1)+(B31.1), (A)+(B26.1)+(B32.1), (A)+(B26.1)+(B32.2), (A)+(B26.1)+(B33), (A)+(B26.1)+(B34), (A)+(B26.1)+(B34.1), (A)+(B26.1)+(B34.2), (A)+(B26.1)+(B35), (A)+(B26.1)+(B36), (A)+(B26.1)+(B361), (A)+(B26.1)+(B36.2), (A)+(B26.1)+(B37), (A)+(B26.1)+(B37.1), (A)+(B26.1)+(B37.2), (A)+(B26.1)+(B38), (A)+(B26.1)+(B38.1), (A)+(B26.1)+(B38.2), (A)+(B26.1)+(B39), (A)+(B26.1)+(B39.1), (A)+(B26.1)+(B40), (A)+(B26.1)+(B40.1), (A)+(B26.1)+(B41), (A)+(B26.1)+(B41.1), (A)+(B26.1)+(B41.2), (A)+(B26.1)+(B42), (A)+(B26.1)+(B42.1), (A)+(B26.1)+(B42.2), (A)+(B26.1)+(B42.3), (A)+(B26.1)+(B43), (A)+(B26.1)+(B43.1), (A)+(B26.1)+(B44), (A)+(B26.1)+(B44.1), (A)+(B27.1)+(B28.1), (A)+(B27.1)+(B29), (A)+(B27.1)+(B29.1), (A)+(B27.1)+(B29.2), (A)+(B27.1)+(B29.3), (A)+(B27.1)+(B30.1), (A)+(B27.1)+(B31.1), (A)+(B27.1)+(B32.1), (A)+(B27.1)+(B32.2), (A)+(B27.1)+(B33), (A)+(B27.1)+(B34), (A)+(B27.1)+(B34.1), (A)+(B27.1)+(B34.2), (A)+(B27.1)+(B35), (A)+(B27.1)+(B36), (A)+(B27.1)+(B36.1), (A)+(B27.1)+(B36.2), (A)+(B27.1)+(B37), (A)+(B27.1)+(B37.1), (A)+(B27.1)+(B37.2), (A)+(B27.1)+(B38), (A)+(B27.1)+(B38.1), (A)+(B27.1)+(B38.2), (A)+(B27.1)+(B39), (A)+(B271)+(B39.1), (A)+

(B27.1)+(B40), (A)+(B27.1)+(B40.1), (A)+(B27.1)+(B41), (A)+(B27.1)+(B41.1), (A)+(B27.1)+(B41.2), (A)+(B27.1)+(B42), (A)+(B27.1)+(B42.1), (A)+(B27.1)+(B42.2), (A)+(B27.1)+(B42.3), (A)+(B27.1)+(B43), (A)+(B27.1)+(B43.1), (A)+(B27.1)+(B44), (A)+(B27.1)+(B44.1), (A)+(B28.1)+(B29), (A)+(B28.1)+(B29.1), (A)+(B28.1)+(B29.2), (A)+(B28.1)+(B29.3), (A)+(B28.1)+(B30.1), (A)+(B28.1)+(B31.1), (A)+(B28.1)+(B32.1), (A)+(B28.1)+(B32.2), (A)+(B28.1)+(B33), (A)+(B28.1)+(B34), (A)+(B28.1)+(B34.1), (A)+(B28.1)+(B34.2), (A)+(B28.1)+(B35), (A)+(B28.1)+(B36), (A)+(B28.1)+(B36.1), (A)+(B28.1)+(B36.2), (A)+(B28.1)+(B37), (A)+(B28.1)+(B37.1), (A)+(B28.1)+(B37.2), (A)+(B28.1)+(B38), (A)+(B28.1)+(B38.1), (A)+(B28.1)+(B38.2), (A)+(B28.1)+(B39), (A)+(B28.1)+(B39.1), (A)+(B28.1)+(B40), (A)+(B28.1)+(B40.1), (A)+(B28.1)+(B41), (A)+(B28.1)+(B41.1), (A)+(B28.1)+(B41.2), (A)+(B28.1)+(B42), (A)+(B28.1)+(B42.1), (A)+(B28.1)+(B42.2), (A)+(B28.1)+(B42.3), (A)+(B28.1)+(B43), (A)+(B28.1)+(B43.1), (A)+(B27.1)+(B44), (A)+(B27.1)+(B44.1), (A)+(B29)+(B30.1), (A)+(B29)+(B31.1), (A)+(B29)+(B32.1), (A)+(B29)+(B32.2), (A)+(B29)+(B33), (A)+(B29)+(B34), (A)+(B29)+(B34.1), (A)+(B29)+(B34.2), (A)+(B29)+(B35), (A)+(B29)+(B36), (A)+(B29)+(B36.1), (A)+(B29)+(B36.2), (A)+(B29)+(B37), (A)+(B29)+(B37.1), (A)+(B29)+(B37.2), (A)+(B29)+(B38), (A)+(B29)+(B38.1), (A)+(B29)+(B38.2), (A)+(B29)+(B39), (A)+(B29)+(B39.1), (A)+(B29)+(B40), (A)+(B29)+(B40.1), (A)+(B29)+(B41), (A)+(B29)+(B41.1), (A)+(B29)+(B41.2), (A)+(B29)+(B42), (A)+(B29)+(B42.1), (A)+(B29)+(B42.2), (A)+(B29)+(B42.3), (A)+(B29)+(B43), (A)+(B29)+(B43.1), (A)+(B29)+(B44), (A)+(B29)+(B44.1), (A)+(B29.1)+(B30.1), (A)+(B29.1)+(B31.1), (A)+(B29.1)+(B32.1), (A)+(B29.1)+(B32.2), (A)+(B29.1)+(B33), (A)+(B29.1)+(B34), (A)+(B29.1)+(B34.1), (A)+(B29.1)+(B34.2), (A)+(B29.1)+(B35), (A)+(B29.1)+(B36), (A)+(B29.1)+(B36.1), (A)+(B29.1)+(B36.2), (A)+(B29.1)+(B37), (A)+(B29.1)+(B37.1), (A)+(B29.1)+(B37.2), (A)+(B29.1)+(B38), (A)+(B29.1)+(B38.1), (A)+(B29.1)+(B38.2), (A)+(B29.1)+(B39), (A)+(B29.1)+(B39.1), (A)+(B29.1)+(B40), (A)+(B29.1)+(B40.1), (A)+(B29.1)+(B41), (A)+(B29.1)+(B41.1), (A)+(B29.1)+(B41.2), (A)+(B29.1)+(B42), (A)+(B29.1)+(B42.1), (A)+(B29.1)+(B42.2), (A)+(B29.1)+(B42.3), (A)+(B29.1)+(B43), (A)+(B29.1)+(B43.1), (A)+(B29.1)+(B44), (A)+(B29.1)+(B44.1), (A)+(B29.2)+(B30.1), (A)+(B29.2)+(B31.1), (A)+(B29.2)+(B32.1), (A)+(B29.2)+(B32.2), (A)+(B29.2)+(B33), (A)+(B29.2)+(B34), (A)+(B29.2)+(B34.1), (A)+(B29.2)+(B34.2), (A)+(B29.2)+(B35), (A)+(B29.2)+(B36), (A)+(B29.2)+(B36.1), (A)+(B29.2)+(B36.2), (A)+(B29.2)+(B37), (A)+(B29.2)+(B37.1), (A)+(B29.2)+(B37.2), (A)+(B29.2)+(B38), (A)+(B29.2)+(B38.1), (A)+(B29.2)+(B382), (A)+(B29.2)+(B39), (A)+(B29.2)+(B39.1), (A)+(B29.2)+(B40), (A)+(B29.2)+(B40.1), (A)+(B29.2)+(B41), (A)+(B29.2)+(B41.1), (A)+(B29.2)+(B41.2), (A)+(B29.2)+(B42), (A)+(B29.2)+(B42.1), (A)+(B29.2)+(B42.2), (A)+(B29.2)+(B42.3), (A)+(B29.2)+(B43), (A)+(B29.2)+(B43.1), (A)+(B29.2)+(B44), (A)+(B29.2)+(B44.1), (A)+(B29.3)+(B30.1), (A)+(B29.3)+(B31.1), (A)+(B29.3)+(B32.1), (A)+(B29.3)+(B32.2), (A)+(B29.3)+(B33), (A)+(B29.3)+(B34), (A)+(B29.3)+(B34.1), (A)+(B29.3)+(B34.2), (A)+(B29.3)+(B35), (A)+(B29.3)+(B36), (A)+(B29.3)+(B36.1), (A)+(B29.3)+(B36.2), (A)+(B29.3)+(B37), (A)+(B29.3)+(B37.1), (A)+(B29.3)+(B37.2), (A)+(B29.3)+(B38), (A)+(B29.3)+(B38.1), (A)+(B29.3)+(B38.2), (A)+(B29.3)+(B39), (A)+(B29.3)+(B39.1), (A)+(B29.3)+(B40), (A)+(B29.3)+(B40.1), (A)+(B29.3)+(B41), (A)+(B29.3)+(B41.1), (A)+(B29.3)+(B41.2), (A)+(B29.3)+(B42), (A)+(B29.3)+(B42.1), (A)+(B29.3)+(B42.2), (A)+(B29.3)+(B42.3), (A)+(B29.3)+(B43), (A)+(B29.3)+(B43.1), (A)+(B29.3)+(B44), (A)+(B29.3)+(B44.1), (A)+(B30.2)+(B31.1), (A)+(B30.2)+(B32.1), (A)+(B30.2)+(B32.2), (A)+(B30.2)+(B33), (A)+(B30.2)+(B34), (A)+(B30.2)+(B34.1), (A)+(B30.2)+(B34.2), (A)+(B30.2)+(B35), (A)+(B30.2)+(B36), (A)+(B30.2)+(B36.1), (A)+(B30.2)+(B36.2), (A)+(B30.2)+(B37), (A)+(B30.2)+(B37.1), (A)+(B30.2)+(B37.2), (A)+(B30.2)+(B38), (A)+(B30.2)+(B38.1), (A)+(B30.2)+(B38.2), (A)+(B30.2)+(B39), (A)+(B30.2)+(B39.1), (A)+(B30.2)+(B40), (A)+(B30.2)+(B40.1), (A)+(B30.2)+(B41), (A)+(B30.2)+(B41.1), (A)+(B30.2)+(B41.2), (A)+(B30.2)+(B42), (A)+(B30.2)+(B42.1), (A)+(B30.2)+(B42.2), (A)+(B30.2)+(B42.3), (A)+(B30.2)+(B43), (A)+(B30.2)+(B43.1), (A)+(B30.2)+(B44), (A)+(B30.2)+(B44.1), (A)+(B31.2)+(B32.1), (A)+(B31.2)+(B32.2), (A)+(B31.2)+(B33), (A)+(B31.2)+(B34), (A)+(B31.2)+(B34.1), (A)+(B31.2)+(B34.2), (A)+(B31.2)+(B35), (A)+(B31.2)+(B36), (A)+(B31.2)+(B36.1), (A)+(B31.2)+(B36.2), (A)+(B31.2)+(B37), (A)+(B31.2)+(B37.1), (A)+(B31.2)+(B37.2), (A)+(B31.2)+(B38), (A)+(B31.2)+(B38.1), (A)+(B31.2)+(B38.2), (A)+(B31.2)+(B39), (A)+(B31.2)+(B39.1), (A)+(B31.2)+(B40), (A)+(B31.2)+(B40.1), (A)+(B31.2)+(B41), (A)+(B31.2)+(B41.1), (A)+(B31.2)+(B41.2), (A)+(B31.2)+(B42), (A)+(B31.2)+(B42.1), (A)+(B31.2)+(B42.2), (A)+(B31.2)+(B42.3), (A)+(B31.2)+(B43), (A)+(B31.2)+(B43.1), (A)+(B31.2)+(B44), (A)+(B31.2)+(B44.1), (A)+(B32.1)+(B33), (A)+(B32.1)+(B34), (A)+(B32.1)+(B34.1), (A)+(B32.1)+(B34.2), (A)+(B32.1)+(B35), (A)+(B32.1)+(B36), (A)+(B32.1)+(B36.1), (A)+(B32.1)+(B36.2), (A)+(B32.1)+(B37), (A)+(B32.1)+(B37.1), (A)+(B32.1)+(B37.2), (A)+(B32.1)+(B38), (A)+(B32.1)+(B38.1), (A)+(B32.1)+(B38.2), (A)+(B32.1)+(B39), (A)+(B32.1)+(B39.1), (A)+(B32.1)+(B40), (A)+(B32.1)+(B40.1), (A)+(B32.1)+(B41), (A)+(B32.1)+(B41.1), (A)+(B32.1)+(B41.2), (A)+(B32.1)+(B42), (A)+(B32.1)+(B42.1), (A)+(B32.1)+(B42.2), (A)+(B32.1)+(B42.3), (A)+(B32.1)+(B43), (A)+(B32.1)+(B43.1), (A)+(B32.1)+(B44), (A)+(B32.1)+(B44.1), (A)+(B32.2)+(B33), (A)+(B32.2)+(B34), (A)+(B32.2)+(B34.1), (A)+(B32.2)+(B34.2), (A)+(B32.2)+(B35), (A)+(B32.2)+(B36), (A)+(B32.2)+(B36.1), (A)+(B32.2)+(B36.2), (A)+(B32.2)+(B37), (A)+(B32.2)+(B37.1), (A)+(B32.2)+(B37.2), (A)+(B32.2)+(B38), (A)+(B32.2)+(B38.1), (A)+(B32.2)+(B38.2), (A)+(B32.2)+(B39), (A)+(B32.2)+(B39.1), (A)+(B32.2)+(B40), (A)+(B32.2)+(B40.1), (A)+(B32.2)+(B41), (A)+(B32.2)+(B41.1), (A)+(B32.2)+(B41.2), (A)+(B32.2)+(B42), (A)+(B32.2)+(B42.1), (A)+(B32.2)+(B42.2), (A)+(B32.2)+(B42.3), (A)+(B32.2)+(B43), (A)+(B32.2)+(B43.1), (A)+(B32.2)+(B44), (A)+(B32.2)+(B44.1), (A)+(B33)+(B34), (A)+(B33)+(B34.1), (A)+(B33)+(B34.2), (A)+(B33)+(B35), (A)+(B33)+(B36), (A)+(B33)+(B36.1), (A)+(B33)+(B36.2), (A)+(B33)+(B37), (A)+(B33)+(B37.1), (A)+(B33)+(B37.2), (A)+(B33)+(B38), (A)+(B33)+(B38.1), (A)+(B33)+(B38.2), (A)+(B33)+(B39), (A)+(B33)+(B39.1), (A)+(B33)+(B40), (A)+(B33)+(B40.1), (A)+(B33)+(B41), (A)+(B33)+(B41.1), (A)+(B33)+(B41.2), (A)+(B33)+(B42), (A)+(B33)+(B42.1), (A)+(B33)+(B42.2), (A)+(B33)+(B42.3), (A)+(B33)+(B43), (A)+(B33)+(B43.1), (A)+(B33)+(B44), (A)+(B33)+(B44.1), (A)+(B34)+(B35), (A)+(B34)+(B36), (A)+(B34)+(B36.1), (A)+(B34)+(B36.2), (A)+(B34)+(B37), (A)+(B34)+(B37.1), (A)+(B34)+(B37.2), (A)+(B34)+(B38), (A)+(B34)+(B38.1), (A)+(B34)+(B38.2), (A)+(B34)+(B39), (A)+(B34)+(B39.1), (A)+(B34)+(B40), (A)+(B34)+(B40.1), (A)+(B34)+(B41), (A)+(B34)+(B41.1), (A)+(B34)+(B41.2), (A)+(B34)+(B42), (A)+(B34)+(B42.1), (A)+(B34)+(B42.2), (A)+(B34)+(B42.3), (A)+(B34)+(B43), (A)+(B34)+(B43.1), (A)+(B34)+(B44), (A)+(B34)+(B44.1),
(A)+(B34.1)+(B35), (A)+(B34.1)+(B36), (A)+(B34.1)+(B36.1), (A)+(B34.1)+(B36.2), (A)+(B34.1)+(B37), (A)+(B34.1)+(B37.1), (A)+(B34.1)+(B37.2), (A)+(B34.1)+(B38), (A)+(B34.1)+(B38.1), (A)+(B34.1)+(B38.2), (A)+(B34.1)+(B39), (A)+(B34.1)+(B39.1), (A)+(B34.1)+(B40), (A)+(B34.1)+(B40.1), (A)+(B34.1)+(B41), (A)+(B34.1)+(B41.1), (A)+(B34.1)+(B41.2), (A)+(B34.1)+(B42), (A)+(B34.1)+(B42.1), (A)+(B34.1)+(B42.2), (A)+(B34.1)+(B42.3), (A)+(B34.1)+(B43), (A)+(B34.1)+(B43.1), (A)+(B34.1)+(B44), (A)+(B34.1)+(B44.1),
(A)+(B34.2)+(B35), (A)+(B34.2)+(B36), (A)+(B34.2)+(B36.1), (A)+(B34.2)+(B36.2), (A)+(B34.2)+(B37), (A)+(B34.2)+(B37.1), (A)+(B34.2)+(B37.2), (A)+(B34.2)+(B38), (A)+(B34.2)+(B38.1), (A)+(B34.2)+(B38.2), (A)+(B34.2)+(B39), (A)+(B34.2)+(B39.1), (A)+(B34.2)+(B40), (A)+(B34.2)+(B40.1), (A)+(B34.2)+(B41), (A)+(B34.2)+(B41.1), (A)+(B34.2)+(B41.2), (A)+(B34.2)+(B42), (A)+(B34.2)+(B42.1), (A)+(B34.2)+(B42.2), (A)+(B34.2)+(B42.3), (A)+(B34.2)+(B43), (A)+(B34.2)+(B43.1), (A)+(B34.2)+(B44), (A)+(B34.2)+(B44.1),
(A)+(B35)+(B36), (A)+(B35)+(B36.1), (A)+(B35)+(B36.2), (A)+(B35)+(B37), (A)+(B35)+(B37.1), (A)+(B35)+(B37.2), (A)+(B35)+(B38), (A)+(B35)+(B38.1), (A)+(B35)+(B38.2), (A)+(B35)+(B39), (A)+(B35)+(B39.1), (A)+(B35)+(B40), (A)+(B35)+(B40.1), (A)+(B35)+(B41), (A)+(B35)+(B41.1), (A)+(B35)+(B41.2), (A)+(B35)+(B42), (A)+(B35)+(B42.1), (A)+(B35)+(B42.2), (A)+(B35)+(B42.3), (A)+(B35)+(B43), (A)+(B35)+(B43.1), (A)+(B35)+(B44), (A)+(B35)+(B44.1),
(A)+(B36)+(B37), (A)+(B36)+(B37.1), (A)+(B36)+(B37.2), (A)+(B36)+(B38), (A)+(B36)+(B38.1), (A)+(B36)+(B38.2), (A)+(B36)+(B39), (A)+(B36)+(B39.1), (A)+(B36)+(B40), (A)+(B36)+(B40.1), (A)+(B36)+(B41), (A)+(B36)+(B41.1), (A)+(B36)+(B41.2), (A)+(B36)+(B42), (A)+(B36)+(B42.1), (A)+(B36)+(B42.2), (A)+(B36)+(B42.3), (A)+(B36)+(B43), (A)+(B36)+(B43.1), (A)+(B36)+(B44), (A)+(B36)+(B44.1),
(A)+(B36.2)+(B37), (A)+(B36.2)+(B37.1), (A)+(B36.2)+(B37.2), (A)+(B36.2)+(B38), (A)+(B36.2)+(B38.1), (A)+(B36.2)+(B38.2), (A)+(B36.2)+(B39), (A)+(B36.2)+(B39.1), (A)+(B36.2)+(B40), (A)+(B36.2)+(B40.1), (A)+(B36.2)+(B41), (A)+(B36.2)+(B41.1), (A)+(B36.2)+(B41.2), (A)+(B36.2)+(B42), (A)+(B36.2)+(B42.1), (A)+(B36.2)+(B42.2), (A)+(B36.2)+(B42.3), (A)+(B36.2)+(B43), (A)+(B36.2)+(B43.1), (A)+(B36.2)+(B44), (A)+(B36.2)+(B44.1), (A)+(B37)+(B38), (A)+(B37)+(B38.1), (A)+(B37)+(B38.2), (A)+(B37)+(B39), (A)+(B37)+(B39.1), (A)+(B37)+(B40), (A)+(B37)+(B40.1), (A)+(B37)+(B41), (A)+(B37)+(B41.1), (A)+(B37)+(B41.2), (A)+(B37)+(B42), (A)+(B37)+(B42.1), (A)+(B37)+(B42.2), (A)+(B37)+(B42.3), (A)+(B37)+(B43), (A)+(B37)+(B43.1), (A)+(B37)+(B44), (A)+(B37)+(B44.1),
(A)+(B37.2)+(B38), (A)+(B37.2)+(B38.1), (A)+(B37.2)+(B38.2), (A)+(B37.2)+(B39), (A)+(B37.2)+(B39.1), (A)+(B37.2)+(B40), (A)+(B37.2)+(B40.1), (A)+(B37.2)+(B41), (A)+(B37.2)+(B41.1), (A)+(B37.2)+(B41.2), (A)+(B37.2)+(B42), (A)+(B37.2)+(B42.1), (A)+(B37.2)+(B42.2), (A)+(B37.2)+(B42.3), (A)+(B37.2)+(B43), (A)+(B37.2)+(B43.1), (A)+(B37.2)+(B44), (A)+(B37.2)+(B44.1),
(A)+(B38)+(B39), (A)+(B38)+(B39.1), (A)+(B38)+(B40), (A)+(B38)+(B40.1), (A)+(B38)+(B41), (A)+(B38)+(B41.1), (A)+(B38)+(B41.2), (A)+(B38)+(B42), (A)+(B38)+(B42.1), (A)+(B38)+(B42.2), (A)+(B38)+(B42.3), (A)+(B38)+(B43), (A)+(B38)+(B43.1), (A)+(B38)+(B44), (A)+(B38)+(B44.1),
(A)+(B38.2)+(B39), (A)+(B38.2)+(B39.1), (A)+(B38.2)+(B40), (A)+(B38.2)+(B40.1), (A)+(B38.2)+(B41), (A)+(B38.2)+(B41.1), (A)+(B38.2)+(B41.2), (A)+(B38.2)+(B42), (A)+(B38.2)+(B42.1), (A)+(B38.2)+(B42.2), (A)+(B38.2)+(B42.3), (A)+(B38.2)+(B43), (A)+(B38.2)+(B43.1), (A)+(B38.2)+(B44), (A)+(B38.2)+(B44.1),
(A)+(B39)+(B40), (A)+(B39)+(B40.1), (A)+(B39)+(B41), (A)+(B39)+(B41.1), (A)+(B39)+(B41.2), (A)+(B39)+(B42), (A)+(B39)+(B42.1), (A)+(B39)+(B42.2), (A)+(B39)+(B42.3), (A)+(B39)+(B43), (A)+(B39)+(B43.1), (A)+(B39)+(B44), (A)+(B39)+(B44.1),
(A)+(B39.1)+(B40), (A)+(B39.1)+(B40.1), (A)+(B39.1)+(B41), (A)+(B39.1)+(B41.1), (A)+(B39.1)+(B41.2), (A)+(B39.1)+(B42), (A)+(B39.1)+(B42.1), (A)+(B39.1)+(B42.2), (A)+(B39.1)+(B42.3), (A)+(B39.1)+(B43), (A)+(B39.1)+(B43.1), (A)+(B39.1)+(B44), (A)+(B39.1+(B44.1),
(A)+(B40)+(B41), (A)+(B40)+(B41.1), (A)+(B40)+(B41.2), (A)+(B40)+(B42), (A)+(B40)+(B42.1), (A)+(B40)+(B42.2), (A)+(B40)+(B42.3), (A)+(B40)+(B43), (A)+(B40)+(B43.1), (A)+(B40)+(B44), (A)+(B40)+(B44.1),
(A)+(B40.1)+(B41), (A)+(B40.1)+(B41.1), (A)+(B40.1)+(B41.2), (A)+(B40.1)+(B42), (A)+(B40.1)+(B42.1), (A)+(B40.1)+(B42.2), (A)+(B40.1)+(B42.3), (A)+(B40.1)+(B43), (A)+(B40.1)+(B43.1), (A)+(B40.1)+(B44), (A)+(B40.1)+(B44.1),
(A)+(B41)+(B42), (A)+(B41)+(B42.1), (A)+(B41)+(B42.2), (A)+(B41)+(B42.3), (A)+(B41)+(B43), (A)+(B41)+(B43.1), (A)+(B41)+(B44), (A)+(B41)+(B44.1),
(A)+(B41.2)+(B42), (A)+(B41.2)+(B42.1), (A)+(B41.2)+(B42.2), (A)+(B41.2)+(B42.3), (A)+(B41.2)+(B43), (A)+(B41.2)+(B43.1),
(A)+(B42)+(B43), (A)+(B42)+(B43.1), (A)+(B42)+(B44), (A)+(B42)+(B44.1), (A)+(B43)+(B44), (A)+(B43)+(B44.1) and (A)+(B43.1)+(B44), (A)+(B43.1)+(B44.1),
wherein compound (A) in each case is selected from the list of compounds of table 1 (compounds A1 to A127) and the (B) herbicides are defined as set forth above.

Therefore, another object of the invention is the advantageous use of the above herbicidal combinations of selective weed control in turf or lawn. The combinations are valuable because they do not damage the turf grass substantially, preferably when the turf grasses belong to an established turf or lawn.

In many cases the combinations are surprisingly as selective as or even better selective in turf or lawn than the compounds (A) or (B) alone.

Another advantageous property found for the combination according to the invention of herbicides (A) and (B) is that the active compounds (A) and (B) are compatible with one another, i.e. they can be used together without substantial chemical incompatibilities of the active compounds (A) and/or (B) resulting in a decomposition of one or more active compounds. A reduction of the active compound content in formulations or spray liquors is thus avoided. The favorable compatibility also extends to the biological properties of the active compounds when applied in combination. Thus, antagonistic effects in the control of harmful plants are generally not observed with the active compound combinations according to the invention. Accordingly, the active compounds (A) and (B) are particularly suitable for joint application or application additionally with further active crop protection agents or agrochemicals. The possible combined application allows advantageous effects to be utilized, such as, for example, the widening of the spectrum of the harmful plants to be controlled or to be combated in an application, a reduction of the application rate of the individual herbicides (A) and/or (B) compared to the respective application rate of the herbicide in question in an individual application. Thus, the degradation properties of the active compounds can be influenced, and more favorable conditions for the replanting of crop plants can be achieved. A further advantage consists in the fact that the development of resistances of harmful plants to the active compounds can frequently be reduced substantially or avoided by combinations of active compounds having a different mechanism of action.

In particular, surprisingly, there are also superadditive (=synergistic) effects in the combined application of the active compounds (A) and (B) with a relatively large number of economically important harmful plants. Here, the activity of the combination is stronger than the expected sum of the activities of the individual herbicides employed.

The synergistic effects allow the application rate to be reduced further, a broader spectrum of broad-leaved weeds and weed grasses to be controlled, a more rapid onset of the herbicidal action, a longer persistency, a better control of the harmful plants with only one or a few applications and a widening of the application period possible. To some extent, by using the compositions, the amount of harmful ingredients, such as nitrogen or oleic acid, and their introduction into the soil are also likewise reduced.

The abovementioned properties and advantages are desired for weed control practice to keep agricultural crops free of unwanted competing plants, and thus to ensure and/or increase yield levels from the qualitative and quantitative angle. These novel combinations markedly exceed the technical state of the art with a view to the properties described.

The synergistic effects are observed when the active compounds (A) and (B) are applied together; however, they may frequently also occur when the compounds are applied as a split application over time. Another possibility is the application of the herbicides (A) or (B) or the herbicide combinations (A) and (B) in a plurality of portions (sequential application). For example, one or more pre-emergence applications may be followed by a post-emergence application, or an early post-emergence application may be followed by applications at medium or late post-emergence. Preferred is the simultaneous or nearly simultaneous application of the active compounds of the combination in question, if appropriate in a plurality of portions. However, it is also possible to apply the individual active compounds of a combination at different times, which may be advantageous in the individual case. It is also possible to integrate other crop protection agents, such as, for example, the other active compounds mentioned (other herbicides, fungicides, insecticides, acaricides, etc.) and/or various auxiliaries, adjuvants and/or fertilizer applications in the system of application.

Application by the pre-emergence or post-emergence method is, depending on the context in which the terms are used, to be understood as meaning the application of the active compounds before or after the point in time when the harmful plants become visible above the ground, respectively, or the application of the active compounds against the harmful plants before the emergence of the crop plants and after the emergence of the crop plants, respectively.

Some of the herbicidal combinations are novel and are thus another object of the invention together with compositions comprising said combinations. Particularly, combinations are considered novel, which comprise a combination of a compound of the above defined formula (I) or salt thereof, selected from the group of compounds (A1) to (A127) or salts thereof, preferably the compounds (A21) and (A22) and mixtures thereof, in combination with a compound (B) selected from the group consisting of (B5) Bromoxynil or esters thereof, such as (B5.1) Bromoxynil, (B5.2) Bromoxynil-heptanoate, (B5.3) Bromoxyniloctanoate,
(B8) Ethoxysulfuron or salts thereof, such as (B8.1) Ethoxysulfuron, (B8.2) Ethoxysulfuron-sodium,
(B10) Fatty acids, such as (B10.1) acetic acid, (B10.2) propionic acid, (B10.3) butanoic acid, (B10.4) pentanoic acid, (B10.5) hexanoic acid, (B10.6) heptanoic acid, (B10.7) octanoic acid, (B10.8) nonanoic acid, (B10.9) decanoic acid, (B10.10) undecanoic acid, (B10.11) dodecanoic acid, preferably $C_8$-$C_{12}$-fatty acids, more preferably (B10.8) nonanoic acid and (B10.9) decanoic acid,
(B15) Mesosulfuron and esters or salts thereof, such as (B15.1) Mesosulfuron, (B15.2) Mesosulfuron-methyl,
(B16) Metosulam,
(B25) *Sclerotinia* (biological herbicides),
(B34) Mecoprop and Mecoprop-P, and esters and salts thereof, such as (34.1) Mecoprop and esters and salts thereof, (34.2) Mecoprop-P and esters and salts thereof. (34.3) Mecoprop, (34.4) Mecoprop-P, (34.5) Mecoprop-sodium, (34.6) Mecoprop-butotyl, (34.7) Mecoprop-P, (34.8) Mecoprop-P-sodium, (34.9) Mecoprop-P-potassium, (34.10) Mecoprop-P-butotyl, (34.11) Mecoprop-P-2-ethyl-hexyl,
(B35) MCPA and esters and salts thereof, such as (35.1) MCPA, (35.2) MCPA-sodium, (35.3) MCPA-potassium, (35.4) MCPA-dimethylammonium, (35.5) Mecoprop-P-2-ethyl-hexyl,
(B36) Fenoxaprop and esters and salts thereof, such as (36.1) Fenoxaprop, (36.2) Fenoxaprop-ethyl, and
(B37) Fenoxaprop-P and esters and salts thereof, such as (36.1) Fenoxaprop-P and (37.2) Fenoxaprop-P-ethyl.

The above specific combinations per se and compositions comprising them are thus also object of the invention.

The herbicides (A), optionally in combination with herbicides (B), can also be applied together with other type (C) active ingredients useful in the treatment of turf or lawn. The herbicides (A), optionally in combination with herbicides (B), can also be applied together with other type (C) active ingredients useful in the treatment of lawn or turf. Type (C) active ingredients useful in the treatment of lawn or turf can be, for instance, insecticides, acaricides, fungicides, safeners, fertilizers and/or growth regulators or nutrients useful for treating lawn or turf against phytopathogenic diseases or for growth regulation or growth promotion of lawn or turf.

Because of the valuable properties of the novel herbicidal combinations they are not only useful for selective weed control in turf or lawn but also generally useful for weed control in non-crop areas or in crops such as plantation crops or other crops where the compounds (A) and (B) are known to be applicable.

Fungicidally active compounds which can be used in combination with the herbicide combinations according to the invention are preferably commercially available active compounds, for example (analogously to the herbicides, the compounds are generally referred to by their common names):
2-phenylphenol; 8-hydroxyquinoline sulfate; acibenzolar-S-methyl; actinovate; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; binapacryl; biphenyl; bitertanol; blasticidin-S; boscalid; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)cycloheptanol; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]methyl]-.alpha.-(methoxymethylene)benzeneacetate; methyl 2-[2-[3-(4-chlorophenyl)-1-methyl-allylideneaminooxymethyl]phenyl]-3-methoxyacrylate; metiram; metominostrobin; metrafenone; metsulfovax; mildiomycin; monopotassium carbonate; myclobutanil; myclozolin; nabam, N-(3-ethyl-3,5,5-trimethylcyclohexyl)-3-formylamino-2-hydroxy-benzamide; N-(6-methoxy-3-pyridinyl)cyclopropanecarboxamide; N-butyl-8-(1,1-dimethylethyl)-1-oxaspiro[4.5]decan-3-amine; natamycin; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; penthiopyrad; phosdiphen; phthalide; picobenzamid; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrroInitrine; quinconazole; quinoxyfen; quintozene; silthiofam; simeconazole; sodium tetrathiocarbonate; spiroxamine; sulfur; tebuconazole; tecloftalam; tecnazene; tetcyclacis; tetraconazole; thiabendazole; thicyofen; thifluzamide; thiophanate-methyl; thiram; tiadinil; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)pyridine; 2,4-dihydro-5-methoxy-2-methyl-4-[[[[1-[3-(trifluoro-methyl)phenyl]ethylidene]amino]oxy]methyl]phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; 3-[(3-bromo-6-fluoro-2-methyl-1H-indol-1-yl)sulfonyl]-N,N-dimethyl-1H-1,2,4-triazole-1-sulfonamide; copper salts and copper preparations, such as Bordeaux mixture; copper hydroxide; copper naphthenate; copper oxychloride; copper sulfate; cufraneb; copper(I) oxide; mancopper; oxine-copper.

Preferred fungicides are selected from the group consisting of benalaxyl, bitertanol, bromuconazole, captafol, carbendazim, carpropamid, cyazofamid, cyproconazole, diethofencarb, edifenphos, fenpropimorph, fentine, fluquinconazole, fosetyl, fluoroimide, folpet, iminoctadine, iprodionem, iprovalicarb, kasugamycin, maneb, nabam, pencycuron, prochloraz, propamocarb, propineb, pyrimethanil, spiroxamine, quintozene, tebuconazole, tolylfluanid, triadimefon, triadimenol, trifloxystrobin, zineb.

Insecticidal, acaricidal, nematicidal, miticidal and related active compounds are, for example (analogously to the herbicides and fungicides, the compounds are, if possible, referred to by their common names):

alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum), DDT, indoxacarb, acetamiprid, clothianidin, dinotefuran, imidacloprid, nitenpyram, nithiazine, thiacloprid, thiamethoxam, nicotine, bensultap, cartap, camphechlor, chlordane, endosulfan, gamma-HCH, HCH, heptachlor, lindane, methoxychlor spinosad, acetoprole, ethiprole, fipronil, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacyrl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1), flonicamid, amitraz, propargite, N2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7), thiocyclam hydrogen oxalate, thiosultap-sodium, azadirachtin, *Bacillus* spec., *Beauveria* spec., codlemone, *Metarrhizium* spec., *Paecilomyces* spec., thuringiensin, *Verticillium* spec., aluminum phosphide, methyl bromide, sulfuryl fluoride, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin.

Insecticides which may preferably be used together with the herbicides are, for example, the following:
acetamiprid, acrinathrin, aldicarb, amitraz, acinphos-methyl, bifenthrin, cyfluthrin, β-cyfluthrin, carbaryl, cypermethrin, deltamethrin, endosulfan, ethoprophos, fenamiphos, fenthion, fipronil, imidacloprid, methamidophos, methiocarb, niclosamide, oxydemeton-methyl, prothiophos, silafluofen, thiacloprid, thiodicarb, tralomethrin, triazophos, trichlorfon, triflumuron, terbufos, fonofos, phorate, chlorpyriphos, carbofuran, tefluthrin.

Preferred mixtures comprising insecticidal active ingredients are for example:
Preferred are combinations of a compound (A) selected from the list of compounds of table 1 (compounds A1 to A127) and an insecticide (C)
(A)+(C1) imidacloprid
(A)+(C2) thiametoxam
(A)+(C3) imidacloprid
(A)+(C4) fipronil
(A)+(C5) bifenthrin Preferred are combinations of a compound (A) selected from the list of compounds of table 1 (compounds A1 to A127) and an insecticide (C) such as (C1), (C2), (C3), (C4) and (C5) mentioned above, optionally with another herbicide (B) according to the following scheme:
(A)+(B1)+(C), (A)+(B2)+(C), (A)+(B29.4)+(C), (A)+(B29.4)+(C), (A)+(B3.1)+(C), (A)+(B3.2)+(C), (A)+(B4)+(C), (A)+(B29.4)+(C), (A)+(B29.4)+(C), (A)+(B5.1)+(C), (A)+(B5.2)+(C), (A)+(B5.3)+(C), (A)+(B29.4)+(C), (A)+(B29.4)+(C),
(A)+(B8)+(C), (A)+(B29.4)+(C), (A)+(B8.2)+(C), (A)+(B9)+(C), (A)+(B29.4)+(C), (A)+(B29.4)+(C), (A)+(B29.4)+(C), (A)+(B29.4)+(C), (A)+(B10.1)+(C), (A)+(B29.4)+(C), (A)+(B11.1)+(C), (A)+(B29.4)+(C), (A)+(B11.3)+(C), (A)+(B29.4)+(C), (A)+(B12.1)+(C), (A)+(B29.4)+(C), (A)+(B29.4)+(C), (A)+(B29.4)+(C), (A)+(B13.1)+(C), (A)+(B13.2)+(C), (A)+(B13.3)+(C), (A)+(B13.4)+(C), (A)+(B13.5)+(C), (A)+(B29.4)+(C), (A)+(B14)+(C), (A)+(B14.1)+(C), (A)+(B14.2)+(C), (A)+(B29.4)+(C), (A)+(B15)+(C), (A)+(B15.1)+(C), (A)+(B29.4)+(C), (A)+(B29.4)+(C), (A)+(B17)+(C), (A)+(B29.4)+(C), (A)+(B18)+(C), (A)+(B29.4)+(C), (A)+(B29.4)+(C), (A)+(B29.4)+(C), (A)+(B19.1)+(C), (A)+(B19.2)+(C), (A)+(B19.3)+(C), (A)+(B19.4)+(C), (A)+(B19.5)+(C), (A)+(B19.6)+(C), (A)+(B19.7)+(C), (A)+(B20)+(C), (A)+(B29.4)+(C), (A)+(B21)+(C), (A)+(B29.4)+(C), (A)+(B22)+(C), (A)+(B29.4)+(C), (A)+(B23)+(C), (A)+(B29.4)+(C), (A)+(B24)+(C), (A)+(B29.4)+(C); (A)+(B29.4)+(C), (A)+(B26)+(C), (A)+(B29.4)+(C), (A)+(B27)+(C), (A)+(B29.4)+(C), (A)+(B28)+(C), (A)+(B29.4)+(C), (A)+(B29.4)+(C), (A)+(B29.4)+(C), (A)+(B29.4)+(C), (A)+(B29.4)+(C), (A)+(B30)+(C), (A)+(B30.1)+(C), (A)+(B30.2)+(C), (A)+(B30.3)+(C), (A)+(B31)+(C), (A)+(B31.1)+(C), (A)+(B31.2)+(C), (A)+(B31.3)+(C), (A)+(B32)+(C), (A)+(B32.1)+(C), (A)+(B32.2)+(C), (A)+(B33)+(C), (A)+(B34)+(C), (A)+(B34.1)+(C), (A)+(B34.2)+(C), (A)+(B35)+(C), (A)+(B36)+(C), (A)+(B36.1)+(C), (A)+(B36.2)+(C), (A)+(B37)+(C), (A)+(B37.1)+(C), (A)+(B37.2)+(C), (A)+(B38)+(C), (A)+(B38.1)+(C), (A)+(B38.2)+(C), (A)+(B39)+(C), (A)+(B39.1)+(C), (A)+(B40)+(C), (A)+(B40.1)+(C), (A)+(B41)+(C), (A)+(B41.1)+(C), (A)+(B41.2)+(C), (A)+(B42)+(C), (A)+(B42.1)+(C), (A)+(B42.2)+(C), (A)+(B42.3)+(C), (A)+(B43)+(C), (A)+(B43.1)+(C) or (A)+(B44.1)+(C).

The above combinations preferably comprise imidacloprid or thiamethoxam as components (C).

The above combinations also optionally additionally, or preferably comprise safeners as components (C). Safeners are mentioned in the context of herbicidal combination partners already. Examples for safeners are:
Benoxacor, Cloquintocet(-mexyl), Cyometrinil, Cyprosulfamide, Dichlormid, Fenchlorazole(-ethyl), Fenclorim, Flurazole, Fluxofenim, Furilazole, Isoxadifen(-ethyl), Mefenpyr(-diethyl), Naphthalic anhydride, Oxabetrinil, "AD-67" oder "MON 4660" (=3-Dichloracetyl-1-oxa-3-aza-spiro[4,5]decan), "TI-35" (=1-Dichloracetyl-azepan),
"Dimepiperate" oder "MY-93" (=Piperidin-1-thiocarbonsäure-S-1-methyl-1-phenylethylester), "Daimuron" oder "SK 23" (=1-(1-Methyl-1-phenylethyl)-3-p-tolyl-harnstoff), "Cumyluron"="JC-940" (=3-(2-Chlorphenylmethyl)-1-(1-methyl-1-phenyl-ethyl)harnstoff),
preferably Benoxacor, Cloquintocet(-mexyl), Cyprosulfamide, Isoxadifen(-ethyl) or Mefenpyr(-diethyl).

The compounds of formula (I) or combinations with other active ingredients (A) and/or (C) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hanser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hanser Verlag, Munich, 4th Ed. 1986.

Based on these formulations, it is also possible to prepare combinations with other pesticidally active substances (C) such as, for example, insecticides, acaricides, herbicides, fungicides, and with safeners, fertilizers and/or growth regulators, for example in the form of a readymix or a tank mix.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of compounds of formula (I).

The concentration of compounds of formula (I) in wettable powders is, for example, approximately 10 to 90% by weight, the remainder to 100% by weight being composed of customary formulation components. In the case of emulsifiable concentrates, the concentration of compounds of formula (I) can amount to approximately 1 to 90, preferably 5 to 80% by weight. Formulations in the form of dusts usually comprise 1 to 30% by weight of compounds of formula (I), preferably in most cases 5 to 20% by weight of compounds of formula (I), while sprayable solutions comprise approximately 0.05 to 80, preferably 2 to 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise between 1 and 95% by weight of active substance, preferably between 10 and 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or growth regulators, for example as a premix or as tank mixes.

The invention is further described by the following non-limiting examples which further illustrate the invention, and are not intended, nor should they be interpreted, to, limit the scope of the invention.

FORMULATION EXAMPLES a) A dust is obtained by mixing 10 parts by weight of a compound of formula (I) and 90 parts by weight of talc as inert material and grinding the mixture in a hammer mill.

b) A wettable powder which is readily dispersible in water is obtained by mixing 25 parts by weight of a compound of formula (I), 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of formula (I), 75 parts by weight of cyclohexanone as solvent and 10 parts by weight of oxethylated nonylphenol as emulsifier.

e) Water-dispersible granules are obtained by mixing
75 parts by weight of a compound of formula (I),
10 parts by weight of calcium ligno-sulfonate,
5 parts by weight of sodium laurylsulfate,
3 parts by weight of polyvinyl alcohol and
7 parts by weight of kaolin,
grinding the mixture in a pinned disk mill and granulating the powder in a fluidized bed by spraying on water as granulation liquid.

f) Alternatively, water-dispersible granules are obtained by homogenizing and precomminuting, on a colloid mill,
25 parts by weight of a compound of formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture on a bead mill and atomizing and drying the resulting suspension in a spray tower by means of a single-substance nozzle.

Biological Examples

1. Selectivity Testing 1.1 General Application and Evaluation Conditions:

A formulation of the a compound of formula (I) of the invention was diluted with water and applied with a water volume between 100 liter to 1000 liter/ha for spray applications and up to 10000 liter for drench applications at an application rate between 25 to 200 g active ingredients per hectare (=a.i./ha).

Alternatively, granular formulations were scattered evenly on the test plots and watered 1 or 2 days.

In other tests a co-formulation of compounds of formula (I) of the invention (compound (A)) and another herbicidal active ingredient (compound (B)) was diluted with water in the same manner described above and applied at the combined application rate, i.e. 25-200 g a.i./ha for herbicide (A) and an amount of herbicide (B) that is effective for weed control.

Alternative applications were based on a tank-mix of a diluted formulation of a compound of formula (I) (compound (A)) and a diluted formulation of another herbicidal active ingredient (compound (B)) at application rates mentioned above.

The application was performed between fall, winter, spring and early summer and conducted on established turf, either on dormant turf or on actively growing turf grass.

Selectivity ratings were based on turf quality ratings as a 1-9 scale (1=turf dead, 9=no damage, 7-9 is an acceptable selectivity if compared to untreated turf rated 9) or as % damage compared to parallel untreated controls. Evaluation timing was done from 1 week after application to 3-6 months after application.

1.2 Specific Examples (Selectivity in Turf Grass)

Formulations of the compound of formula (I) in form of water-soluble powders (WP) or suspensions (SC) were applied with a water volume of 600 liter/ha and sprayed with a spraying device (knapsack sprayer) at an application rate of up to 100 g a.i./ha. to various turfgrass varieties in spring. The evaluation was made over a period of 1 week to 6 months after application. The compounds of the formula (I) according to the invention as represented by compounds from Table 1 above (compounds A1 to A127) showed a good selectivity in turf and can be used for weed control in turf without substantial injury to turf.

From a series of tests with turfgrass varieties *Cynodon* spp., *Zoysia* spp., *Paspalum* spp., *Poa pratensis* and *Festuca arundinacea* high average selectivity ratings are found with the compounds (A5), (A9)-(A13), (A19)-(A22), (A28)-(A30), (A41) to (A43), (A45), (A46), (A70), (A79), (A85), (A86), (A99) to (A102), (A122) to (A126) (see Table 2 below):

TABLE 2

| | Selectivity Rating | |
|---|---|---|
| Turfgrasses | 1 week after application | 6 month after application |
| untreated | 9 | 9 |
| *Cynodon* spp.: | 8-9 | 8-9 |
| *Zoysia* spp.: | 8-9 | 8-9 |
| *Paspalum* spp. | 8-9 | 8-9 |
| *Poa pratensis* | 7-8 | 7-8 |
| *Festuca arundinacea* | 7-8 | 7-8 |

1.3 Specific Example (Selectivity Testing in Turf Grass Species), Sprayable Formulation A formulation (water-dispersable powder) containing a mixture of the compounds no. (A21) and (A22) of Table 1 above wherein compound (A21) is the main component (active ingredient mixture having common name indaziflam) was applied with a water volume of aprox 400 liter/ha with a spraying device (knapsack sprayer) on the turf grass species indicated below at the application rate given in Table 3 below.
Turf grass species: *Cynodon dactylon*, variety 'Tifway 419' (Bermuda grass)
Location: Golf course in Florida, USA
Application timing: 1 May 2006 on actively growing turf, late spring conditions
Soil type: sand
Plot size: 1.6 m$^2$ and 3 replicates per treatment Turf maintenance was done according to local practice in respect to mowing intervals, watering and fertilization. The evaluation was made over a period of 100 days after application (=DAT=days after treatment). Turf grass quality was rated according to a scale from 1 to 9 wherein 9 means high quality and 1 means turf grass died. Lower turf grass quality for untreated turf may be caused by bad soil or weather conditions such as low or high temperatures, drought or insufficient fertilizing. Selectivity evaluation is based on the comparison of the ratings for untreated versus treated turf. Compared to untreated high quality turf (rate 9) a rating of 9 for the treated turf indicates high selectivity of the test compound(s) (=no phytotoxicity of the turf grass) while rating of 1 means no selectivity (=turf grass completely damaged). All ratings of 9 to 7 for treated turf grass are commercially acceptable. The results are summarized in Table 3.

TABLE 3

| Cpd. No. | Application rate | Selectivity evaluation | | | | | |
|---|---|---|---|---|---|---|---|
| | | 7 DAT | 21 DAT | 35 DAT | 49 DAT | 77 DAT | 100 DAT |
| untreated | — | 9 | 9 | 9 | 9 | 9 | 9 |
| (A21)/(A22) | 50 g a.i./ha | 9 | 8 | 8 | 9 | 9 | 9 |

1.4 Specific Example (Selectivity Testing in Turf Grass Species), Sprayable Formulation An application and evaluation were done as described in example 1.3 with the difference:
Turf grass species: *Cynodon dactylon*, variety 'Tifway 419' (Bermuda grass)
Location: Sports turf in North Carolina, USA
Application timing: 16 Mar. 2006 during dormancy of the turf
Plot size: 8 m² and 3 replicates per treatment
Evaluation timing: over a period of 159 days after application (DAT).
The results are summarized in Table 4.

TABLE 4

| Cpd. No. | Application rate [g a.i./ha] | Selectivity evaluation | | | | | |
|---|---|---|---|---|---|---|---|
| | | 35 DAT | 48 DAT | 70 DAT | 92 DAT | 120 DAT | 159 DAT |
| untreated | — | 8 | 8 | 8 | 9 | 9 | 8 |
| (A21)/(A22) | 50 | 8 | 8 | 8 | 9 | 9 | 8 |
| (A21)/(A22) | 100 | 8 | 8 | 8 | 9 | 9 | 8 |
| (A21)/(A22) | 150 | 8 | 8 | 8 | 9 | 9 | 8 |

1.5 Specific Example (Selectivity Testing in Turf Grass Species), Sprayable Formulation An application and evaluation were done as described in example 1.4 with the difference that the turf grass species was *Zoysia japonica*, variety 'Emerald' (*Zoysia* grass)
The results are summarized in Table 5.

TABLE 5

| Cpd. No. | Application rate [g a.i./ha] | Selectivity evaluation | | | | | |
|---|---|---|---|---|---|---|---|
| | | 35 DAT | 48 DAT | 70 DAT | 92 DAT | 120 DAT | 159 DAT |
| untreated | — | 7 | 8 | 9 | 9 | 8.7 | 9 |
| (A21)/(A22) | 50 | 7 | 8 | 8.7 | 8.7 | 8.3 | 9 |
| (A21)/(A22) | 100 | 7 | 8 | 8 | 8 | 8 | 9 |
| (A21)/(A22) | 150 | 7 | 8 | 8.7 | 9 | 8.7 | 9 |

1.6 Specific Example (Selectivity Testing in Turf Grass Species), Sprayable Formulation An application and evaluation were done as described in example 1.4 with the difference that the turf grass species was *Stenotaphyrum secundatum*, variety (St. Augustine grass). The results are summarized in Table 6.

TABLE 6

| Cpd. No. | Application rate [g a.i./ha] | Selectivity evaluation | | | | | |
|---|---|---|---|---|---|---|---|
| | | 35 DAT | 48 DAT | 70 DAT | 92 DAT | 120 DAT | 159 DAT |
| untreated | — | 8 | 8 | 8 | 9 | 9 | 9 |
| (A21)/(A22) | 50 | 8 | 8 | 8 | 9 | 9 | 9 |
| (A21)/(A22) | 100 | 8 | 8 | 8 | 9 | 9 | 9 |
| (A21)/(A22) | 150 | 8 | 8 | 8 | 9 | 9 | 9 |

1.7 Specific Example (Selectivity Testing in Turf Grass Species), Sprayable Formulation An application and evaluation were done as described in example 1.4 with the difference that the turf grass species was *Eremochloa ophiuroides*, variety (centipede grass). The results are summarized in Table 7.

TABLE 7

| Cpd. No. | Application rate [g a.i./ha] | Selectivity evaluation | | | | | |
|---|---|---|---|---|---|---|---|
| | | 35 DAT | 48 DAT | 70 DAT | 92 DAT | 120 DAT | 159 DAT |
| untreated | — | 8 | 9 | 8.7 | 9 | 9 | 9 |
| (A21)/(A22) | 50 | 8 | 9 | 8.7 | 9 | 9 | 9 |
| (A21)/(A22) | 100 | 8 | 9 | 8.7 | 9 | 9 | 9 |
| (A21)/(A22) | 150 | 8 | 9 | 9 | 9 | 9 | 9 |

1.8 Specific Example (Selectivity Testing in Turf Grass Species), Sprayable Formulation An application and evaluation were done as described in example 1.4 with the difference that the turf grass species was *Paspalum notatum*, variety (bahia grass). The results are summarized in Table 8.

TABLE 8

| Cpd. No. | Application rate [g a.i./ha] | Selectivity evaluation | | | | | |
|---|---|---|---|---|---|---|---|
| | | 35 DAT | 48 DAT | 70 DAT | 92 DAT | 120 DAT | 159 DAT |
| untreated | — | 7 | 8 | 9 | 9 | 9 | 9 |
| (A21)/(A22) | 50 | 7 | 8 | 9 | 9 | 9 | 9 |
| (A21)/(A22) | 100 | 7 | 8 | 9 | 9 | 9 | 9 |
| (A21)/(A22) | 150 | 7 | 8 | 9 | 9 | 9 | 9 |

1.9 Specific Example (Selectivity Testing in Turf Grass Species), Sprayable Formulation An application and evaluation were done as described in example 1.4 with the following difference:
Turf grass species: *Festuca arundinacea*, variety 'Midnight' (fescue grass)
Application timing: 11 Aug. 2005, applied on actively growing turf in summer
Plot size: 4 m² and 3 replicates per treatment
Evaluation timing: over a period of 96 days after application (DAT).
The results are summarized in Table 9.

TABLE 9

| Cpd. No. | Application rate [g a.i./ha] | Selectivity evaluation | | | | | | | | | |
|---|---|---|---|---|---|---|---|---|---|---|---|
| | | 7 DAT | 14 DAT | 21 DAT | 27 DAT | 33 DAT | 40 DAT | 49 DAT | 62 DAT | 81 DAT | 96 DAT |
| untreated | — | 9 | 9 | 9 | 9 | 9 | 9 | 9 | 9 | 9 | 9 |
| (A21)/(A22) | 25 | 9 | 9 | 9 | 9 | 9 | 9 | 9 | 9 | 9 | 8.7 |
| (A21)/(A22) | 50 | 9 | 9 | 9 | 8.7 | 8.7 | 8.3 | 8.7 | 8.3 | 8 | 7.7 |
| (A21)/(A22) | 100 | 9 | 9 | 8.3 | 7.7 | 7.7 | 7.7 | 7.7 | 7.3 | 6.3 | 6.3 |

1.10 Specific Example (Selectivity Testing in Turf Grass Species)

An application and evaluation were done as described in example 1.4 with the following difference:
Turf grass species: *Cynodon dactylon*, variety 'Tifsport' (hybrid Bermuda grass)
Application timing: 19 Apr. 2006, applied during early green-up of the turf
Plot size: 8 m² and 3 replicates per treatment
Evaluation timing: over a period of 125 days after application (DAT).
The results are summarized in Table 10.

TABLE 10

| Cpd. No. | Application rate [g a.i./ha] | Selectivity evaluation | | | | |
|---|---|---|---|---|---|---|
| | | 14 DAT | 37 DAT | 61 DAT | 90 DAT | 125 DAT |
| untreated | — | 8 | 8 | 9 | 9 | 8 |
| (A21)/(A22) | 50 | 8 | 8 | 9 | 9 | 8 |
| (A21)/(A22) | 100 | 8 | 8 | 9 | 9 | 8 |
| (A21)/(A22) | 150 | 8 | 8 | 9 | 9 | 8 |

1.11 Specific Example (Selectivity Testing in Turf Grass Species), Sprayable Formulation An application and evaluation were done as described in example 1.4 with the following difference:
Turf grass species: *Zoysia japonica*, variety 'Emerald' (*Zoysia* grass)
Application timing: 20 Apr. 2006, applied during early green-up of the turf
Evaluation timing: over a period of 124 days after application (DAT).
The results are summarized in Table 11.

TABLE 11

| Cpd. No. | Application rate [g a.i./ha] | Selectivity evaluation | | | | |
|---|---|---|---|---|---|---|
| | | 12 DAT | 36 DAT | 60 DAT | 89 DAT | 124 DAT |
| untreated | — | 8 | 8 | 9 | 9 | 9 |
| (A21)/(A22) | 50 | 8 | 8 | 9 | 9 | 9 |
| (A21)/(A22) | 100 | 8 | 8 | 9 | 9 | 9 |
| (A21)/(A22) | 150 | 8 | 8 | 9 | 9 | 9 |

1.12 Specific Example (Selectivity Testing in Turf Grass Species), Sprayable Formulation An application and evaluation were done as described in example 1.4 with the following difference:
Turf grass species: *Stenotaphrum, secundatum*, variety (St. Augustine grass)
Application timing: 19 Apr. 2006, applied during early green-up of the turf
Evaluation timing: over a period of 125 days after application (DAT).
The results are summarized in Table 12.

TABLE 12

| Cpd. No. | Application rate [g a.i./ha] | Selectivity evaluation | | | | |
|---|---|---|---|---|---|---|
| | | 14 DAT | 37 DAT | 61 DAT | 90 DAT | 125 DAT |
| untreated | — | 8 | 9 | 9 | 9 | 9 |
| (A21)/(A22) | 50 | 8 | 9 | 9 | 9 | 9 |
| (A21)/(A22) | 100 | 8 | 9 | 9 | 9 | 9 |
| (A21)/(A22) | 150 | 8 | 9 | 9 | 9 | 9 |

1.13 Specific Example (Selectivity Testing in Turf Grass Species), Sprayable Formulation An application and evaluation were done as described in example 1.4 with the following difference:
Turf grass species: *Eremochloa ophiuroides*, variety (Centipede grass)
Application timing: 19 Apr. 2006, applied during early green-up of the turf
Evaluation timing: over a period of 125 days after application (DAT).
The results are summarized in Table 13.

TABLE 13

| Cpd. No. | Application rate [g a.i./ha] | Selectivity evaluation | | | | |
|---|---|---|---|---|---|---|
| | | 14 DAT | 37 DAT | 61 DAT | 90 DAT | 125 DAT |
| untreated | — | 9 | 9 | 9 | 9 | 9 |
| (A21)/(A22) | 50 | 8 | 8.7 | 9 | 9 | 9 |
| (A21)/(A22) | 100 | 9 | 9 | 9 | 9 | 9 |
| (A21)/(A22) | 150 | 9 | 8.7 | 9 | 9 | 9 |

1.14 Specific Example (Selectivity Testing in Turf Grass Species), Sprayable Formulation An application and evaluation were done as described in example 1.4 with the following difference:
Turf grass species: *Paspalum notatum*, variety (Bahia grass)
Application timing: 19 Apr. 2006, applied during early green-up of the turf
Evaluation timing: over a period of 125 days after application (DAT).
The results are summarized in Table 14.

TABLE 14

| Cpd. No. | Application rate [g a.i./ha] | Selectivity evaluation | | | | |
|---|---|---|---|---|---|---|
| | | 14 DAT | 37 DAT | 61 DAT | 90 DAT | 125 DAT |
| untreated | — | 8 | 9 | 9 | 9 | 9 |
| (A21)/(A22) | 50 | 8 | 9 | 9 | 9 | 9 |

TABLE 14-continued

| Cpd. No. | Application rate [g a.i./ha] | Selectivity evaluation | | | | |
|---|---|---|---|---|---|---|
| | | 14 DAT | 37 DAT | 61 DAT | 90 DAT | 125 DAT |
| (A21)/(A22) | 100 | 9 | 9 | 9 | 9 | 9 |
| (A21)/(A22) | 150 | 9 | 9 | 9 | 9 | 9 |

1.15 Specific Example (Selectivity Testing in Turf Grass Species), Sprayable Formulation A formulation (water-dispersable powder) containing a mixture of compounds no. (A21) and (A22) according to Table 1 above, in which compound (A21) is the main component (active ingredient mixture having common name indaziflam), was applied with a water volume of aprox 400 liter/ha with a spraying device (knapsack sprayer) on the turf grass species indicated below at the application rate given in Table 15 below. Turf maintenance was done according to local practice in respect to mowing intervals, watering and fertilization.

Turf grass species: *Festuca arundinacea*, variety 'Tomahawk' (fescue grass)
Location: Sports turf in North Carolina, USA
Plot size: 1 m² and 4 replicates per treatment
Application timing: 12 Mar. 2007, spring application on green turf The evaluation was made over a period of 402 days after application.

Turf grass quality was rated according to a scale from 1 to 9 wherein 9 means high quality and 1 means turf grass died. Lower turf grass quality for untreated turf may be caused by bad soil or weather conditions such as low or high temperatures, drought or insufficient fertilizing. Selectivity evaluation is based on the comparison of the ratings for untreated versus treated turf. Compared to untreated high quality turf (rate 9) a rating of 9 for the treated turf indicates high selectivity of the test compound(s) (=no phytotoxicity of the turf grass) while rating of 1 means no selectivity (=turf grass completely damaged). All ratings of 9 to 7 for treated turf grass are commercially acceptable.

The results are summarized in Table 15.

TABLE 15

| Cpd. No. | Application rate [g a.i./ha] | Selectivity evaluation | | | | |
|---|---|---|---|---|---|---|
| | | 30 DAT | 64 DAT | 101 DAT | 123 DAT | 402 DAT |
| untreated | — | 6.8 | 7.3 | 8.3 | 8.4 | 8.0 |
| (A21)/(A22) | 20 | 7.3 | 7.5 | 8.8 | 8.9 | 8.3 |
| (A21)/(A22) | 30 | 6.5 | 7.0 | 8.3 | 8.1 | 8.3 |
| (A21)/(A22) | 60 | 7.0 | 7.5 | 8.8 | 8.5 | 8.3 |

1.16 Specific Example (Selectivity Testing in Turf Grass Species), Granular Application An application and evaluation was done as described in example 1.15 with the following difference:

Three granular formulations (GR) with different content of (A) (granules having 0.0071% a.i., 0.011% a.i. and 0.021% a.i.) of said mixture of compounds (A21) and (A22) were separately scattered by hand evenly on similar test plots. The treatments were watered in 1 and 2 days after application with a volume equivalent to 3.6 cm and 3.8 cm rainfall, respectively. The results are summarized in Table 16.

TABLE 16

| Cpd. No. | Application rate [g a.i./ha] | Selectivity evaluation | | | | |
|---|---|---|---|---|---|---|
| | | 30 DAT | 64 DAT | 101 DAT | 123 DAT | 402 DAT |
| untreated | — | 6.8 | 7.3 | 8.3 | 8.4 | 8.0 |
| (A21)/(A22), GR 0.0071% | 20 | 7.8 | 8.0 | 9.0 | 8.9 | 8.5 |
| (A21)/(A22) GR 0.011% | 30 | 7.3 | 7.0 | 8.0 | 8.3 | 8.0 |
| (A21)/(A22) GR 0.021% | 60 | 7.3 | 7.5 | 8.3 | 8.5 | 8.1 |

1.17 Specific Example (Selectivity Testing in Turf Grass Species), Sprayable Formulation A formulation (water-dispersable powder) containing a mixture of compounds no. (A21) and (A22) according to Table 1 above, in which compound (A21) is the main component (active ingredient mixture having common name indaziflam), was applied with a water volume of aprox 400 liter/ha with a spraying device (knapsack sprayer) on the turf grass species indicated below at the application rate given in Table 17 below. Turf maintenance was done according to local practice in respect to mowing intervals, watering and fertilization.

Turf grass species: *Festuca arundinacea*, variety 'Wolfspack' (fescue grass)
Location: Sports turf in North Carolina, USA
Plot size: 3 m² and 3 replicates per treatment
Application timing: 16 Aug. 2005, summer application on green turf The evaluation was made over a period of 91 days after application. Selectivity evaluated as described in Example 1.16.

The results are summarized in Table 17.

TABLE 17

| Cpd. No. | Application rate [g a.i./ha] | Selectivity evaluation | | | | |
|---|---|---|---|---|---|---|
| | | 7 DAT | 14 DAT | 28 DAT | 57 DAT | 91 DAT |
| untreated | — | 9 | 9 | 9 | 9 | 9 |
| (A21)/(A22) | 25 | 9 | 9 | 9 | 9 | 9 |
| (A21)/(A22) | 50 | 9 | 9 | 9 | 8.7 | 8.3 |

1.18 Specific Example (Selectivity Testing in Turf Grass Species), Granular Application An application and evaluation was done as described in example 1.17 with the following difference:

Three granular formulations with different content of (A) (GR 0.015%, GR 0.021% and GR 0.03%, "%" means content of a.i.) of said mixture of compounds (A21) and (A22) were separately scattered by hand evenly on similar test plots. The treatments were watered in 1 and 2 days after application with a volume equivalent to 3.6 cm and 3.8 cm rainfall, respectively.

The results are summarized in Table 18.

TABLE 18

| Cpd. No. | Application rate [g a.i./ha] | Selectivity evaluation | | | | |
|---|---|---|---|---|---|---|
| | | 7 DAT | 14 DAT | 28 DAT | 57 DAT | 91 DAT |
| untreated | — | 9 | 9 | 9 | 9 | 9 |
| (A21)/(A22), GR 0.015% | 25 | 9 | 9 | 8.3 | 8.7 | 8.7 |

TABLE 18-continued

| Cpd. No. | Application rate [g a.i./ha] | Selectivity evaluation | | | | |
|---|---|---|---|---|---|---|
| | | 7 DAT | 14 DAT | 28 DAT | 57 DAT | 91 DAT |
| (A21)/(A22) GR 0.03% | 50 | 9 | 8.3 | 7.3 | 7.3 | 7.3 |
| (A21)/(A22) GR 0.021% | 60 | 9 | 9 | 9 | 9 | 9 |

1.19 Specific Example (Selectivity Testing in Turf Grass Species), Co-Formulation A co-formulation containing a mixture of compounds nos. (A21) and (A22) according to Table 1 above, in which compound (A21) is the main component (active ingredient mixture having common name indaziflam) and the other herbicides indicated in Table 19, was applied with a water volume of aprox 600 liter/ha with a spraying device (knapsack sprayer) on the turf grass species indicated below at the application rate given in Table 19 below. Alternatively, granules were evenly applied with a shaker can.

Turf maintenance was done according to local practice in respect to mowing intervals, watering and fertilization.

Turf grass species: *Lolium perenne*, variety (perennial ryegrass)
Location: Sports turf, New Jersey, USA
Plot size: 3 m² and 4 replicates per treatment
Application timing: 8 May, spring application on growing turf The evaluation was made over a period of 2.5 months after application. Selectivity (phytotoxicity) was rated in percent (%) injury compared with untreated control turf. The results are summarized in Table 19.

2. Post-Emergence Efficacy Testing Example for Dicot Weed Control 2.1 General Application and Evaluation Conditions:

The formulation of compound of formula (I), optionally together with other herbicides (B) was applied as set forth in section 1.1 above.

Application was conducted on established turf infested with the weed plants, while the turf was dormant turf or actively growing turf.

The application timing comprises fall, winter, spring and early summer when young weeds are in the 1-3 leaf stage.

Efficacy rating was regularly based on % damage of the leaf area on the weeds up to the first 3 weeks after testing. In special cases efficacy ratings were also done from 1 week after treatment up to 3 to 6 month after treatment.

As latest after that timing lawn and turf areas were mowed. This allowed better control of the coverage on the treated area with vital and actively growing weeds relative to the untreated area.

0% means no efficacy and 100% mean full control of the weed.

2.2 Specific Example

Formulations of the compound of formula (I) formulations in form of water-soluble powders (WP) or suspensions (SC) were applied with a water volume of 600 liter/ha and sprayed with a spraying device (knapsack sprayer) at an application rate of up to 50 g a.i./ha. to turfgrass infested with weeds in spring. The evaluation was made over a period of 3 weeks after application. The compounds of the formula (I) according to the invention as represented by compounds from Table 1 above (compounds A1 to A127) showed a good selectivity in turf and weed control. From a series of tests with weeds

TABLE 19

| Cpd. No. | Application rate [g a.i./ha] | Selectivity evaluation (% injury) | | | | | | |
|---|---|---|---|---|---|---|---|---|
| | | 5 DAT | 11 DAT | 19 DAT | 25 DAT | 39 DAT | 53 DAT | 67 DAT |
| untreated | — | 0 | 0 | 0 | 0 | 0 | 0 | 0 |
| (A21)/(A22) + Dicamba + Triclopyr + MCPA | 13.44 + 156 + 112 + 1568 | 0 | 0 | 0 | 0 | 0 | 0 | 0 |
| (A21)/(A22) + Dicamba + Triclopyr + MCPA | 21.52 + 156 + 112 + 1568 | 0 | 0 | 0 | 0 | 0 | 0 | 0 |
| (A21)/(A22) + Dicamba + Triclopyr + MCPA | 26.83 + 156 + 112 + 1568 | 0 | 0 | 0 | 0 | 0 | 0 | 0 |
| (A21)/(A22) + Dicamba + 2,4-D + Mecoprop-P on 30-0-2 Fertilizer granule | 24.32 + 91 + 825 + 199.4 | 0 | 0 | 0 | 0 | 0 | 0 | 0 |
| (A21)/(A22) + Dicamba + 2,4-D + Mecoprop-P on 20-0-3 Fertilizer granule | 24.82 + 85.8 + 1970 + 470 | 0 | 0 | 0 | 0 | 0 | 0 | 0 |

Abbreviations in Table 19:
"30-0-3 Fertilizer granule" means granules of a fertilizer containing 30% b. w. nitrogen, 0% by weight (b. w.) phosphorus and 3% b. w. potassium,
"20-0-2 Fertilizer granule" means granules of a fertilizer containing 20% b. w. nitrogen, 0% b. w. phosphorus and 2% b. w. potassium, often occurring in lawn good average weed control was found with the compounds (A5), (A9)-(A13), (A19)-(A22), (A28)-(A30), (A41) to (A43), (A45), (A46), (A70), (A79), (A85), (A86), (A99) to (A102), (A122) to (A126) (see table below):

| Weeds | Efficacy rating |
|---|---|
| Lamium purpureum | 70%-80% |
| Trifolium repens | 70%-80% |
| Veronica spp. | 70%-80% |
| Plantago lanceolata | 70%-80% |

3. Pre-Emergence Efficacy Testing Example for Dicot Weed Control 3.1 General Application and Evaluation Conditions:

The formulation of compound of formula (I), optionally together with other herbicides (B) was applied as set forth in section 1.1 above.

Application was conducted on established turf infested with the weed plants, while the turf was dormant turf or actively growing turf.

The application timing comprises fall, winter, spring and early summer prior to emergence of the young weeds.

Efficacy rating was based on % coverage on the treated area relative to the untreated area. 0% means no efficacy and 100% mean full control of the weed. Efficacy rating was done after the emergence of the weed when reaching the 2-3 leaf stage or later.

3.2 Specific Example

Formulations of the compound of formula (I) formulations in form of water-soluble powders (WP) or suspensions (SC) were applied to with a water volume of 600 liter/ha and sprayed with a spraying device (knapsack sprayer) at an application rate of up to 50 g a.i./ha. to turfgrass infested with weeds in spring prior to emergence of the weed plants. The evaluation was made in the 2-3 leave stage of the weed plants as shown in the control experiment. The compounds of the formula (I) according to the invention as represented by compounds from Table 1 above (compounds A1 to A127) showed a good selectivity in turf and weed control. From a series of tests with weeds often occurring in lawn good average weed control was found with the compounds (A5), (A9)-(A13), (A19)-(A22), (A28)-(A30), (A41) to (A43), (A45), (A46), (A70), (A79), (A85), (A86), (A99) to (A102), (A122) to (A126) (see table below):

| Weeds | Efficacy rating |
|---|---|
| Trifolium repens | 80%-90% |
| Veronica spp. | 80%-90% |
| Plantago lanceolata | 80%-90% |

4. Pre-Emergence Efficacy Testing Example for Grass Weed Control 4.1 General Application and Evaluation Conditions:

The formulation of compound of formula (I), optionally together with other herbicides (B) was applied as set forth in section 1.1 above.

Application was conducted on established turf infested with the weed plants, while the turf was dormant turf or actively growing turf.

The application timing comprises fall, winter, spring and early summer prior to emergence of the young weeds.

Efficacy rating was based on % coverage on the treated area relative to the untreated area. 0% means no efficacy and 100% mean full control of the weed. Efficacy rating was done after the emergence of the weed when reaching the 2-3 leaf stage or later.

4.2 Specific Example

Formulations of the compound of formula (I) formulations in form of water-soluble powders (WP) or suspensions (SC) were applied with a water volume of 600 liter/ha and sprayed with a spraying device (knapsack sprayer) at an application rate of up to 50 g a.i./ha. to turfgrass infested with weeds in spring prior to emergence of the weed plants. The evaluation was made in the 2-3 leave stage of the weed plants as shown in the control experiment. The compounds of the formula (I) according to the invention as represented by compounds from Table 1 above (compounds A1 to A127) showed a good selectivity in turf and weed control. From a series of tests with weeds often occurring in lawn excellent average weed control was found with the compounds (A5), (A9)-(A13), (A19)-(A22), (A28)-(A30), (A41) to (A43), (A45), (A46), (A70), (A79), (A85), (A86), (A99) to (A102), (A122) to (A126) (see table below):

| Weeds | Efficacy rating |
|---|---|
| Digitaria sanguinea | 90%-100% |
| Elusine indica | 90%-100% |
| Poa annua | 90%-100% |

5. Examples for Selectivity and Weed Control Pre- and Post-Emergence to Weeds 5.1 Specific Example (Effectivity Testing Against Weed Plants), Sprayable Formulation A formulation (water-dispersable powder) containing a mixture of compounds no. (A21) and (A22) according to Table 1 above, in which compound (A21) is the main component (active ingredient mixture having common name indaziflam) was applied with a water volume of aprox 400 liter/ha with a spraying device (knapsack sprayer) on the turf grass species indicated below at the application rate given in Table 20 below. Each plot was divided by different pre-treatments 1 week before application of the trial treatments:

A) Pre-treatment with glyphosate-isopropylammonium allowing to evaluate in this section the pre-emergence effect against weeds.

B) No pre-treatment, present winter annual weeds are received a post-emergence application.

Turf maintenance was done according to local practice in respect to mowing intervals, watering and fertilization.

Turf grass species: *Cynodon dactylon*, variety (Bermuda grass)

Weed species: *Poa annua, Veronica arvensis, Digitaria sanguinales, Aphanes arvensis, Lamium amplexicaule, Stellaria media*

Location: Fairway on golf course, Virginia, USA (Tables 20-23) and sports turf, North Carolina, USA (Tables 24-26)

Plot size: 12 m² and 3 replicates per treatment

Application timing: 1 Dec. 2005, applied on dormant turf in winter

The evaluation was made over a period of indicated in the tables. Effectivity was rated in percent (%) herbicidal effect compared with untreated control according to the method of Abbott according to the formula [(X−Y)/X]100 where X is the absolute level/scoring of the control plants, Y is the level/scoring of the treated plants. 100% efficacy means full control; 0% efficacy means no control of the weed; all ratings above 80% are usually acceptable.

Additionally, phytotoxicity of the turf was rated as percent (%) injury compared with untreated control.

The results are summarized in Tables 20, 21, 22, 23, 24, 25 and 26 below.

TABLE 20

| Cpd. No. | Application rate [g a.i./ha] | Herbicidal effect (%) on *Poa annua* Pre-emergence application after pre-treatment | | | Phytotoxicity (%) on Turf |
|---|---|---|---|---|---|
| | | 123 DAT | 157 DAT | 187 DAT | 157 DAT |
| untreated (% coverage) | — | 0 (87) | 0 (73) | 0 (47) | 0 |
| (A21)/(A22) | 25 | 96 | 92 | 96 | 0 |
| (A21)/(A22) | 50 | 98 | 100 | 100 | 0 |
| (A21)/(A22) | 75 | 100 | 100 | 100 | 0 |

Abbreviation in Tables 20 to 26:

"(% coverage)" means the coverage (in percent) of the area by the particular weed

TABLE 21

| Cpd. No. | Application rate [g a.i./ha] | Herbicidal effect (%) on *Poa annua* Post-emergence application without pre-treatment | | | Phytotoxicity (%) on Turf |
|---|---|---|---|---|---|
| | | 123 DAT | 157 DAT | 187 DAT | 157 DAT |
| untreated (% coverage) | — | 0 (87) | 0 (73) | 0 (47) | 0 |
| (A21)/(A22) | 25 | 27 | 77 | 98 | 0 |
| (A21)/(A22) | 50 | 77 | 95 | 100 | 0 |
| (A21)/(A22) | 75 | 98 | 100 | 100 | 0 |

TABLE 22

| Cpd. No. | Application rate [g a.i./ha] | Herbicidal effect (%) on *Veronica arvensis* Pre-emergence application after pre-treatment | | Herbicidal effect (%) on *Veronica arvensis* Post-emergence application without pre-treatment | |
|---|---|---|---|---|---|
| | | 123 DAT | 157 DAT | 123 DAT | 157 DAT |
| untreated (% coverage) | — | 0 (27) | 0 (50) | 0 (27) | 0 (50) |
| (A21)/(A22) | 25 | 81 | 100 | 100 | 94 |
| (A21)/(A22) | 50 | 100 | 100 | 75 | 100 |
| (A21)/(A22) | 75 | 100 | 100 | 100 | 100 |

TABLE 23

| Cpd. No. | Application rate [g a.i./ha] | Herbicidal effect (%) on *Dagitaria sanguinales* Pre-emergence application after pre-treatment | | | |
|---|---|---|---|---|---|
| | | 187 DAT | 207 DAT | 234 DAT | 259 DAT |
| untreated (% coverage) | — | 0 (80) | 0 | 0 | 0 |
| (A21)/(A22) | 25 | 100 | 100 | 97 | 99 |
| (A21)/(A22) | 50 | 100 | 100 | 100 | 100 |
| (A21)/(A22) | 75 | 100 | 100 | 100 | 100 |

TABLE 24

| Cpd. No. | Application rate [g a.i./ha] | Herbicidal effect (%) on *Aphanes arvensis* Pre-emergence application after pre-treatment | Herbicidal effect (%) on *Lamium amplexcaule* Pre-emergence application after pre-treatment | |
|---|---|---|---|---|
| | | 151 DAT | 124 DAT | 151 DAT |
| untreated (% coverage) | — | 0 (20) | 0 (40) | 0 (30) |
| (A21)/(A22) | 25 | 50 | 58 | 40 |
| (A21)/(A22) | 50 | 100 | 100 | 90 |
| (A21)/(A22) | 75 | 100 | 100 | 100 |

TABLE 25

| Cpd. No. | Application rate [g a.i./ha] | Herbicidal effect (%) on *Aphanes arvensis* Post-emergence application without pre-treatment | Herbicidal effect (%) on *Lamium amplexcaule* Post-emergence application without pre-treatment | |
|---|---|---|---|---|
| | | 151 DAT | 124 DAT | 151 DAT |
| untreated (% coverage) | — | 0 (15) | 0 (33) | 0 (10) |
| (A21)/(A22) | 25 | 100 | 91 | 50 |
| (A21)/(A22) | 50 | 33 | 89 | 67 |
| (A21)/(A22) | 75 | 100 | 83 | 67 |

TABLE 26

| Cpd. No. | Application rate [g a.i./ha] | Herbicidal effect (%) on *Stellaria media* Pre-emergence application after pre-treatment | | Herbicidal effect (%) on *Stellaria media* Post-emergence application without pre-treatment | |
|---|---|---|---|---|---|
| | | 124 DAT | 151 DAT | 124 DAT | 151 DAT |
| untreated (% coverage) | — | 0 (40) | 0 (43) | 0 (63) | 0 (53) |
| (A21)/(A22) | 25 | 75 | 71 | 100 | 100 |
| (A21)/(A22) | 50 | 100 | 100 | 100 | 100 |
| (A21)/(A22) | 75 | 100 | 100 | 100 | 100 |

5.2 Specific Example (Effectivity Testing Against Weed Plants), Co-Formulation A co-formulation containing a mixture compounds no. (A21) and (A22) according to Table 1 above, in which compound (A21) is the main component (active ingredient mixture having common name indaziflam) and the other herbicides indicated in the table, was applied with a water volume of aprox 400 liter/ha with a spraying device (knapsack sprayer) on the turf grass species indicated below at the application rate given in the table below. Granules were applied with a shaker can.

Turf maintenance was done according to local practice in respect to mowing intervals, watering and fertilization.
Turf grass species: *Festuca arundinacea*, variety (tall fescue grass)
Weed species: *Trifolium repens*
Location: Sports turf, North Carolina, USA
Plot size: 1.4 m$^2$ and 3 replicates per treatment
Application timing: 27 Mar. 2007, spring application, early post for the weed Effectivity was rated in percent (%) herbicidal effect compared with untreated control according to the method of Abbott mentioned above (see 5.1). 100% efficacy means full control; 0% efficacy means no control of the weed; all ratings above 80% are usually acceptable. The results are summarized in Table 27

TABLE 27

| Cpd. No. | Application rate [g a.i./ha] | Herbicidal effect (%) on *Trifolium repens* | |
|---|---|---|---|
| | | 30 DAT | 381 DAT |
| untreated | — | 0 | 0 |
| (A21)/(A22) 0.013% GR on 30-0-3 Fertilizer granule | 19 | 67 | 78 |
| (A21)/(A22) 0.02% GR on 30-0-3 Fertilizer granule | 29.3 | 33 | 87 |
| (A21)/(A22) 0.033% GR on 30-0-3 Fertilizer granule | 48.3 | 67 | 82 |
| (A21)/(A22) + 2,4-D acid + Mecoprop-P + Dicamba acid | 19.6 + 814 + 196 + 90.4 | 97 | 72 |
| (A21)/(A22) + 2,4-D acid + Mecoprop-P + Dicamba acid | 39.13 + 814 + 196 + 90.4 | 100 | 90 |
| (A21)/(A22) + 2,4-D acid + Mecoprop-P + Dicamba acid | 49.74 + 814 + 196 + 90.4 | 100 | 90 |
| (A21)/(A22) | 50 | 60 | 90 |

Abbreviations in Table 27:
"0.013% GR" means granule containing 0.013% b.w. active ingredient (A), the same applies for 0.02% GR and 0.033% GR, respectively
"30-0-3 Fertilizer granule" means granules of a fertilizer containing 30% b.w. nitrogen, 0% b.w. phosphorus and 3% b.w. potassium,

5.3 Specific Example (Effectivity Testing Against Weed Plants), Co-Formulation The application and evaluation were performed as described in example 5.2 with the following difference:

Turf grass species: *Cynodon dactylon*, variety (bermuda grass)

Weed species: *Digitaria sanguinalis, Poa annua*

The results are summarized in Table 28.

TABLE 28

| Cpd. No. | Application rate [g a.i./ha] | Herbicidal effect (%) on *Digitaria sanguinalis* | | | | | | Herbicidal effect (%) on *Poa annua* |
|---|---|---|---|---|---|---|---|---|
| | | 35 DAT | 56 DAT | 68 DAT | 107 DAT | 138 DAT | 180 DAT | 210 DAT |
| untreated | — | 0 | 0 | 0 | 0 | 0 | 0 | 0 |
| (A21)/(A22) | 12.5 | 87 | 63 | 73 | 70 | 43 | 57 | 70 |
| (A21)/(A22) | 25.0 | 95 | 96 | 98 | 97 | 93 | 93 | 97 |
| (A21)/(A22) | 50.0 | 97 | 98 | 99 | 99 | 100 | 100 | 100 |
| (A21)/(A22) | 100.0 | 96 | 99 | 99 | 99 | 99 | 99 | 100 |
| (A21)/(A22) | 200.0 | 98 | 99 | 99 | 100 | 100 | 100 | 100 |

5.4 Specific Example (Selectivity Testing on Turf Grass and Weed Control), (Co-)Formulations A tank mix containing a mixture compounds no. (A21) and (A22) according to Table 1 above, in which compound (A21) is the main component (active ingredient mixture having common name indaziflam) and the other herbicides indicated in the table, was applied with a water volume of aprox 400 liter/ha with a spraying device (knapsack sprayer) on the turf grass species indicated below at the application rate given in the table below. Turf maintenance was done according to local practice in respect to mowing intervals, watering and fertilization.

Turf grass species: *Cynodon dactylon*, variety (bermuda grass)
Weed species: *Plantago lanceolata, Oxalis stricta, Plantago aristata*
Location: Sports turf, North Carolina, USA
Plot size: 8 m$^2$ and 3 replicates per treatment
Application timing: 7 Jul. 2006, post-emergence for the weed Selectivity evaluation was based on turf quality ratings according to Example 1.3. Herbicidal effectivity in weed control was rated in percent (%) herbicidal effect compared with untreated control according to the method of Abbott (see 5.1). 100% efficacy means full control; 0% efficacy means no control of the weed; all ratings above 80% are usually acceptable. The results are summarized in Tables 29 to 31.

TABLE 29

| Cpd. No. | Application rate [g a.i./ha] | Selectivity evaluation (rating 1-9) | | | | |
|---|---|---|---|---|---|---|
| | | 7 DAT | 14 DAT | 33 DAT | 47 DAT | 61 DAT |
| untreated | — | 9 | 9 | 8 | 9 | 9 |
| (A21)/(A22) + Thiencarbazone-methyl + Metribuzin | 25 + 32 + 560 | 6.7 | 8 | 8.7 | 9 | 9 |
| (A21)/(A22) + Foramsulfuron + Metribuzin | 25 + 28.8 + 280 | 8 | 8.7 | 8.7 | 9 | 9 |
| (A21)/(A22) + Thiencarbazone-methyl + Iodosulfuron-methyl-sodium | 25 + 25 + 5 | 8 | 7.7 | 7.7 | 9 | 9 |

TABLE 30

| Cpd. No. | Application rate [g a.i./ha] | Herbicidal effect (%) against *Plantago lanceolata* | | | |
|---|---|---|---|---|---|
| | | 7 DAT | 14 DAT | 33 DAT | 47 DAT |
| untreated | — | 0 | 0 | 0 | 0 |
| (A21)/(A22) + Thiencarbazone-methyl + Metribuzin | 25 + 32 + 560 | 60 | 90 | 100 | 100 |
| (A21)/(A22) + Foramsulfuron + Metribuzin | 25 + 28.8 + 280 | 53 | 90 | 97 | 100 |
| (A21)/(A22) + Thiencarbazone-methyl + Iodosulfuron-methyl-sodium | 25 + 25 + 5 | 30 | 60 | 97 | 100 |

TABLE 31

| Cpd. No. | Application rate [g a.i./ha] | Herbicidal effect (%) against *Oxalis stricta* | | Herbicidal effect (%) against *Plantago aristata* | | |
|---|---|---|---|---|---|---|
| | | 7 DAT | 14 DAT | 7 DAT | 14 DAT | 33 DAT |
| untreated | — | 0 | 0 | 0 | 0 | 0 |
| (A21)/(A22) + Thiencarbazone-methyl + Metribuzin | 25 + 32 + 560 | 90 | 100 | 60 | 100 | 100 |
| (A21)/(A22) + Foramsulfuron + Metribuzin | 25 + 28.8 + 280 | 80 | 100 | 60 | 100 | 100 |
| (A21)/(A22) + Thiencarbazone-methyl + Iodosulfuron-methyl-sodium | 25 + 25 + 5 | 80 | 93 | 55 | 100 | 100 |

6. Examples for Selectivity and Weed Control in Greenhouse Trials

6.1 Specific Example (Selectivity Testing in Turf Grass Species), Sprayable Formulation Turf grass plants were grown in sandy loam soil in the greenhouse under good growing conditions up to the 1-leaf stage. In parallel tests, a formulation (water-dispersable powder) containing a mixture of the compounds no. (A21) and (A22) of Table 1 above wherein compound (A21) is the main component (active ingredient mixture having common name indaziflam), tank-mix of the above formulation and standard formulation of other combination herbicides, and standard formulations of the single combination herbicides were applied with a water volume of aprox 600 liter/ha on the turf grass plants in the 1-leaf stage at the application rate given in table below. The turf grass plants were further kept under good growing conditions. 7 days after application the selectivity was visually evaluated as percent (%) injury compared to untreated control plants. The results are summarized in the Tables 32 and 33 below.

The results show an unexpected improved selectivity for the active ingredient mixtures.

TABLE 32

| Cpd. No. | Application rate [g a.i./ha] | Selectivity evaluation (% injury) 7 DAT on *Cynodon dactylon* |
|---|---|---|
| untreated | — | 0 |
| (A21)/(A22) | 12 | 15 |
| Ethoxysulfuron | 5 | 0 |
| (A21)/(A22) + Ethoxysulfuron | 12 + 5 | 5 |
| Mesosulfuron-methyl | 5 | 0 |
| (A21)/(A22) + Mesosulfuron-methyl | 12 + 5 | 0 |
| Metosulam | 10 | 0 |
| (A21)/(A22) + Metosulam | 12 + 10 | 0 |
| MCPA | 500 | 0 |
| (A21)/(A22) + MCPA | 12 + 500 | 10 |

TABLE 33

| Cpd. No. | Application rate [g a.i./ha] | Selectivity evaluation (% injury) 7 DAT on *Cynodon dactylon* |
|---|---|---|
| untreated | — | 0 |
| (A21)/(A22) | 12 | 15 |
| Fluroxypyr | 100 | 0 |
| (A21)/(A22) + Fluroxypyr | 12 + 100 | 10 |
| Picloram | 300 | 0 |
| (A21)/(A22) + Picloram | 12 + 300 | 10 |
| Rimsulfuron | 5 | 10 |
| (A21)/(A22) + Rimsulfuron | 12 + 10 | 10 |
| MCPA | 500 | 0 |
| (A21)/(A22) + MCPA | 12 + 500 | 10 |

6.2 Specific Example (Herbicidal Effect in Weed Control), Sprayable Formulation Weed plants were grown in sandy loam soil in the greenhouse under good growing conditions up to the leaves stage indicated in the table below. In parallel tests, a formulation (water-dispersable powder) containing a mixture of the compounds no. (A21) and (A22) of Table 1 above wherein compound (A21) is the main component (active ingredient mixture having common name indaziflam), tank-mix of the above formulation and standard formulation of other combination herbicides, and standard formulations of the single combination herbicides were applied with a water volume of aprox 600 liter/ha on the weed plants at the application rate given in table below. 7 days after application and under good growing conditions, the herbicidal effect was visually evaluated as percent (%) injury compared to untreated control plants. The results are summarized in the Tables 34, 35, 36 and 37 further below.

Remarks as to evaluation of synergistic herbicidal effects:

The results show an unexpected synergistic increase in herbicidal effect for the active ingredient mixtures. That means, when applying the combinations according to the invention, herbicidal effects are observed on a harmful plant species which exceed the formal total of the effects of the herbicides present when these are applied by themselves. Alternatively, it is observed in some cases that a lower application rate is required for the herbicide combination in order to achieve the same effect on a harmful plant species in comparison with the individual products. Such increases in action or efficacy, or reduced application rates, strongly suggest a synergistic effect.

When the data observed already exceed the formal total ($=E^A$) of the data in the experiments with individual applications, they likewise exceed the expected value according to Colby, which is calculated using the formula below and is likewise regarded as an indication of synergism (cf. S. R. Colby; in Weeds 15 (1967) pp. 20 to 22):

$$E = A + B - (A \cdot B / 100)$$

In this formula:
A=action of active compound (A) in % at an application rate of a g of AS/ha;
B=action of active compound (B) in % at an application rate of b g of AS/ha;
E=expected value of the action of the combination (A)+(B) in % at the combined application rate a+b g of AS/ha.

The data observed in the experiments show, at suitably low dosages, an action of the combinations which exceeds the expected values according to Colby ($=E^C$).

TABLE 34

| Cpd. No. | Application rate*[)] [g a.i./ha] | Herbicidal effect (%) 7 DAT on *Capsella bursa pastoris* |
|---|---|---|
| untreated | — | 0 |
| (A21)/(A22) | 6 | 0 |
| Bromoxynil | 100 | 30 |
| (A21)/(A22) + Bromoxynil | 6 + 100 | 40 ($E^A$ = 30) |
| Ethoxysulfuron | 20 | 50 |
| (A21)/(A22) + Ethoxysulfuron | 6 + 20 | 65 ($E^A$ = 50) |
| Fluroxypyr | 100 | 60 |
| (A21)/(A22) + Fluroxypyr | 6 + 100 | 65 ($E^A$ = 60) |

*[)]Application in the 2- to 3-leaves stage (see Table 34)

TABLE 35

| Cpd. No. | Application rate*[)] [g a.i./ha] | Herbicidal effect (%) 7 DAT on *Taraxacum officinalis* |
|---|---|---|
| untreated | — | 0 |
| (A21)/(A22) | 6 | 20 |
| Metosulam | 10 | 10 |
| (A21)/(A22) + Metosulam | 6 + 10 | 45 ($E^A$ = 30) |

TABLE 35-continued

| Cpd. No. | Application rate*) [g a.i./ha] | Herbicidal effect (%) 7 DAT on *Taraxacum officinalis* |
|---|---|---|
| Mecoprop-P | 500 | 20 |
| (A21)/(A22) + Mecoprop-P | 6 + 500 | 65 ($E^A = 40$) |
| Glyphosate | 200 | 40 |
| (A21)/(A22) + Glyphosate | 6 + 200 | 75 ($E^A = 40$) |

*)Application in the 1- to 2-leaves stage (see Table 35)

TABLE 36

| Cpd. No. | Application rate*) [g a.i./ha] | Herbicidal effect (%) 7 DAT on *Trifolium pratense* |
|---|---|---|
| untreated | — | 0 |
| (A21)/(A22) | 6 | 10 |
| Metsulfuron-methyl | 5 | 30 |
| (A21)/(A22) + Metsulfuron-methyl | 6 + 5 | 70 ($E^A = 40$) |
| Rimsulfuron | 5 | 40 |
| (A21)/(A22) + Rimsulfuron | 6 + 5 | 65 ($E^A = 50$) |
| MCPA | 500 | 30 |
| (A21)/(A22) + MCPA | 6 + 500 | 60 ($E^A = 40$) |
| Fenoxaprop-P-ethyl | 45 | 0 |
| (A21)/(A22) + Fenoxaprop-P-ethyl | 6 + 45 | 50 ($E^A = 10$) |
| Carfentrazone-ethyl | 8 | 0 |
| (A21)/(A22) + Carfentrazone | 6 + 8 | 60 ($E^A = 10$) |

*)Application in the 3-leaves stage (see Table 36)

TABLE 37

| Cpd. No. | Application rate*) [g a.i./ha] | Herbicidal effect (%) 7 DAT on *Echinocloa crus-galli* |
|---|---|---|
| untreated | — | 0 |
| (A21)/(A22) | 6 | 0 |
| Picloram | 300 | 30 |
| (A21)/(A22) + Picloram | 6 + 300 | 35 ($E^A = 30$) |

*)Application in the 3- to 4-leaves stage (see Table 37)

7. Examples for Selectivity and Weed Control in Field Trials 7.1 Specific Mixture Example for Weed Control in Pre-Emergence Application Seeds or rhizome pieces of monocotyledonous and dicotyledonous weed plants were placed in the field in sandy loam soil and covered with soil. In parallel tests, a formulation (water-dispersable powder) containing a mixture of the compounds no. (A21) and (A22) of Table 1 above wherein compound (A21) is the main component (active ingredient mixture having common name indaziflam), tank-mix of the above formulation and standard formulation of other combination herbicides, and standard formulations of the single combination herbicides were applied with a water volume of aprox 600 liter/ha on the soil cover at the application rate given in table below. 12 days after application (12 DAT), the herbicidal effect on the developed weed plants was visually evaluated as percent (%) herbicidal effect compared to untreated control plants. The results are summarized in the Tables 38 and 39 below and show a synergistic increase in herbicidal effect of the mixtures of active ingredients.

TABLE 38

Weed control in pre-emergence application

| Cpd. No. | Application rate [g a.i./ha] | Herbicidal effect (%) 12 DAT on *Brachiaria decumbens* |
|---|---|---|
| (A21)/(A22) | 25 | 85 |
| Ethoxysulfuron | 30 | 0 |
| (A21)/(A22) + Ethoxysulfuron | 25 + 30 | 95 ($E^A = 85$) |
| (Fluroxypyr-1-methylheptyl + Picloram) | (72 + 50) | 0 |
| (A21)/(A22) + (Fluroxypyr-1-methylheptyl + Picloram) | 25 + (72 + 50) | 100 ($E^A = 85$) |
| Mesosulfuron-methyl | 5 | 0 |
| (A21)/(A22) + Mesosulfuron-methyl | 25 + 5 | 90 ($E^A = 85$) |
| (Picloram + 2,4-D) | (50 + 188) | 0 |
| (A21)/(A22) + (Picloram + 2,4-D) | 25 + (50 + 188) | 88 ($E^A = 85$) |

TABLE 39

Weed control in pre-emergence application

| Cpd. No. | Application rate [g a.i./ha] | Herbicidal effect (%) 12 DAT on *Brachiaria decumbens* |
|---|---|---|
| (A21)/(A22) | 25 | 85 |
| Fenoxaprop-P-ethyl | 60 | 0 |
| (A21)/(A22) + Fenoxaprop-P-ethyl | 25 + 60 | 93 ($E^A = 85$) |
| Carfentrazone-ethyl | 15 | 0 |
| (A21)/(A22) + Carfentrazone-ethyl | 25 + 15 | 94 ($E^A = 85$) |
| Glyphosate-potassium salt (K salt) | 840 | 0 |
|  | 620 | 0 |
| (A21)/(A22) + Glyphosate-K salt | 25 + 840 | 95 ($E^A = 85$) |
|  | 25 + 620 | 92 ($E^A = 85$) |

7.2 Specific Mixture Example for Weed Control and Compatibility in Turf Grass in Post-Emergence Application Seeds or rhizome pieces of monocotyledonous and dicotyledonous weed plants and specific warm season turf grasses were placed in the field in sandy loam soil, covered with soil and grown until the plants had reached the leaves stage indicated in the tables. In parallel tests, a formulation (water-dispersable powder) containing a mixture of the compounds no. (A21) and (A22) of Table 1 above wherein compound (A21) is the main component (active ingredient mixture having common name indaziflam), tank-mix of the above formulation and standard formulation of other combination herbicides, and standard formulations of the single combination herbicides were applied with a water volume of aprox 600 liter/ha on the test plants at the application rate given in table below. The herbicidal effect was visually evaluated as percent (%) herbicidal effect compared to untreated control plants. The results are summarized in Table 40 below and show a synergistic increase in herbicidal effect of the mixtures of active ingredients and a good safety of the turf grass.

TABLE 40

Weed control in post-emergence application and turf grass safety

| Cpd. No. | Application rate[1)2)] [g a.i./ha] | Herbicidal effect (%) on *Commelina benghalensis*[3)] | Herbicidal effect (%) on *Paspalum notatum* (warm season turf grass)[4)] |
|---|---|---|---|
| (A21)/(A22) | 25 | 5 | 0 |
| (Fluroxypyr-1-methylheptyl + Picloram) | (72 + 50) | 8 | 0 |
| (A21)/(A22) + (Fluroxypyr-1-methylheptyl + Picloram) | 25 + (72 + 50) | 65 ($E^A = 13$) | 0 |
| Mesosulfuron-methyl | 5 | 47 | 0 |
| (A21)/(A22) + Mesosulfuron-methyl | 25 + 5 | 82 ($E^A = 52$) | 0 |
| (Picloram + 2,4-D) | (50 + 188) | 86 | 0 |
| (A21)/(A22) + (Picloram + 2,4-D) | 25 + (50 + 188) | 96 ($E^A = 91$) ($E^C = 87$) | 0 |
| (Picloram + 2,4-D) | (50 + 188) | 0 | 0 |
| (A21)/(A22) + (Picloram + 2,4-D) | 25 + (50 + 188) | 88 ($E^A = 85$) | 3 |
| Carfentrazone-ethyl | 15 | 59 | 0 |
| (A21)/(A22) + Carfentrazone-ethyl | 25 + 15 | 89 ($E^A = 64$) ($E^C = 61$) | 0 |
| Glyphosate-potassium salt | 840 | 62 | 40[5)] |
| (K salt) | 620 | 62 | 23[5)] |
| (A21)/(A22) + Glyphosate-K salt | 25 + 840 | 87 ($E^A = 67$) | 42[5)] |
|  | 25 + 620 | 84 ($E^A = 67$) | 34[5)] |

Abbreviations in Table 40:

[1)]Application to *Commelina benghalensis* in the 2-leaves stage
[2)]Application to *Paspalum notatum* in the 3-leaves stage
[3)]Evaluation of herbicidal effect 12 DAT
[4)]Evaluation of herbicidal effect 7 DAT
[5)]Turf grass used is not glyphosate tolerant

7.3 Comparative Example—Selectivity in Cereal Crops

The high selectivity of the compounds of formula (I) in turf is advantageous and not shown to a comparable level in other monocotyledonous crops such as cereals. This can be seen in the following example.

Seeds some cereal crops were placed in sandy loam soil and grown in the field up to early post (post emergence). In parallel tests, a formulation (water-dispersable powder) containing a mixture of the compounds no. (A21) and (A22) of Table 1 above wherein compound (A21) is the main component (active ingredient mixture having common name indaziflam) was applied with a water volume of aprox 600 liter/ha on the plants at the application rate given in table below. The plants were surveyed several weeks after application while the herbicidal effect was visually evaluated as percent (%) injury compared to untreated control plants. The results summarized in Table 41 below represent the maximum herbicidal effect observed over the survey period.

TABLE 41

Injury of cereal crops in early post emergence application

| Cpd. No. | Application rate[1)] [g a.i./ha] | Injury (%) on | | | |
|---|---|---|---|---|---|
| | | HORVS | ORYSW | TRZAW | ZEAMX |
| (A21)/(A22) | 25 | 57 | 71 | 53 | 30 |

Abbreviations in Table 41:
[1)]Application early post (in the 1-to 3-leaves stage)
HORVS = *Hordeum vulgare* L. (spring barley)
ORYSW = *Oryza sativa* L. (seeded paddy rice)
TRZAW = *Triticum aestivum* W (winter wheat)
ZEAMX = *Zea mays* L. (common maize)

The evaluation shows a substantial injury of the cereal plants. Contrary to the application in turf (see examples 7.1, 7.2 and 1 to 6) the test compounds are not suitable for selective weed control in cereal crops at the defined application rate.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method for selectively controlling weeds on lawn or turf, comprising:
    applying one or more herbicides (A), optionally together with, before, or after the application of one or more other active ingredients, to the weeds, parts of the weed plants, seeds of the weed plants, or the area under cultivation where the plants of lawn or turf are growing, sown, or to be sown;
    wherein the one or more other active ingredients is/are selected from the group consisting of other herbicides useful in the treatment of lawn or turf, and optionally other active ingredients (C) useful in the treatment of lawn or turf;
    wherein the herbicides (A) are one or more compounds of the formula (I) or salts thereof, the formula (I) being:

(I)

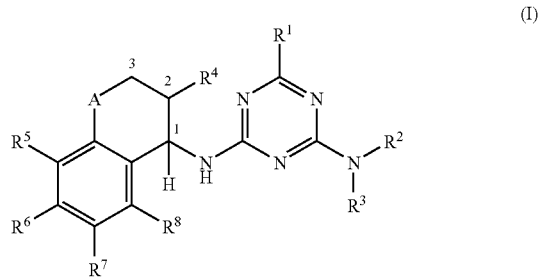

where:
R¹ is a group of the formula $CZ^1Z^2Z^3$, where:
 $Z^1$ is fluoro;
 $Z^2$ is methyl; and
 $Z^3$ is H;
$R^2$ is H;
$R^3$ is H;
$R^4$ is methyl;
$R^5$ is H; and
$R^6$ is H;
$R^7$ is methyl;
$R^8$ is H; and
A is a direct bond.

2. The method as claimed in claim 1;
wherein the compounds (I) or salts thereof are optically active, where the stereochemical configuration at the carbon atom marked with the number 1 in formula (I) is the (R)-configuration having an optical purity corresponding to 60 to 100% (R)-isomer or isomers relative to the total amount of the stereoisomer(s) contained in the compound having (R)- and (S)-configuration at the position 1.

3. The method as claimed in claim 1;
wherein the herbicides (B) are selected from the group consisting of:
 (B1) 2,4-D and esters and salts thereof;
 (B2) Amidosulfuron or salts thereof;
 (B3) Aminocyclopyrachlor or salts or esters thereof;
 (B4) Aminopyralid or salts thereof;
 (B5) Btomoxynil or esters thereof;
 (B6) Diflufenican;
 (B7) Ethofumesate;
 (B8) Ethoxysulfuron or salts thereof;
 (B9) Fluroxypyr or esters thereof;
 (B10) Fatty acids;
 (B11) Glufosinate or salts thereof;
 (B12) Glufosinate-P (=L-Glufosinate or phosphinothricin) or salts thereof;
 (B13) Glyphosate or salts thereof;
 (B14) Iodosulfuron and esters and salts thereof;
 (B15) Mesosulfuron and esters or salts thereof;
 (B16) Metosulam;
 (B17) Paraquat and salts thereof;
 (B18) Penoxsulam and salts thereof;
 (B19) Picloram and esters and salts thereof;
 (B20) Pyrasulfotole and salts thereof;
 (B21) Pyroxasulfone (KIH-485) and salts thereof;
 (B22) Pyroxsulam and salts thereof;
 (B23) Rimsulfuron and salts thereof;
 (B24) Saflufenacil and salts thereof;
 (B25) Sclerotinia (biological herbicides);
 (B26) SYN-449 and salts thereof;
 (B27) SYN-523 and salts thereof;
 (B28) Tembotrione and salts thereof;
 (B29) Thiencarbazone and esters and salts thereof;
 (B30) Thifensulfuron and esters and salts thereof;
 (B31) Tribenuron and esters and salts thereof;
 (B32) Trifloxysulfuron and salts thereof;
 (B33) Dicamba and esters and salts thereof;
 (B34) Mecoprop and Mecoprop-P, and esters and salts thereof;
 (B35) MCPA and esters and salts thereof;
 (B36) Fenoxaprop and esters and salts thereof;
 (B37) Fenoxaprop-P, and esters and salts thereof;
 (B38) Carfentrazone, and esters and salts thereof;
 (B39) Sulfentrazone and salts thereof;
 (B40) Oxadiazon and salts thereof;
 (B41) Metsulfuron and esters and salts thereof;
 (B42) Triclopyr and esters and salts thereof;
 (B43) Foramsulfuron or salts thereof; and
 (B44) Metribuzin or salts thereof.

4. The method as claimed in claim 1;
wherein the active ingredients (C) are selected from the group consisting of:
 insecticides, acaricides, fungicides, safeners, fertilizers, growth regulators, and nutrients useful for treating lawn or turf against phytopathogenic diseases or for growth regulation or growth promotion of lawn or turf.

5. The method as claimed in claim 1;
wherein the compound of formula (I) or salt thereof is applied to the locus of the turfgrass before or after emergence of the weeds.

6. The method as claimed in claim 1;
wherein the compound of formula (I) or salt thereof is applied to the locus of the weed plants and lawn or turf plants pre-plant or pre-emergence of the lawn or turf.

7. The method as claimed in claim 1;
wherein the compound of formula (I) or salt thereof is applied to the locus of the weed plants and of an established lawn or turf.

8. The method as claimed in claim 1;
wherein from 0.01 to 2000 g of the compound of formula (I) or salt thereof is applied per hectare lawn or turf.

9. A method for weed control on lawn or turf comprising:
applying a herbicide (A) before, simultaneously with or after a herbicide (B) to the weed plants, seeds thereof, or the area where the weed plants are growing or are supposed to grow, or the area under cultivation, where the plants of lawn or turf are growing, sown, or to be sown; wherein the herbicide (A) is one or more compounds of formula (I) or a salt thereof as defined in claim 1; and wherein herbicide (B) is selected from the group consisting of:
 (B5) Bromoxynil or esters thereof;
 (B8) Ethoxysulfuron or salts thereof;
 (B10) Fatty acids;
 (B15) Mesosulfuron and esters or salts thereof;
 (B16) Metosulam;
 (B25) Sclerotinia (biological herbicides);
 (B34) Mecoprop and Mecoprop-P and esters and salts thereof;
 (B35) MCPA and esters and salts thereof;
 (B36) Fenoxaprop and esters and salts thereof; and
 (B37) Fenoxaprop-P and esters and salts thereof.

10. The method as claimed in claim 1;
wherein the herbicides (A) is a combination of compounds of the formula:

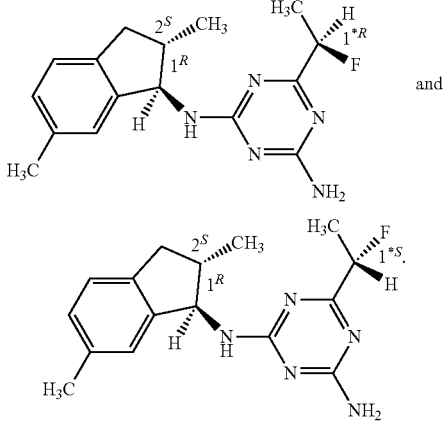

and

11. The method of claim 10;
where no (B) herbicides or (C) active ingredients are present in the composition.

12. The method of claim 11;
where no active ingredients (C) are present in the composition.
13. The method of claim 9;
wherein the compound (B) is selected from the group consisting of:
(B5) Bromoxynil or esters thereof;
(B8) Ethoxysulfuron or salts thereof;
(B10) Fatty acids;
(B15) Mesosulfuron and esters or salts thereof;
(B16) Metosulam;
(B25) Sclerotinia (biological herbicides);
(B34) Mecoprop and Mecoprop-P, and esters and salts thereof;
(B35) MCPA and esters and salts thereof;
(B36) Fenoxaprop and esters and salts thereof; and
(B37) Fenoxaprop-P and esters and salts thereof.
14. The method as claimed in claim 3;
wherein the herbicide (B2) is (B2.1) Amidosulfuron;
wherein the herbicide (B3) is selected from the group consisting of (B3.1) Aminocyclopyrachlor and (B3.2) Aminocyclopyrachlor-methyl;
wherein the herbicide (B4) is (B4.1) Aminopyralid;
wherein the herbicide (B5) is selected from the group consisting of (B5.1) Bromoxynil, (B5.2) Bromoxynil-heptanoate and (B5.3) Bromoxynil-octanoate;
wherein the herbicide (B8) Ethoxysulfuron is selected from the group consisting of (B8.1) Ethoxysulfuron and (B8.2) Ethoxysulfuron-sodium;
wherein the herbicide (B9) is selected from the group consisting of (B9.1) Fluroxypyr, (B9.2) Fluroxypyr-meptyl, and (B9.3) Fluroxypyr-2-butoxy-1-methylethyl;
wherein the herbicide (B10) is (B10.1) acetic acid;
wherein the herbicide (B11) is selected from the group consisting of (B11.1) Glufosinate, (B11.2) Glufosinate-ammonium, and (B11.3) Glufosinate-sodium;
wherein the herbicide (B12) is selected from the group consisting of (B12.1) Glufosinate-P, (B12.2) Glufosinate-P-sodium, and (B12.3) Glufosinate-P-ammonium;
wherein the herbicide (B13) is selected from the group consisting of (B13.1) Glyphosate, (B13.2) Glyphosate-sodium, (B13.3) Glyphosate-potassium, (B13.4) Glyphosate-ammonium, (B13.5) Glyphosate-diammonium, and (B13.6) Glyphosate-isopropylammonium;
wherein the herbicide (B14) is selected from the group consisting of (B14.1) Iodosulfuron, (B14.2) Iodosulfuron-methyl, and (B14.3) Iodosulfuron-methyl-sodium;
wherein the herbicide (B15) is selected from the group consisting of (B15.1) Mesosulfuron and (B15.2) Mesosulfuron-methyl;
wherein the herbicide (B17) is (B17.1) Paraquat-dichloride;
wherein the herbicide (B18) is (B18.1) Penoxsulam;
wherein the herbicide (B19) is selected from the group consisting of (B19.1) Picloram, (B19.2) Picloram-potassium, (B19.3) Picloram-dimethylammonium, (B19.4) Picloram-triisopropylammonium, (B19.5) Picloram-triethanolammonium, (B19.6) Picloram-triisopropanolammonium, and (B19.7) Picloram-isooctyl;
wherein the herbicide (B20) is (B20.1) Pyrasulfotole;
wherein the herbicide (B21) is (B21.1) Pyroxasulfone;
wherein the herbicide (B22) is (B22.1) Pyroxulam;
wherein the herbicide (B23) is (B23.1) Rimsulfuron;
wherein the herbicide (B24) is (B24.1) Saflufenacil;
wherein the herbicide (B26) is (B26.1) SYN-449;
wherein the herbicide (B27) is (B27.1) SYN-523;
wherein the herbicide (B28) is (B28.1) Tembotrione;
wherein the herbicide (B29) is selected from the group consisting of (B29.1) Thiencarbazone, (B29.2) Thiencarbazone-methyl, and (B29.3) Thiencarbazone-methyl-sodium;
wherein the herbicide (B30) is selected from the group consisting of (B30.1) Thifensulfuron, (B30.2) Thifensulfuron-methyl, and (B30.3) Thifensulfuron-methyl-sodium;
wherein the herbicide (B31) is selected from the group consisting of (B31.1) Tribenuron, (B31.2) Tribenuron-methyl, and (B31.3) Tribenuron-methyl-sodium;
wherein the herbicide (B32) is selected from the group consisting of (B32.1) Trifloxysulfuron and (B32.2) Trifloxysulfuron-sodium;
wherein the herbicide (B33) is selected from the group consisting of (33.1) Dicamba, (33.2) Dicamba-sodium, (33.3) Dicamba-potassium, (33.4) Dicamba-dimethylammonium, (33.5) Dicamba-isopropylammonium, (33.5) Dicamba-diglycolamin salt, and (33.4) Dicamba-butotyl;
wherein the herbicide (B34) is selected from the group consisting of (34.1) Mecoprop and esters and salts thereof, (34.2) Mecoprop-P and esters and salts thereof, (34.3) Mecoprop, (34.4) Mecoprop-P, (34.5) Mecoprop-sodium, (34.6) Mecoprop-butotyl, (34.7) Mecoprop-P, (34.8) Mecoprop-P-sodium, (34.9) Mecoprop-P-potassium, (34.10) Mecoprop-P-butotyl, and (34.11) Mecoprop-P-2-ethyl-hexyl;
wherein the herbicide (B35) is selected from the group consisting of (35.1) MCPA, (35.2) MCPA-sodium, (35.3) MCPA-potassium, (35.4) MCPA-dimethylammonium, and (35.5) Mecoprop-P-2-ethyl-hexyl;
wherein the herbicide (B36) is selected from the group consisting of (36.1) Fenoxaprop and (36.2) Fenoxaprop-ethyl;
wherein the herbicide (B37) is selected from the group consisting of (36.1) Fenoxaprop-P and (37.2) Fenoxaprop-P-ethyl;
wherein the herbicide (B38) is selected from the group consisting of (38.1) Carfentrazone and (38.2) Carfentrazone-ethyl;
wherein the herbicide (B39) is (39.1) Sulfentrazone;
wherein the herbicide (B40) is (40.1) Oxadiazon;
wherein the herbicide (B41) is selected from the group consisting of (41.1) Metsulfuron and (41.2) Metsulfuron-methyl;
wherein the herbicide (B42) is selected from the group consisting of (42.1) Triclopyr, (43.2) Triclopyr-triethylammonium and (42.3) Triclopyr-butotyl;
wherein the herbicide (B43) is (43.1) Foramsulfuron; and
wherein the herbicide (B44) is Metribuzin (B44.1).
15. The method as claimed in claim 13;
wherein the compound (B5) is selected from the group consisting of (B5.1) Bromoxynil, (B5.2) Bromoxynil-heptanoate, (B5.3) Bromoxynil-octanoate;
wherein the compound (B8) is selected from the group consisting of (B8.1) Ethoxysulfuron and (B8.2) Ethoxysulfuron-sodium;
wherein the compound (B10) is selected from the group consisting of (B10.8) nonanoic acid and (B10.9) decanoic acid;
wherein the compound (B15) is selected from the group consisting of (B15.1) Mesosulfuron and (B15.2) Mesosulfuron-methyl;
wherein the compound (B34) is selected from the group consisting of (34.1) Mecoprop and esters and salts thereof, (34.2) Mecoprop-P and esters and salts thereof, (34.3) Mecoprop, (34.4) Mecoprop-P, (34.5) Mecoprop-sodium, (34.6) Mecoprop-butotyl, (34.7) Mecoprop-P, (34.8) Mecoprop-P-sodium, (34.9) Mecoprop-P-potassium, (34.10) Mecoprop-P-butotyl, and (34.11) Mecoprop-P-2-ethyl-hexyl;

wherein the compound (B35) is selected from the group consisting of (35.1) MCPA, (35.2) MCPA-sodium, (35.3) MCPA-potassium, (35.4) MCPA-dimethylammonium, and (35.5) Mecoprop-P-2-ethyl-hexyl;

wherein the compound (B36) is selected from the group consisting of (36.1) Fenoxaprop and (36.2) Fenoxaprop-ethyl; and wherein the compound (B37) is selected from the group consisting of (36.1) Fenoxaprop-P and (37.2) Fenoxaprop-P-ethyl.

* * * * *